(12) United States Patent
Goldspink et al.

(10) Patent No.: US 11,672,936 B2
(45) Date of Patent: Jun. 13, 2023

(54) ELBOW ASSEMBLY

(71) Applicant: ResMed Pty Ltd, Bella Vista (AU)

(72) Inventors: Lachlan Richard Goldspink, Sydney (AU); Robert Anthony Paterson, Hornsby Heights (AU); Shiva Kumar Shanmuga Sundara, Sydney (AU); Skye Kimberley Short, Sydney (AU); Hargopal Verma, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 453 days.

(21) Appl. No.: 16/878,846

(22) Filed: May 20, 2020

(65) Prior Publication Data

US 2020/0353198 A1 Nov. 12, 2020

Related U.S. Application Data

(63) Continuation of application No. 15/759,893, filed as application No. PCT/AU2016/050892 on Sep. 23, 2016, now Pat. No. 10,675,430.
(Continued)

(51) Int. Cl.
*A61M 16/08* (2006.01)
*A61M 16/06* (2006.01)
(Continued)

(52) U.S. Cl.
CPC .... *A61M 16/0825* (2014.02); *A61M 16/0057* (2013.01); *A61M 16/06* (2013.01);
(Continued)

(58) Field of Classification Search
CPC .............. A61M 16/06; A61M 16/0616; A61M 16/0622; A61M 16/08; A61M 16/0816; A61M 16/0825; A61M 16/0833; A61M 16/0866; A61M 16/0875; A61M 16/20; A61M 16/208; A61M 39/1055; A61M 2205/42
See application file for complete search history.

(56) References Cited

U.S. PATENT DOCUMENTS 4,322,098 A 3/1982 Warshawsky
4,782,832 A 11/1988 Trimble et al.
(Continued)

FOREIGN PATENT DOCUMENTS

EP 1672265 A1 6/2006
FR 832864 A 10/1938
(Continued)

OTHER PUBLICATIONS

West, John B., "Respiratory Physiology", Lippincott Williams & Wilkins, 9$^{th}$ edition, pub. 2012.
(Continued)

*Primary Examiner* — Joseph D. Boecker
(74) *Attorney, Agent, or Firm* — Nixon & Vanderhye P.C.

(57) ABSTRACT

An elbow assembly for a patient interface includes a swivel component adapted to connect to a patient interface and an elbow component adapted to connect to an air circuit. The swivel component is coupled to the elbow component by a ball and socket joint and a hinge joint which allows the elbow component to pivot relative to the swivel component about a single axis.

20 Claims, 66 Drawing Sheets

Related U.S. Application Data

(60) Provisional application No. 62/376,718, filed on Aug. 18, 2016, provisional application No. 62/222,435, filed on Sep. 23, 2015.

(51) Int. Cl.
  *A61M 16/00*  (2006.01)
  *A61M 16/20*  (2006.01)
  *F16L 27/04*  (2006.01)

(52) U.S. Cl.
  CPC .... *A61M 16/0616* (2014.02); *A61M 16/0683* (2013.01); *A61M 16/0816* (2013.01); *A61M 16/20* (2013.01); *A61M 16/0069* (2014.02); *A61M 2202/0225* (2013.01); *A61M 2205/42* (2013.01); *F16L 27/04* (2013.01)

(56) References Cited

U.S. PATENT DOCUMENTS

| | | | |
|---|---|---|---|
| 4,944,310 A | 7/1990 | Sullivan | |
| 6,532,959 B1 | 3/2003 | Berthon-Jones | |
| 6,581,594 B1 | 6/2003 | Drew et al. | |
| 6,907,882 B2 | 6/2005 | Ging et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 8,887,726 B2 | 11/2014 | Schulz et al. | |
| 10,675,430 B2 * | 6/2020 | Goldspink | A61M 16/0816 |
| 2004/0035419 A1 * | 2/2004 | Serowski | A61M 16/06 128/202.27 |
| 2004/0112385 A1 * | 6/2004 | Drew | A61M 16/0605 128/207.12 |
| 2007/0175480 A1 | 8/2007 | Gradon et al. | |
| 2008/0047561 A1 * | 2/2008 | Fu | A61M 16/08 128/207.12 |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2010/0229866 A1 | 9/2010 | Sullivan | |
| 2012/0067349 A1 | 3/2012 | Barlow et al. | |
| 2013/0247915 A1 | 9/2013 | Haibach | |
| 2014/0083430 A1 | 3/2014 | Matula, Jr. et al. | |
| 2014/0150798 A1 * | 6/2014 | Fong | A61M 16/0622 128/206.21 |
| 2015/0013678 A1 | 1/2015 | McAuley et al. | |
| 2015/0352308 A1 * | 12/2015 | Cullen | A61M 16/0875 128/205.25 |
| 2016/0310688 A1 * | 10/2016 | Rothermel | A61M 16/06 |
| 2017/0065786 A1 * | 3/2017 | Stephenson | A61M 16/0816 |
| 2017/0269460 A1 | 9/2017 | Fagerkvist | |
| 2018/0236200 A1 | 8/2018 | Goldspink et al. | |
| 2018/0250485 A1 | 9/2018 | Zhan | |
| 2019/0001094 A1 | 1/2019 | Liu | |

FOREIGN PATENT DOCUMENTS

| | | |
|---|---|---|
| JP | 2008-507305 A | 3/2008 |
| JP | 2009-501577 A | 1/2009 |
| JP | 2009-539497 A | 11/2009 |
| JP | 2012-526592 A | 11/2012 |
| JP | 2013-116409 A | 6/2013 |
| JP | 2014-131790 A | 7/2014 |
| JP | 2014-520576 A | 8/2014 |
| WO | 98/04310 | 2/1998 |
| WO | 98/34665 | 8/1998 |
| WO | 00/78381 | 12/2000 |
| WO | 2000/078381 A1 | 12/2000 |
| WO | 2004/073778 | 9/2004 |
| WO | 2004/096332 A1 | 11/2004 |
| WO | 2005/063328 | 7/2005 |
| WO | 2006/074513 | 7/2006 |
| WO | 2006/130903 | 12/2006 |
| WO | 2009/052560 | 4/2009 |
| WO | 2009/108995 A1 | 9/2009 |
| WO | 2010/135785 | 12/2010 |
| WO | 2011/022751 A1 | 3/2011 |
| WO | 2012/171072 A1 | 12/2012 |
| WO | 2013/020167 A1 | 2/2013 |
| WO | WO 2013/170290 A1 | 11/2013 |
| WO | 2014/165906 A1 | 10/2014 |
| WO | 2015/006826 A1 | 1/2015 |
| WO | 2015/088362 | 6/2015 |
| WO | 2016/041019 A1 | 3/2016 |
| WO | 2016/141430 A1 | 9/2016 |
| WO | 2016/149769 A2 | 9/2016 |
| WO | 2017/049356 A1 | 3/2017 |
| WO | 2017/049358 A1 | 3/2017 |
| WO | 2017/049360 A1 | 3/2017 |
| WO | 2017/049361 A1 | 3/2017 |

OTHER PUBLICATIONS

International Search Report for PCT/AU2016/050892, dated Nov. 17, 2016, 5 pages.
Written Opinion for PCT/AU2016/050892, dated Nov. 17, 2016, 5 pages.
Written Opinion for PCT/AU2016/050892, dated Oct. 5, 2017, 4 pages.
International Preliminary Report on Patentability for PCT/AU2016/050892, dated Dec. 14, 2017, 12 pages.
Extended European Search Report dated May 3, 2019 in European Application No. 16847655.4, 8 pages.
Notice of Reasons for Rejection dated Aug. 31, 2020 in Japanese Application No. 2018-533974, with English translation, 5 pages.
Notice of Reasons for Rejection dated Oct. 17, 2022 in Japanese Application No. 2021-032494, with English translation, 12 pages.

* cited by examiner

Copyright 2012 ResMed Limited

Copyright 2012 ResMed Limited

Relatively Large Positive Curvature

Relatively Small Positive Curvature

Zero Curvature

Relatively Small Negative Curvature

Relatively Large Negative Curvature

Copyright 2015 ResMed Limited

Left-hand rule

Right-hand rule

Left ear helix

Right-hand helix
Right-hand positive

Right ear helix

Copyright 2015 ResMed Limited

ELBOW ASSEMBLY

CROSS-REFERENCE TO RELATED APPLICATIONS

This application is a continuation of U.S. application Ser. No. 15/759,893, filed Mar. 14, 2018, which is the U.S. national phase of International Application No. PCT/AU2016/050892, filed Sep. 23, 2016, which designated the U.S. and claims the benefit of U.S. Provisional Application No. 62/222,435, filed Sep. 23, 2015, and U.S. Provisional Application No. 62/376,718, filed Aug. 18, 2016, each of which is incorporated herein by reference in its entirety.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

1 BACKGROUND OF THE TECHNOLOGY

1.1 Field of the Technology

The present technology relates to one or more of the detection, diagnosis, treatment, prevention and amelioration of respiratory-related disorders. The present technology also relates to medical devices or apparatus, and their use.

1.2 Description of the Related Art 1.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

1.2.2 Therapy

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

1.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

1.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the patient's face when force is applied to the patient interface with the seal-forming portion in confronting engagement with the patient's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris, however some patients find these uncomfortable.

Another form of seal-forming portion may use adhesive to achieve a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063, 328 and WO 2006/130,903 (describing amongst other things aspects of the ResMed Limited MIRAGE LIBERTY™ full-face mask); International Patent Application WO 2009/ 052,560 (describing amongst other things aspects of the ResMed Limited SWIFT™ FX nasal pillows).

1.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

1.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

1.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

1.2.3.4 Data Management

There may be clinical reasons to obtain data to determine whether the patient prescribed with respiratory therapy has been "compliant", e.g. that the patient has used their RPT device according to certain a "compliance rule". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

1.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

1.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient. The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB (A) (uncertainty) | A-weighted sound pressure dB (A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |

-continued

| Mask name | Mask type | A-weighted sound power level dB (A) (uncertainty) | A-weighted sound pressure dB (A) (uncertainty) | Year (approx.) |
|---|---|---|---|---|
| ResMed Mirage™ FX | nasal | 26 (3) | 18 (3) | 2010 |
| ResMed Mirage Swift™ (*) | nasal pillows | 37 | 29 | 2004 |
| ResMed Mirage Swift™ II | nasal pillows | 28 (3) | 20 (3) | 2005 |
| ResMed Mirage Swift™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 cmH$_2$O) Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

1.2.4 Diagnosis and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a person in order to record various bodily signals such as electroencephalography (EEG), electrocardiography (ECG), electrooculography (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home sleep testing.

Clinical experts may be able to diagnose or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

2 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

Another aspect of the present technology relates to an elbow assembly for a patient interface including a swivel component adapted to connect to a patient interface and an elbow component adapted to connect to an air circuit. The swivel component is coupled to the elbow component by a ball and socket joint and a hinge joint which allows the elbow component to pivot relative to the swivel component about a single axis.

Another aspect of the present technology relates to an elbow assembly for a patient interface including a swivel component adapted to connect to a patient interface and an elbow component adapted to connect to an air circuit. The swivel component is coupled to the elbow component by a hinge joint which allows the elbow component to pivot relative to the swivel component about a single axis.

In an example, the swivel component includes a pair of spring arms structured and arranged to connect to the patient interface. In an example, the hinge joint is structured and arranged to prevent the elbow component from rotating into or contacting the spring arms. In an example, the swivel component includes a plurality of vent holes for gas washout. In an example, the swivel component includes an inner radial wall and an outer radial wall that define a radial channel leading to the plurality of vent holes. In an example, tracks or guide walls are provided within the channel to provide discrete flow paths to the plurality of vent holes. In an example, at least a portion of the inner radial wall includes an inwardly extending lip or chevron structured and arranged to redirect flow in a manner that reduces noise and/or minimizes flow directly onto sensitive parts of the patient's face. In an example, the elbow component includes a ball portion engaged within an opening of the swivel component to form the ball and socket joint. In an example, the ball portion includes a pair of opposed recesses engaged with respective pivot pins of the swivel component to form the hinge joint. In an example, each of recesses includes tapered sides leading to a generally circular opening. In an example, the elbow component houses a pair of anti-asphyxia valves. In an example, the elbow component houses a pair of anti-asphyxia valves. In an example, the elbow component includes a first end and a second end connected by an ultrasonic weld connection. In an example, a swivel connector is provided to the elbow component and adapted to connect to the air circuit. In an example, the swivel connector is connected to the elbow component by a snap-fit connection. In an example, the swivel connector is connected to the elbow component by an overmold connection. In an example, the swivel component comprises a hard-to-hard connection with the patient interface. In an example, the swivel component is structured to form a dynamic diametric seal and a dynamic face seal with the patient interface to provide a tortuous leak path.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Treatment Systems

FIG. 1A shows a system including a patient 1000 wearing a patient interface 3000, in the form of a nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown.

3.2 Respiratory System and Facial Anatomy

Figure 2A:
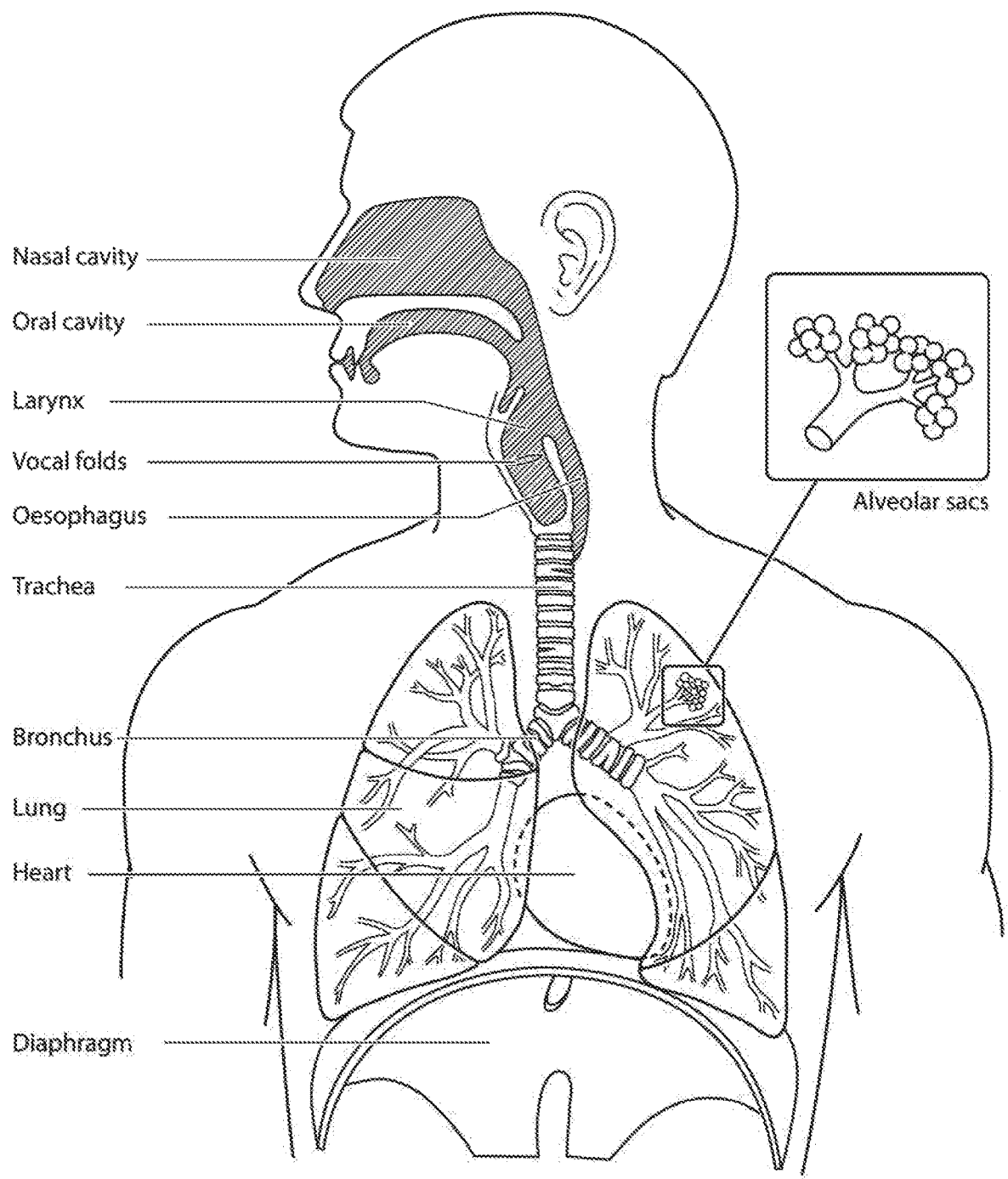

FIG. 2A shows an overview of a human respiratory system including the nasal and oral cavities, the larynx, vocal folds, oesophagus, trachea, bronchus, lung, alveolar sacs, heart and diaphragm.

Figure 2B:
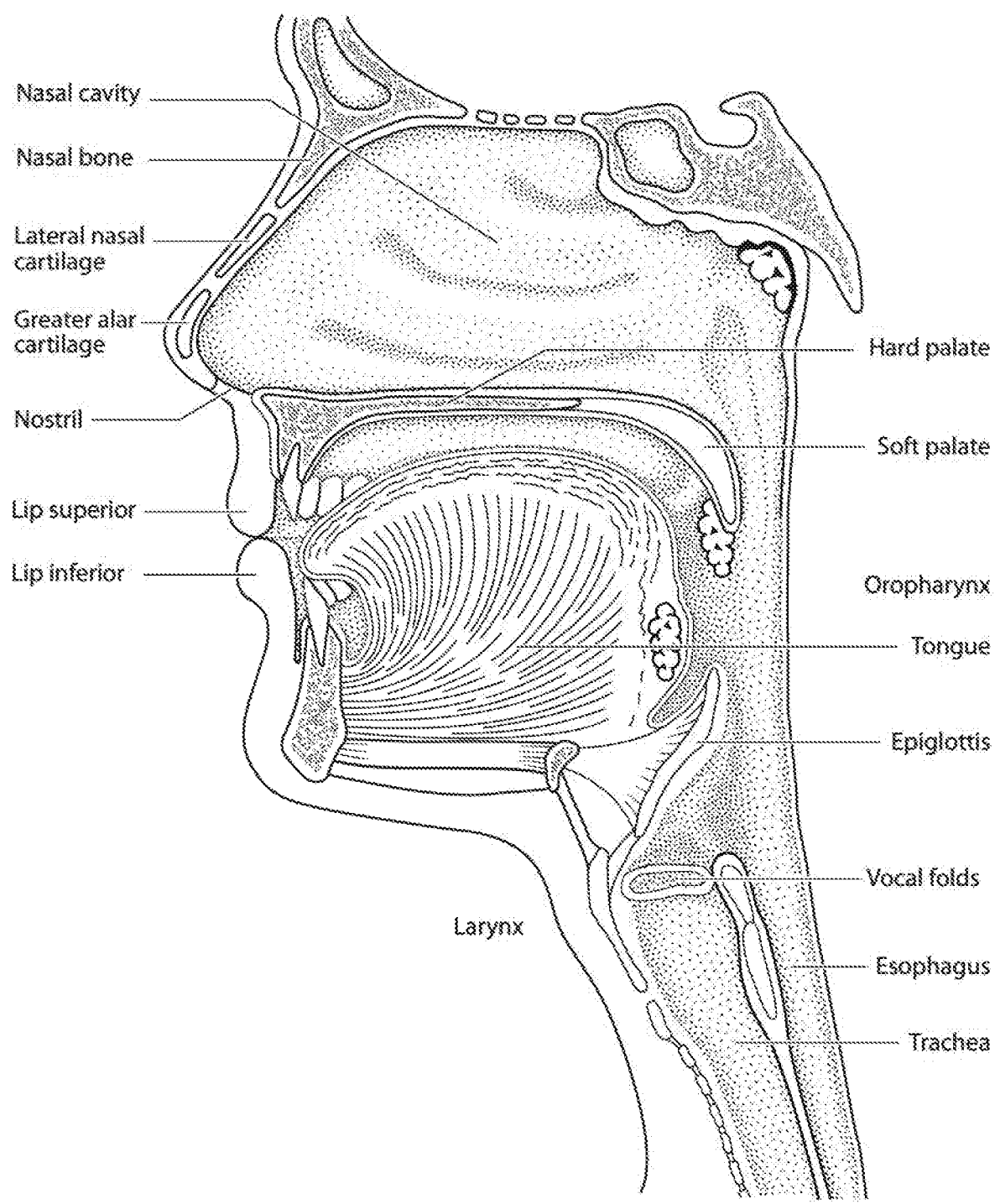

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
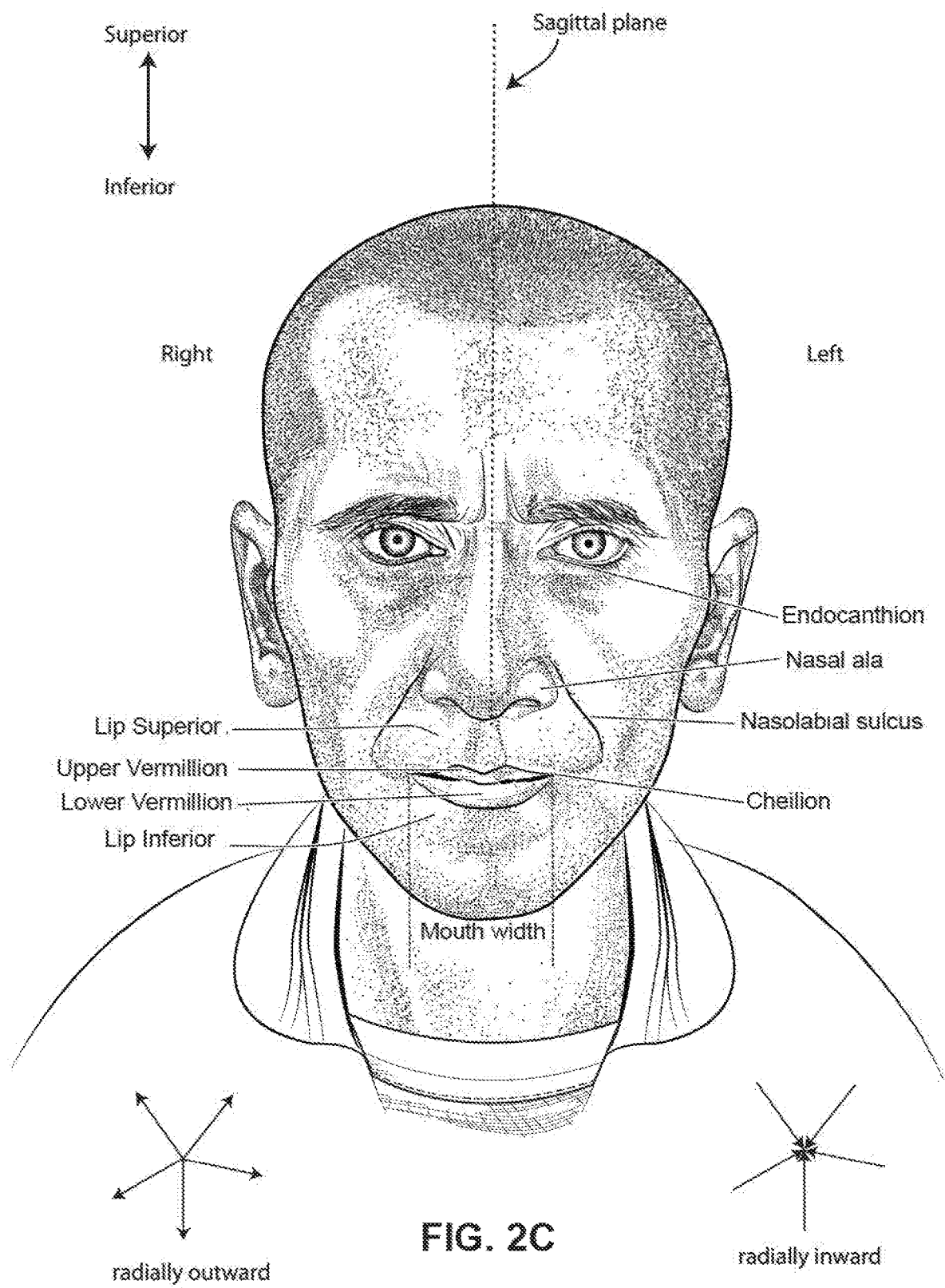

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
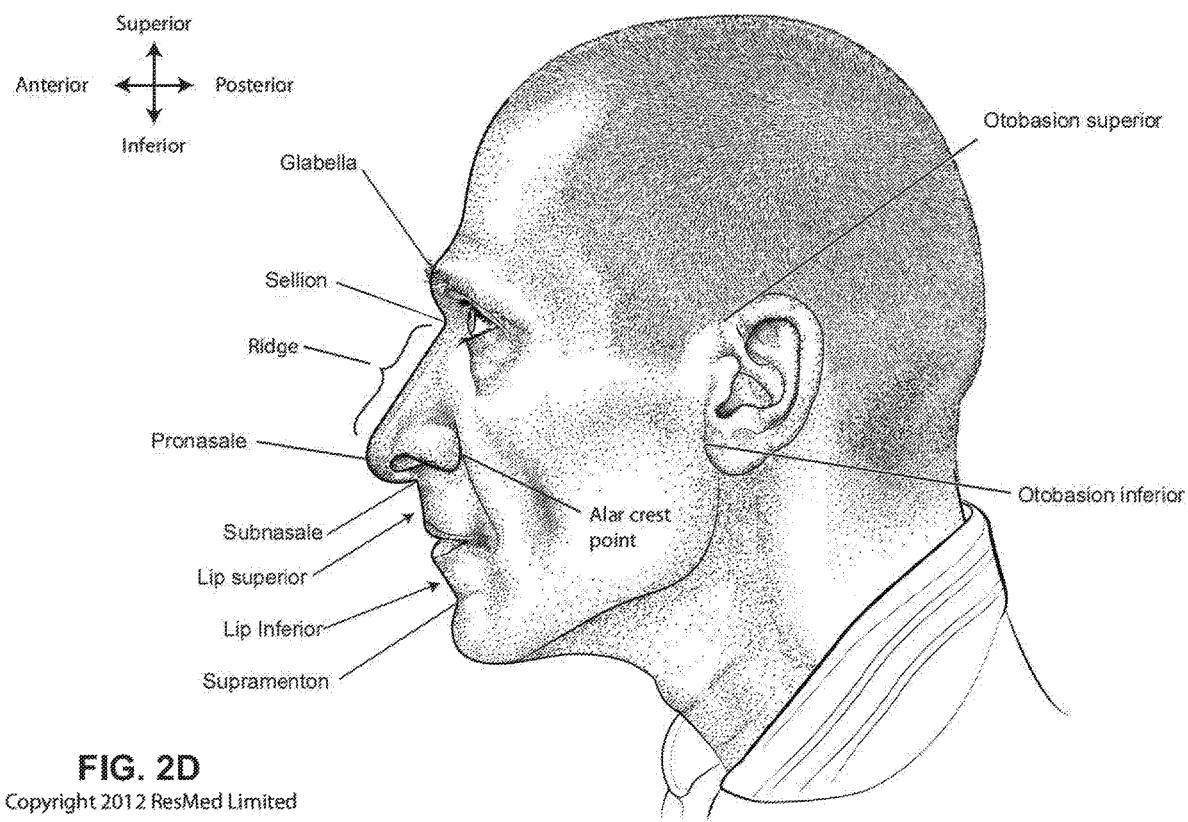

FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
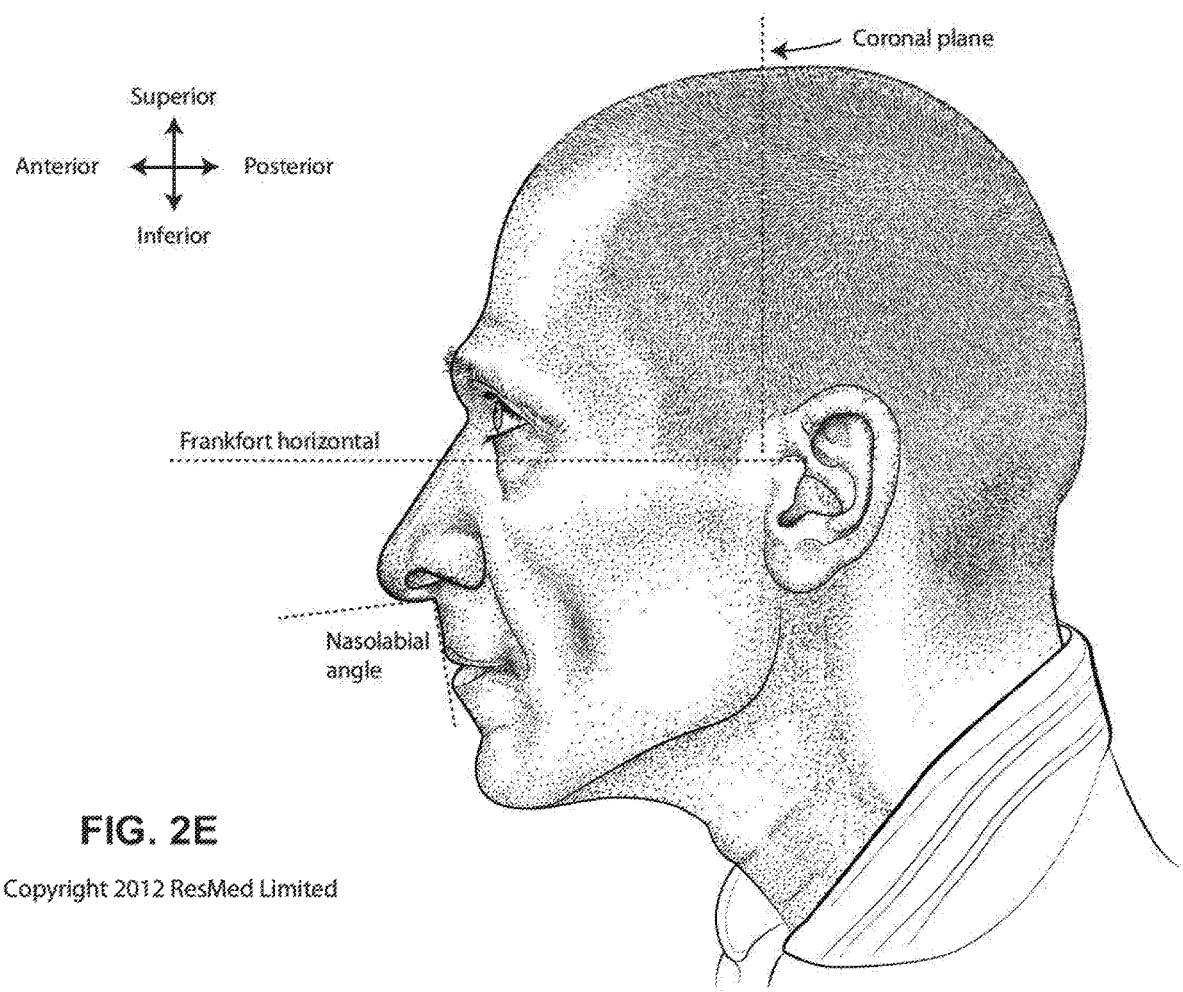

FIG. 2E is a further side view of a head. The approximate locations of the Frankfort horizontal and nasolabial angle are indicated. The coronal plane is also indicated.

Figure 2F:
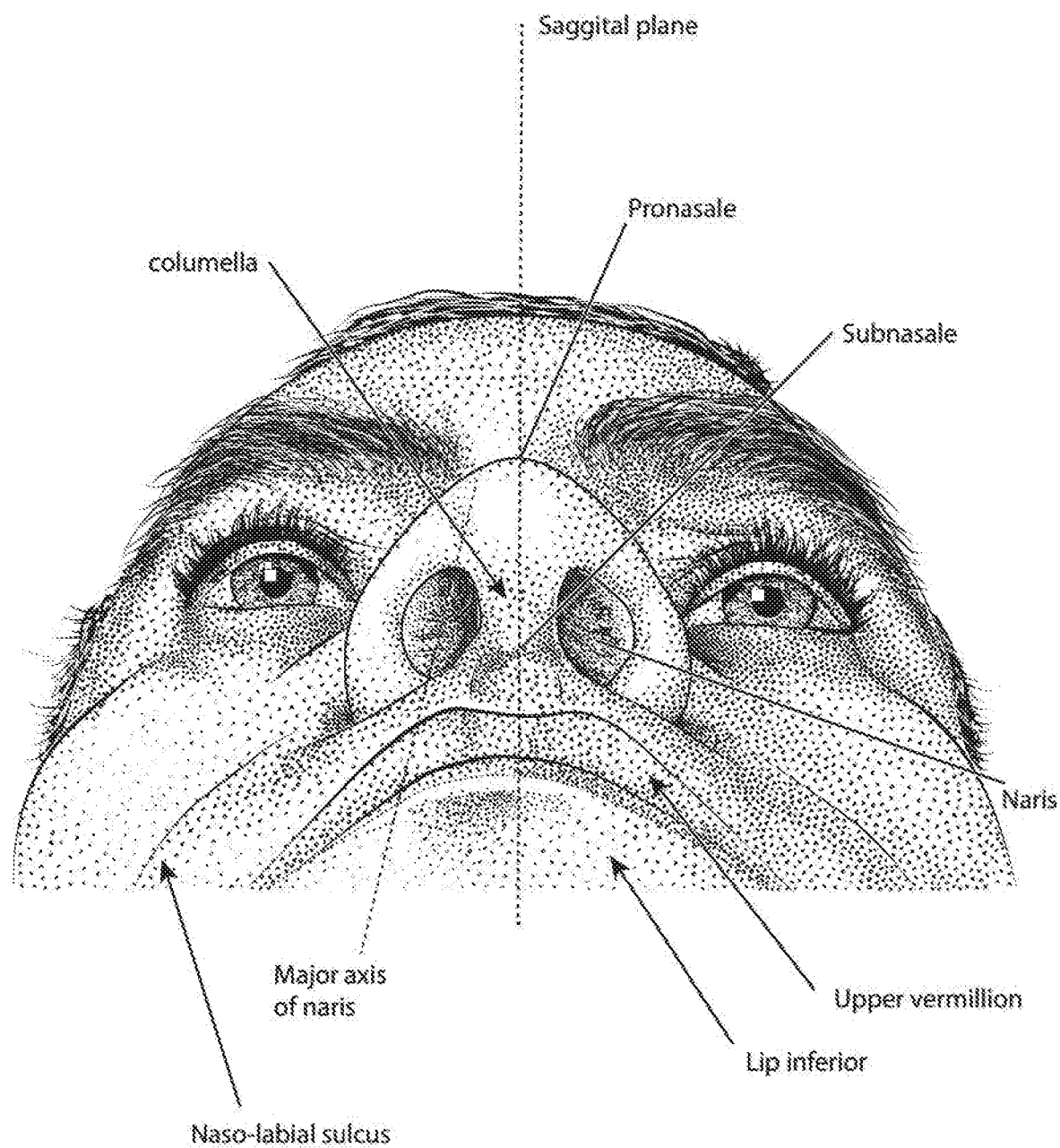

FIG. 2F shows a base view of a nose with several features identified including naso-labial sulcus, lip inferior, upper Vermilion, naris, subnasale, columella, pronasale, the major axis of a naris and the sagittal plane.

Figure 2G:
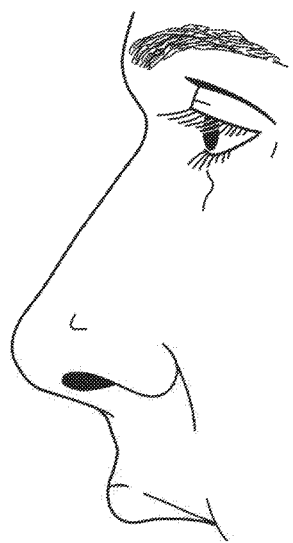

FIG. 2G shows a side view of the superficial features of a nose.

Figure 2H:
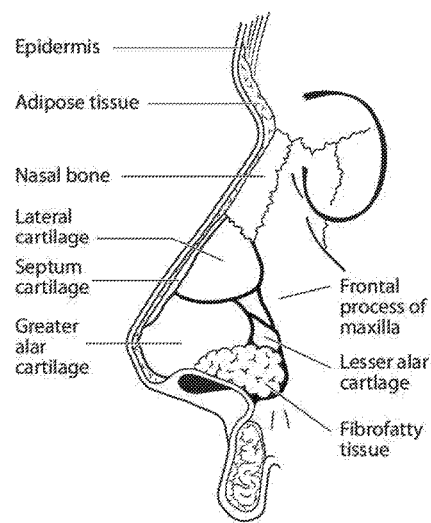

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

Figure 2I:
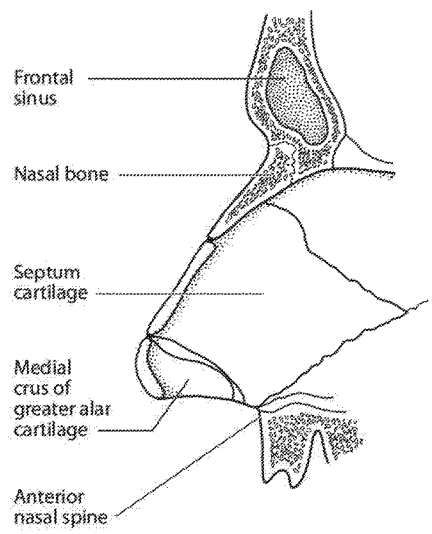

FIG. 2I shows a medial dissection of a nose, approximately several millimeters from a sagittal plane, amongst other things showing the septum cartilage and medial crus of greater alar cartilage.

Figures 2J, 2K:
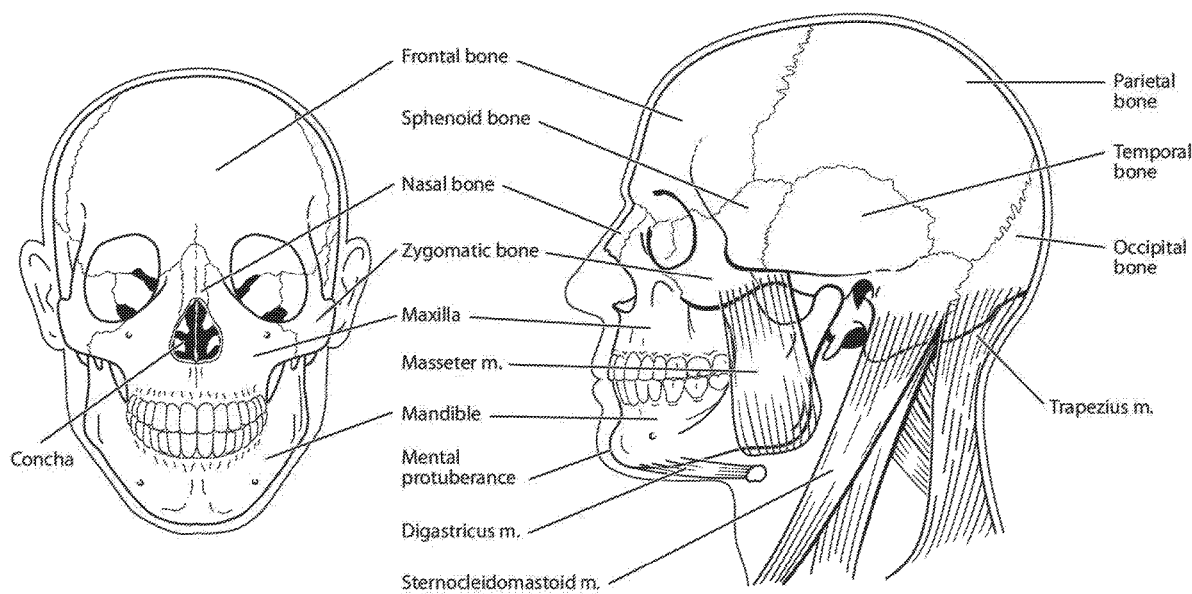

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
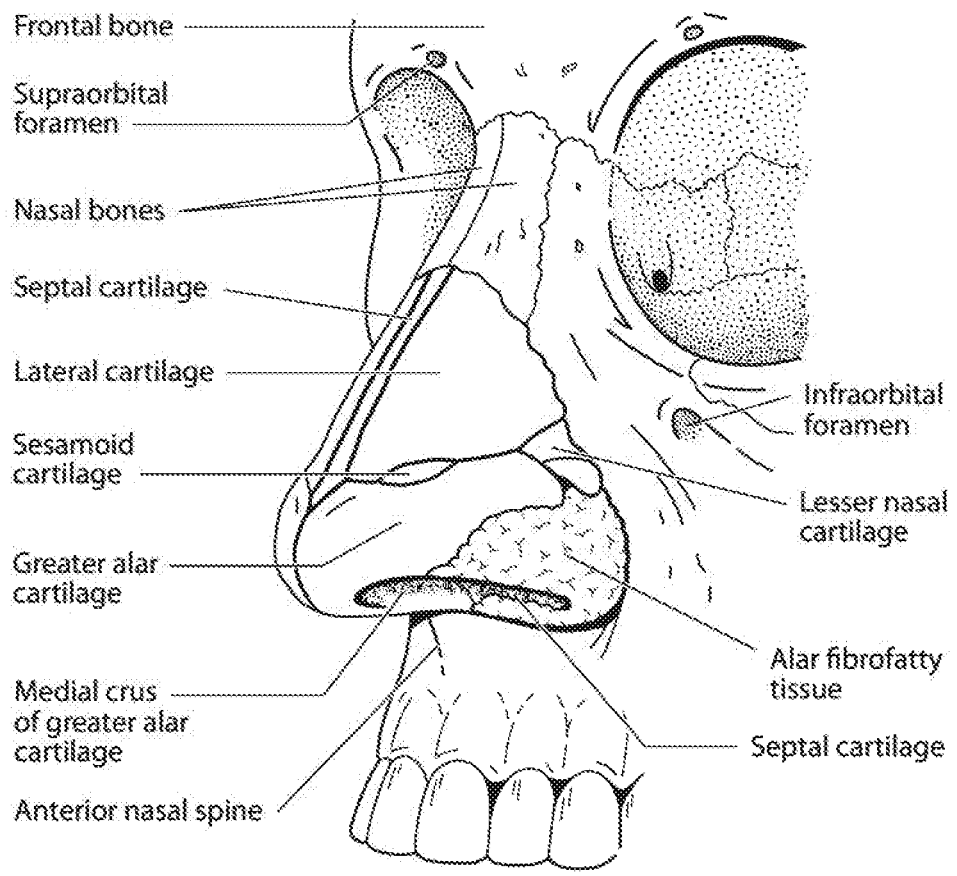

FIG. 2L shows an anterolateral view of a nose.

3.3 Patient Interface

Figure 3A:
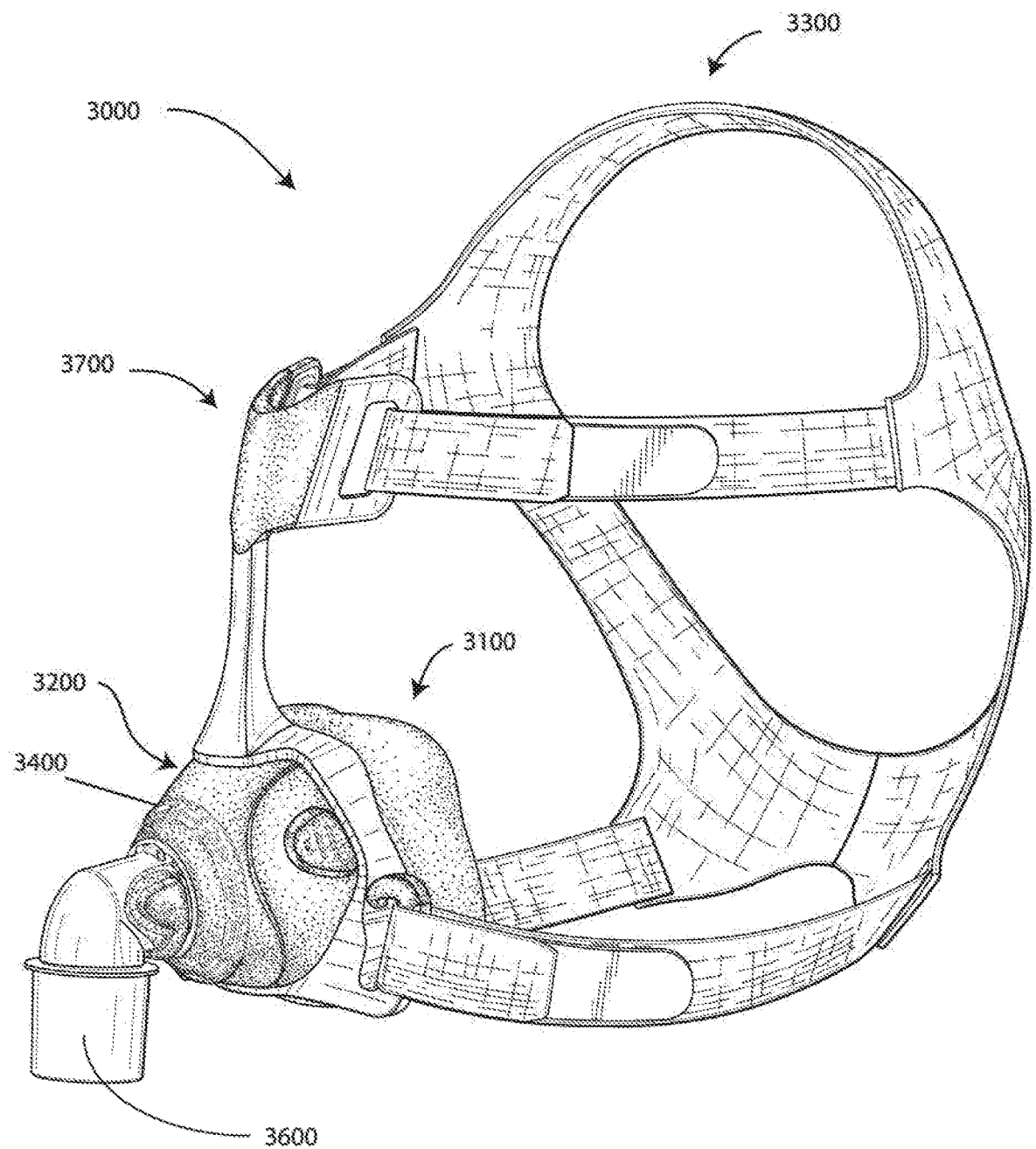

FIG. 3A shows a patient interface in the form of a nasal mask in accordance with one form of the present technology.

Figure 3B:
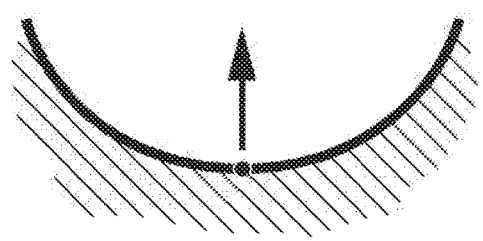

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
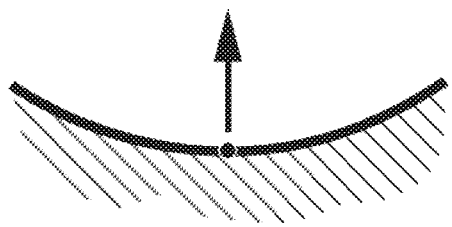

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
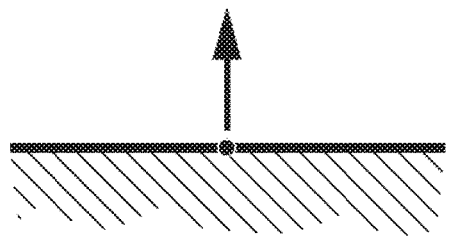

FIG. 3D shows a schematic of a cross-section through a structure at a point. An outward normal at the point is indicated. The curvature at the point has a value of zero.

Figure 3E:
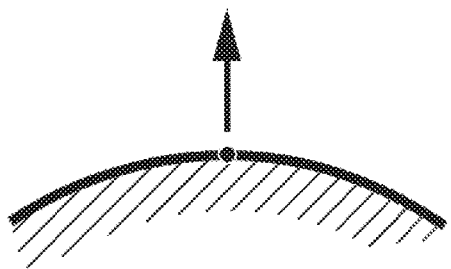

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
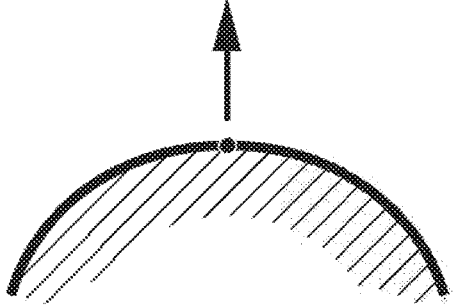

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3G:
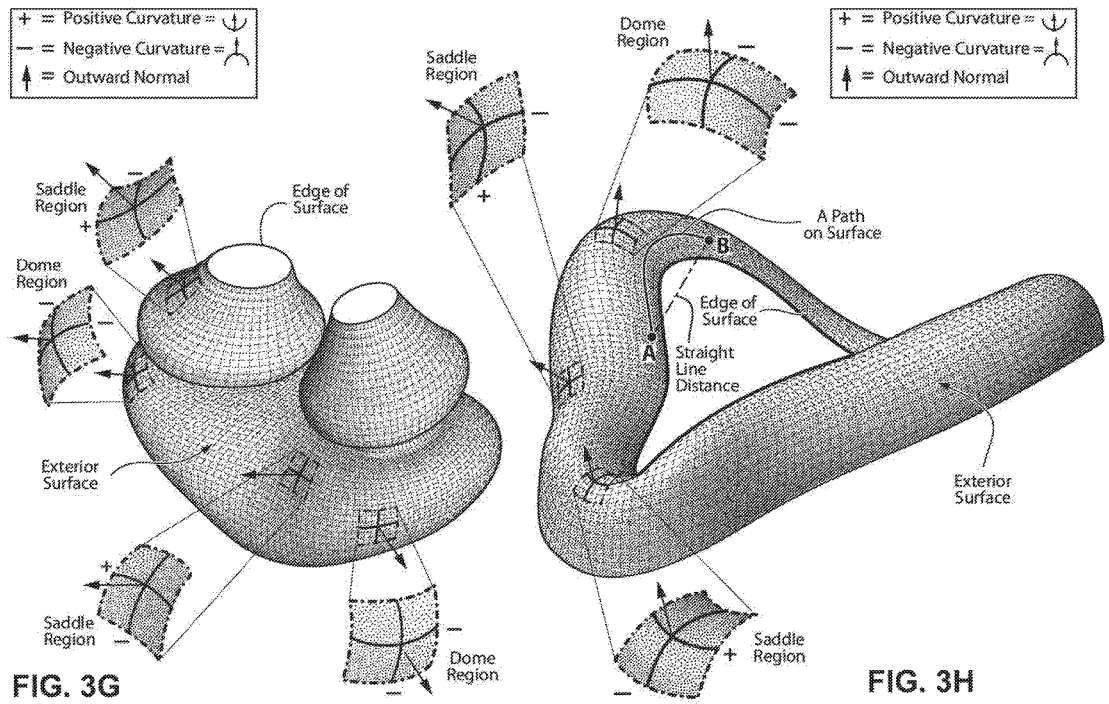

FIG. 3G shows a cushion for a mask that includes two pillows. An exterior surface of the cushion is indicated. An edge of the surface is indicated. Dome and saddle regions are indicated.

Figure 3H:
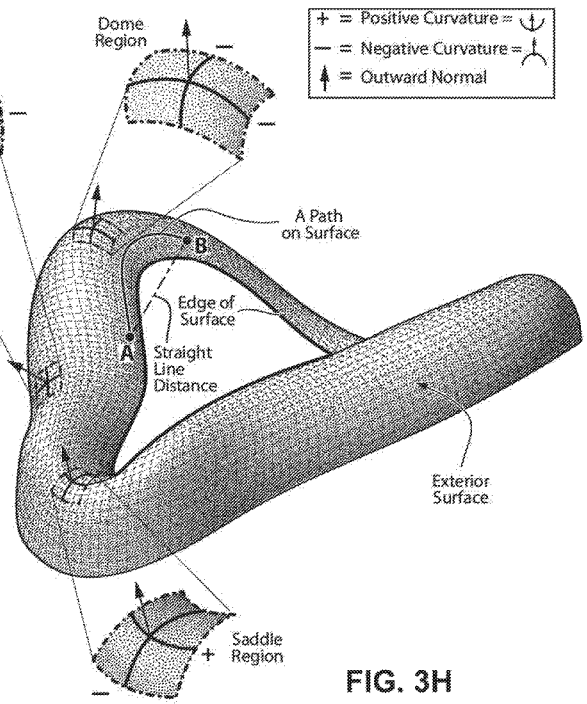

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
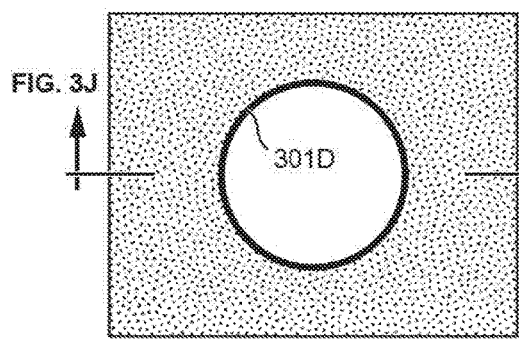

FIG. 3I shows the surface of a structure, with a one dimensional hole in the surface. Plane curve 301D forms the boundary of a one dimensional hole.

Figure 3K:
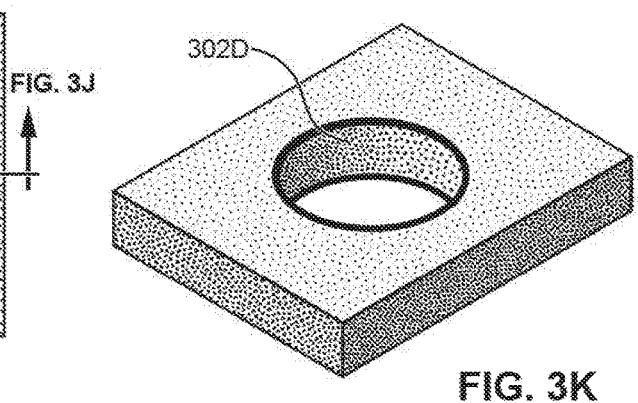
Figure 3J:
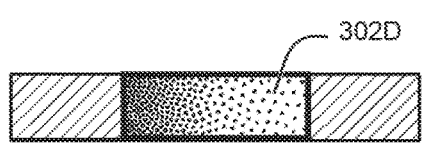

FIG. 3J shows a cross-section through the structure of FIG. 3I. Surface 302D that bounds a two dimensional hole in the structure of FIG. 3I is indicated.

FIG. 3K shows a perspective view of the structure of FIG. 3I, including the two dimensional hole and the one dimensional hole. Surface 302D that bounds a two dimensional hole in the structure of FIG. 3I is indicated.

Figure 3L:
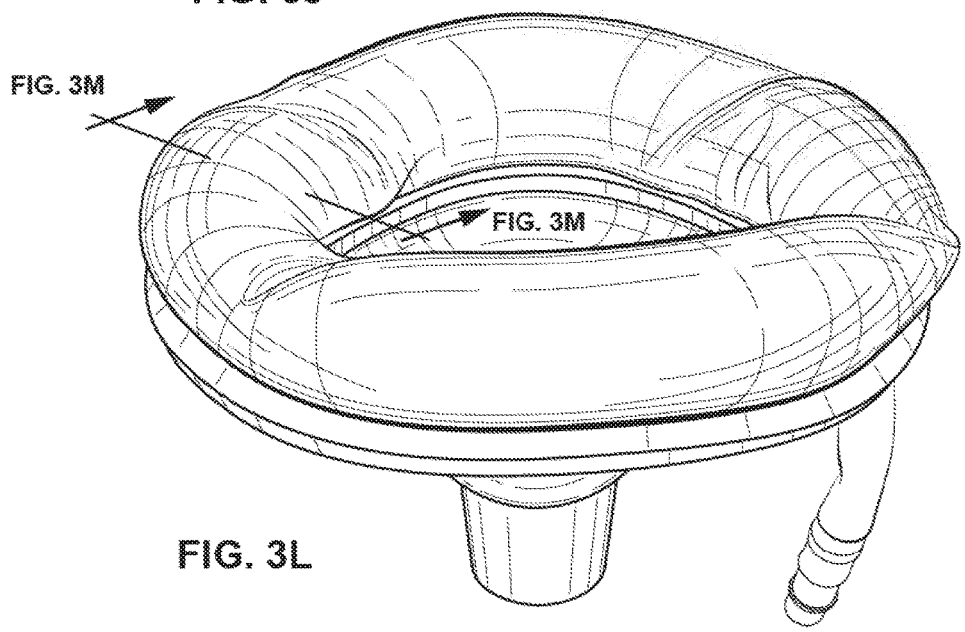

FIG. 3L shows a mask having an inflatable bladder as a cushion.

Figure 3M:
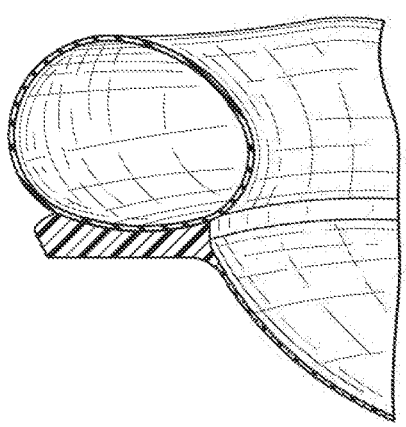

FIG. 3M shows a cross-section through the mask of FIG. 3L, and shows the inside surface of the bladder.

Figure 3N:
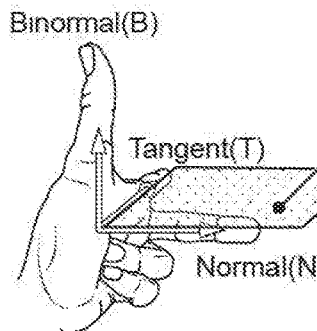

FIG. 3N illustrates a left-hand rule.

Figure 3O:
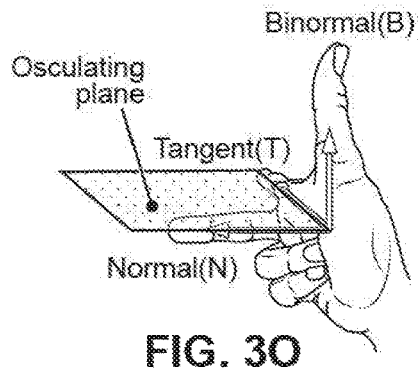

FIG. 3O illustrates a right-hand rule.

Figure 3P:
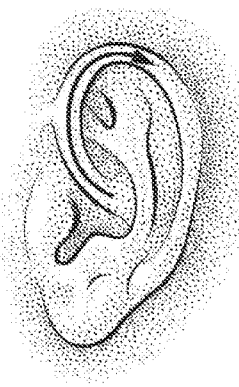

FIG. 3P shows a left ear, including a left ear helix.

Figure 3R:
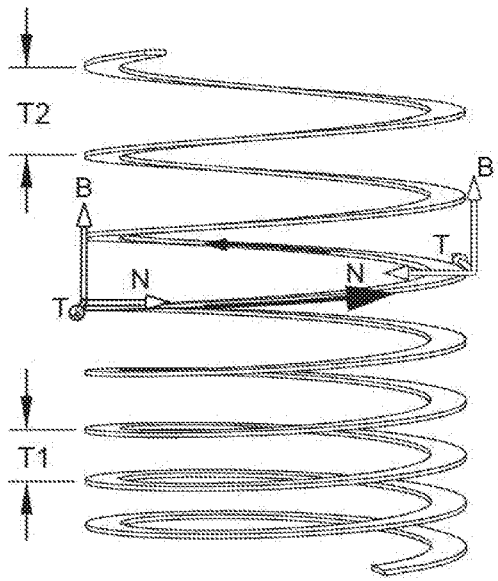
Figure 3Q:
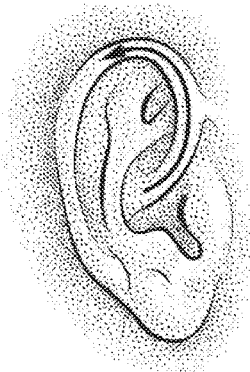

FIG. 3Q shows a right ear, including a right ear helix.

FIG. 3R shows a right-hand helix.

Figure 3S:
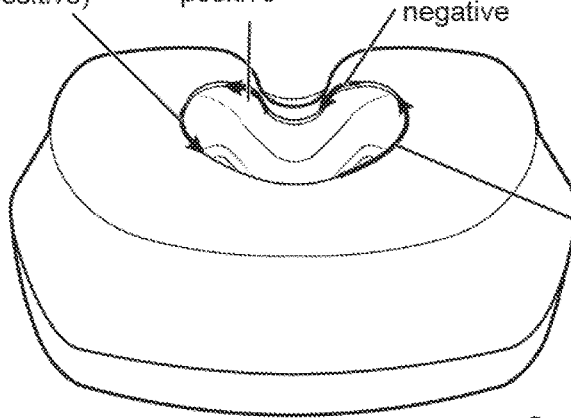

FIG. 3S shows a view of a mask, including the sign of the torsion of the space curve defined by the edge of the sealing membrane in different regions of the mask.

Figure 4:
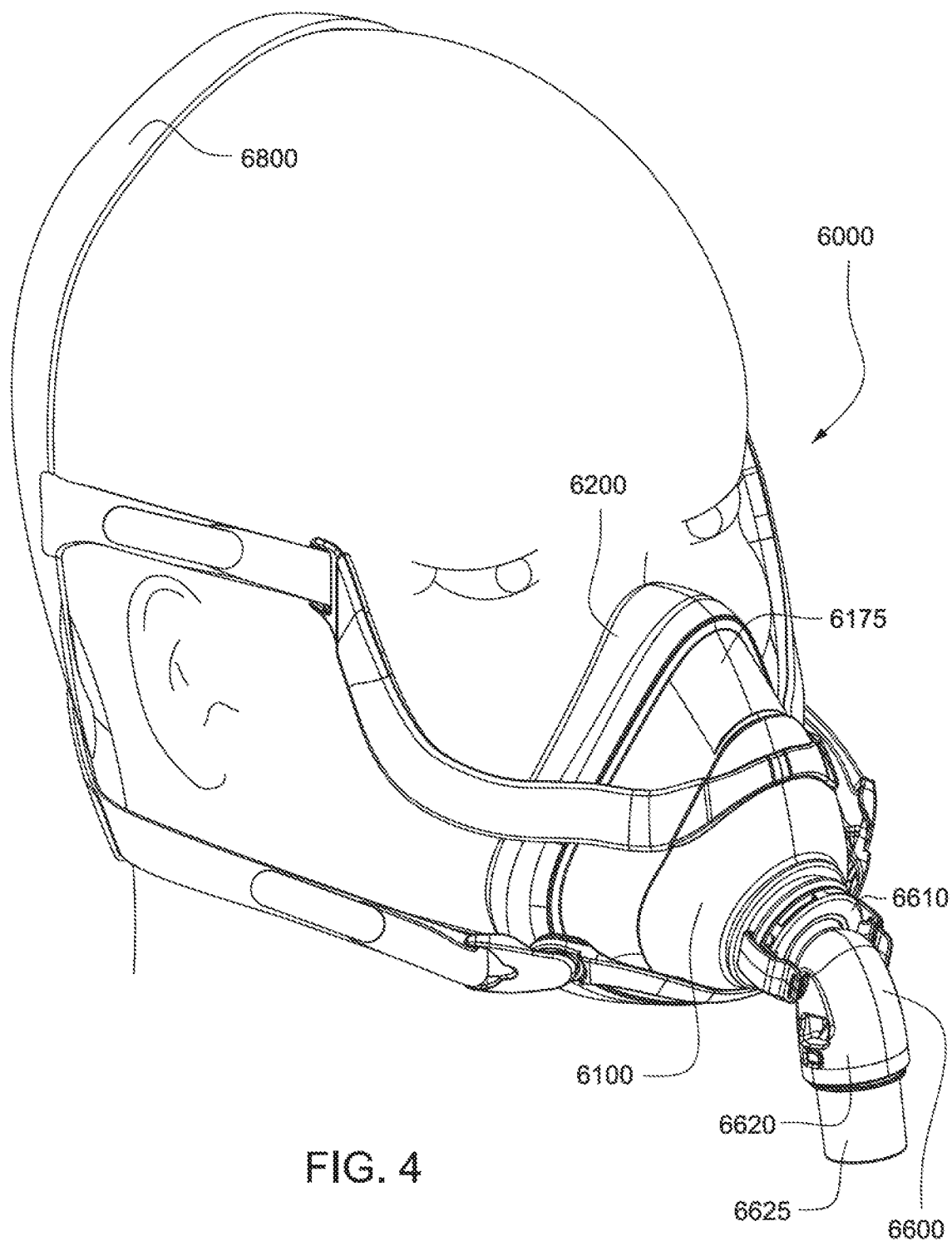

FIG. 4 is a perspective view of a patient interface shown on a patient's head including an elbow assembly according to an example of the present technology.

Figure 5:
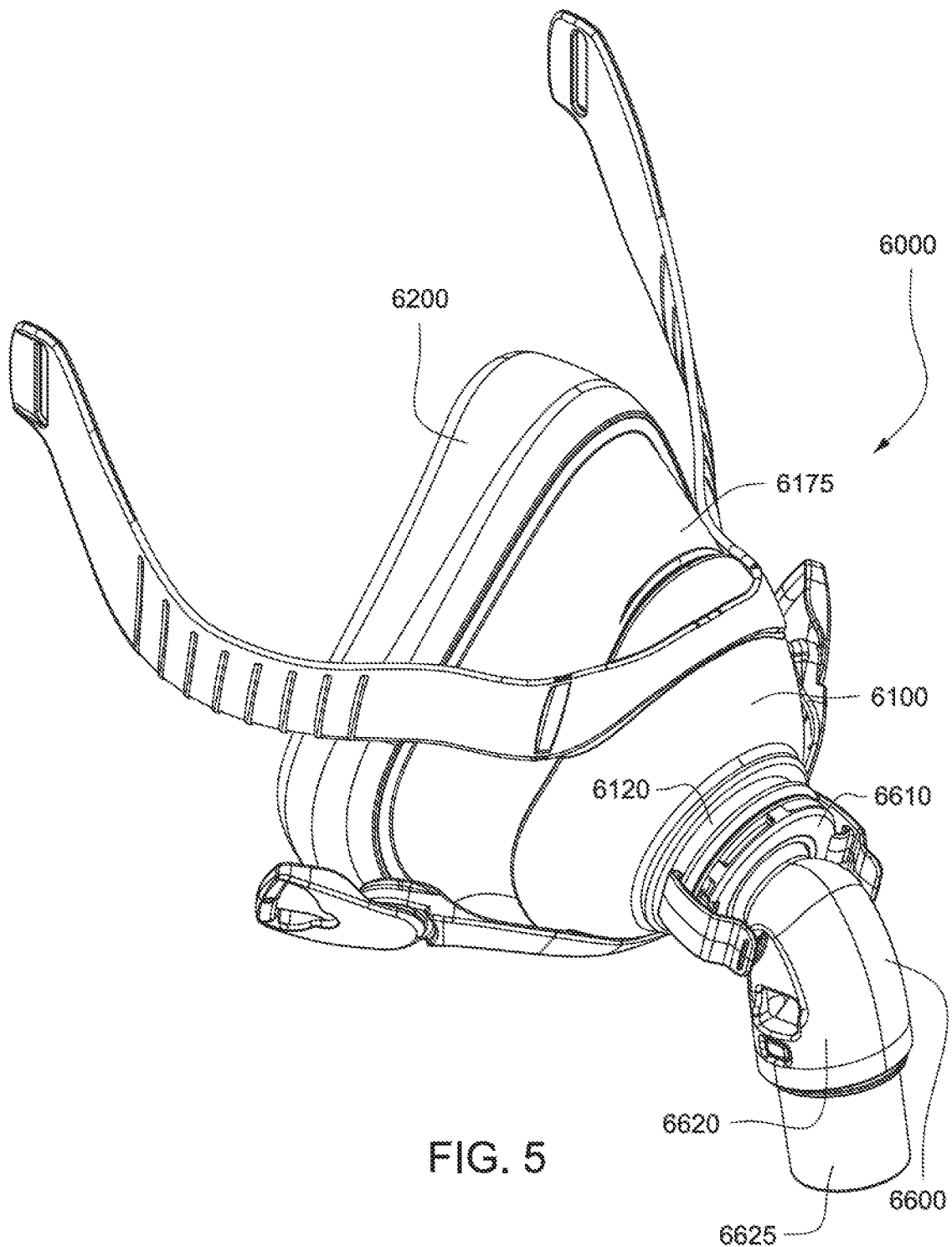

FIG. 5 is a perspective view of the patient interface shown in FIG. 4 with the headgear removed.

Figure 6:
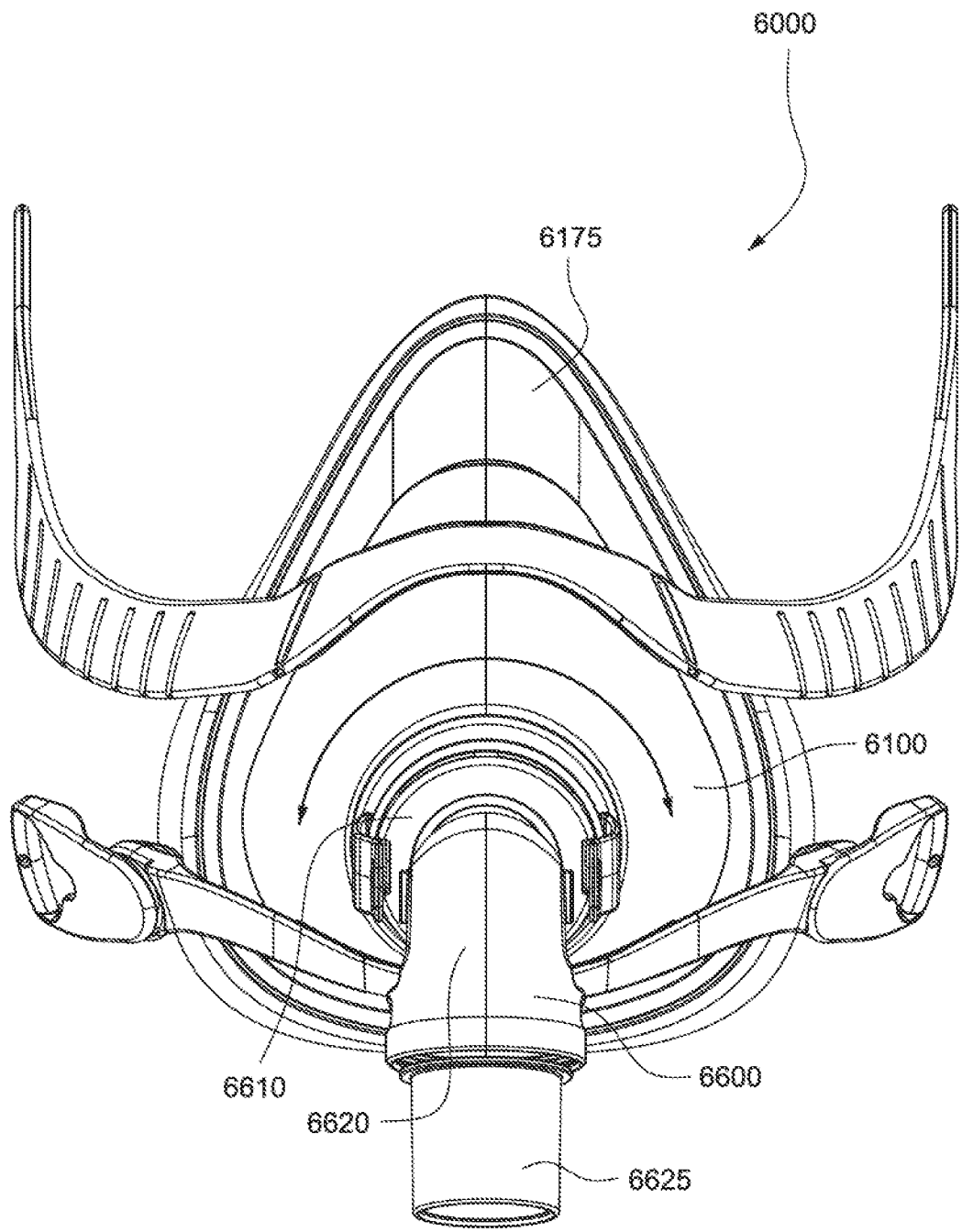

FIG. 6 is a front view of the patient interface shown in FIG. 5.

Figure 7:
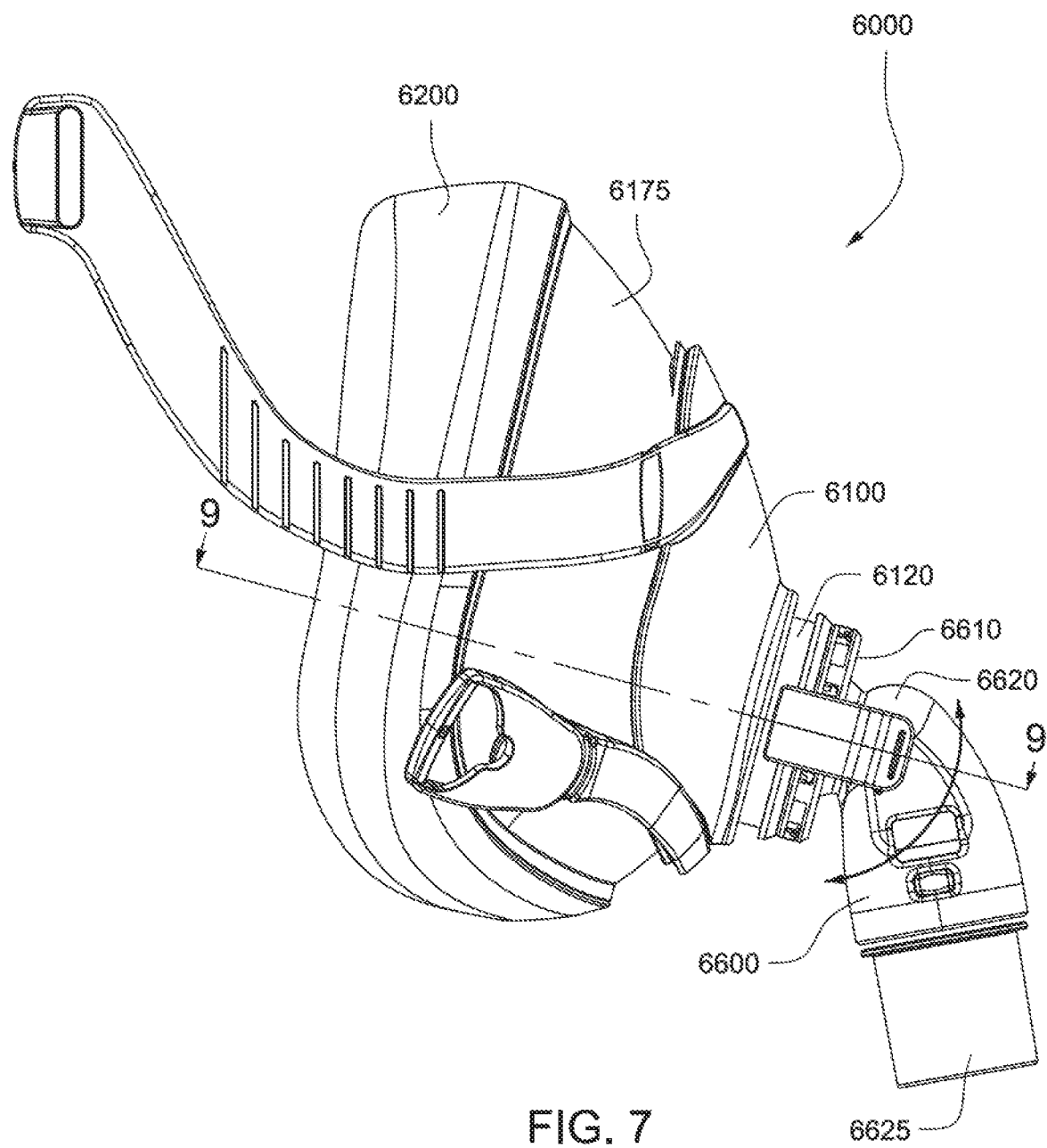

FIG. 7 is a side view of the patient interface shown in FIG. 5.

Figure 8:
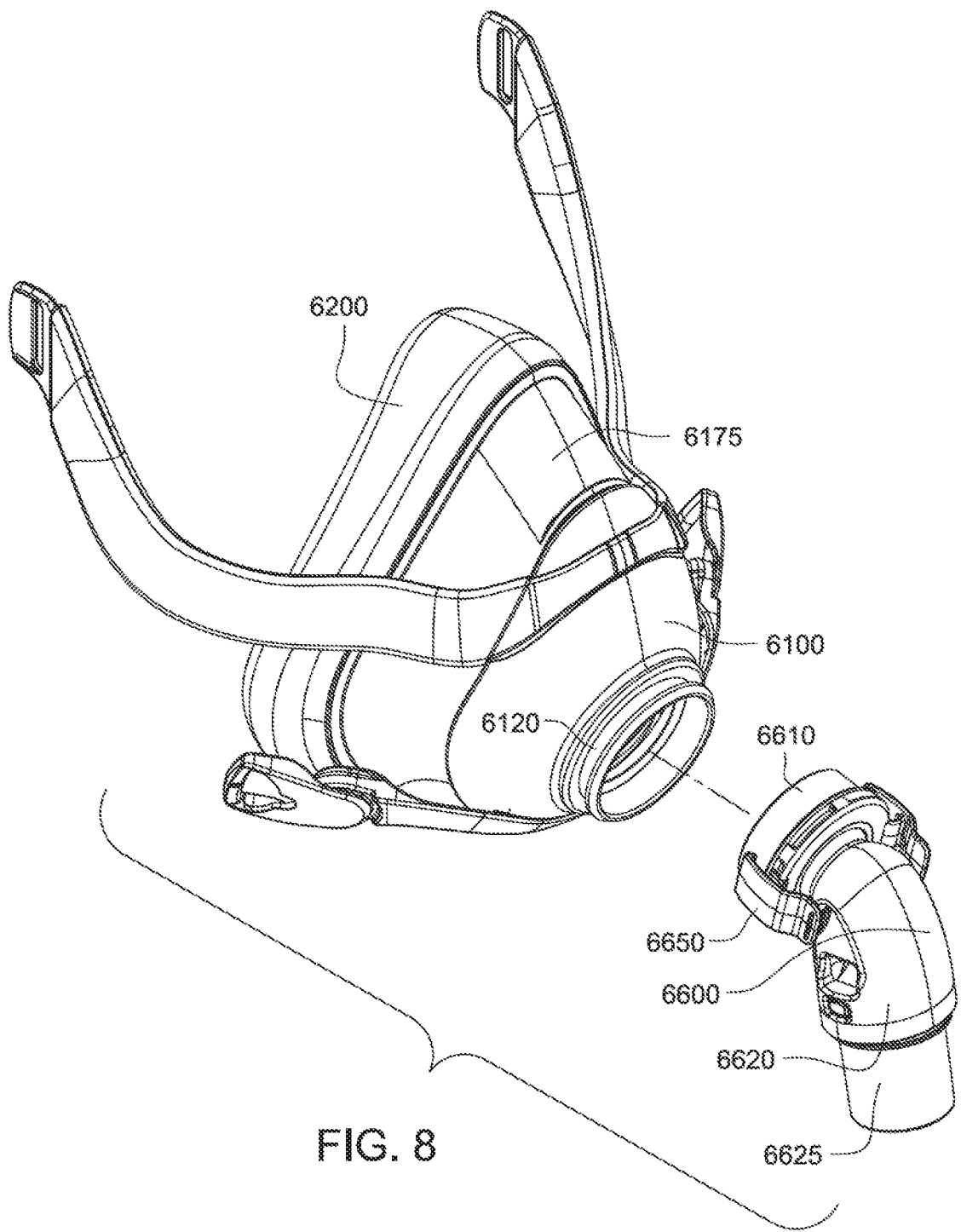

FIG. 8 is an exploded view of the patient interface of FIG. 5 showing the cushion assembly and frame assembly removably connected with the elbow assembly removed.

Figure 9:
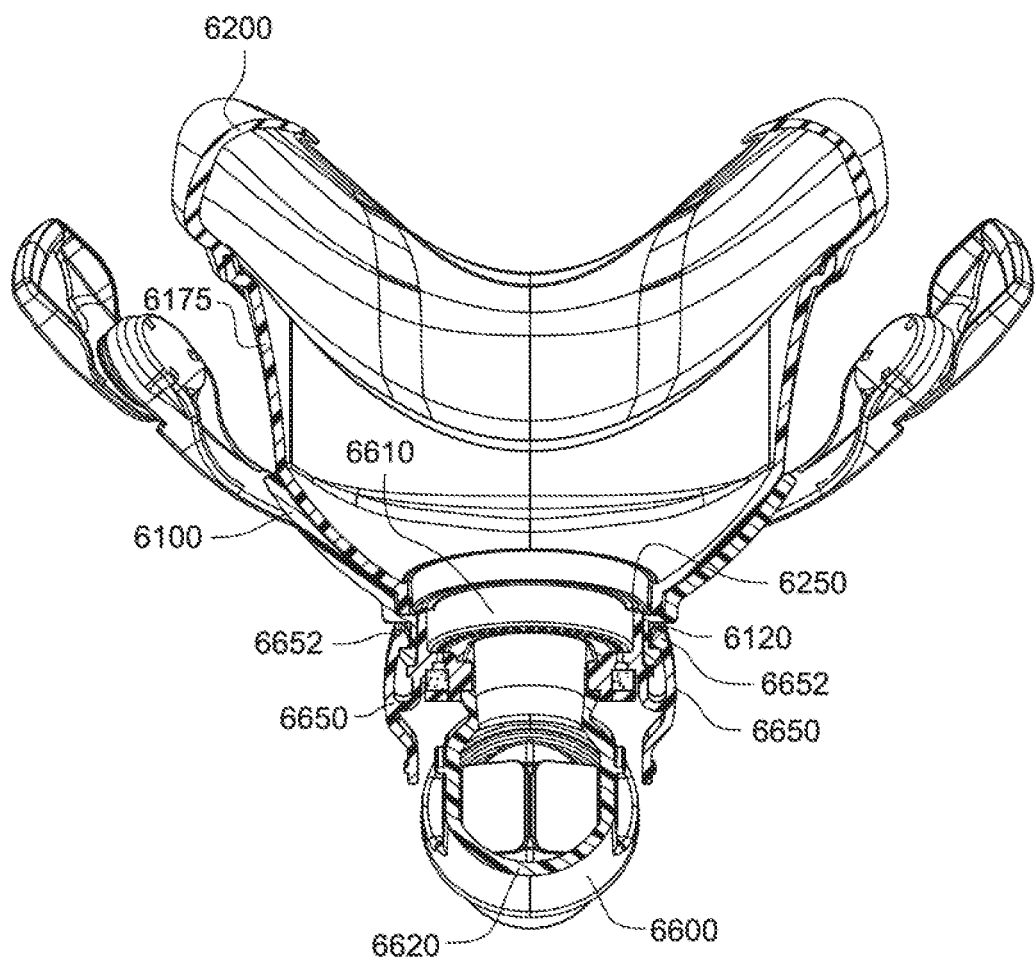

FIG. 9 is a cross-sectional view of the patient interface shown in FIG. 7.

Figure 10:
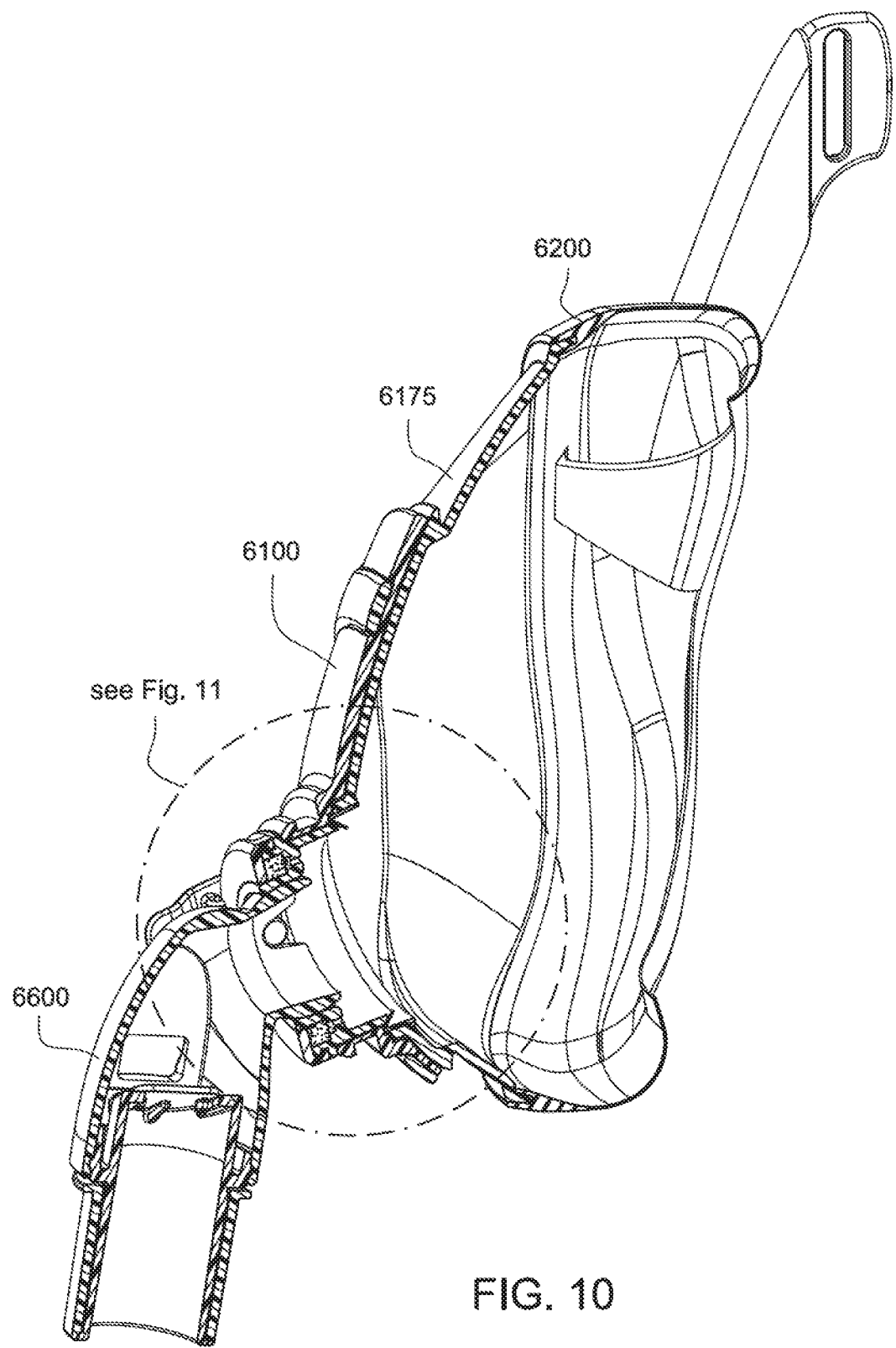

FIG. 10 is a cross-sectional view of the patient interface shown in FIG. 5.

Figure 11:
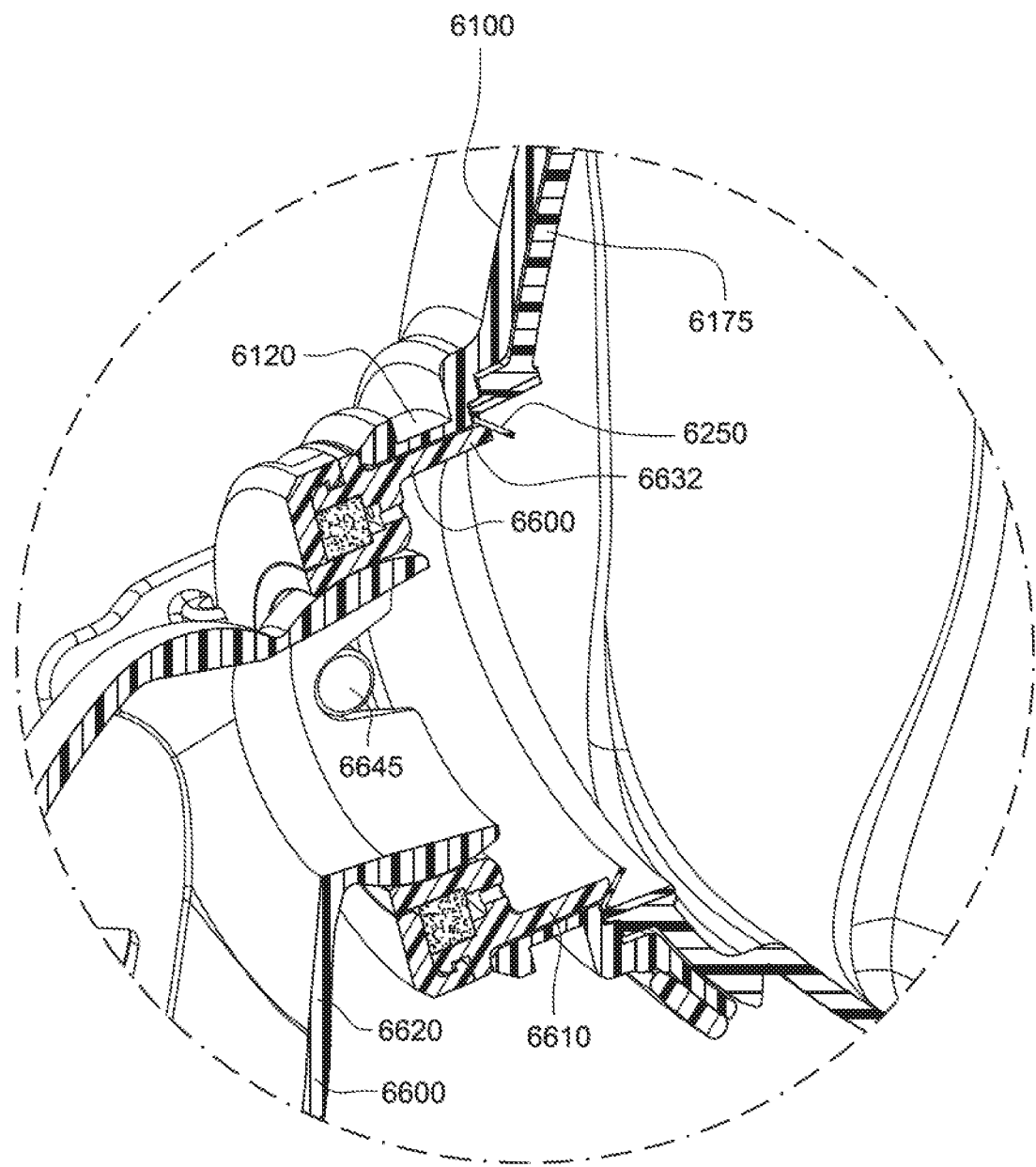

FIG. 11 is an enlarged view of the patient interface shown in FIG. 10.

Figure 12:
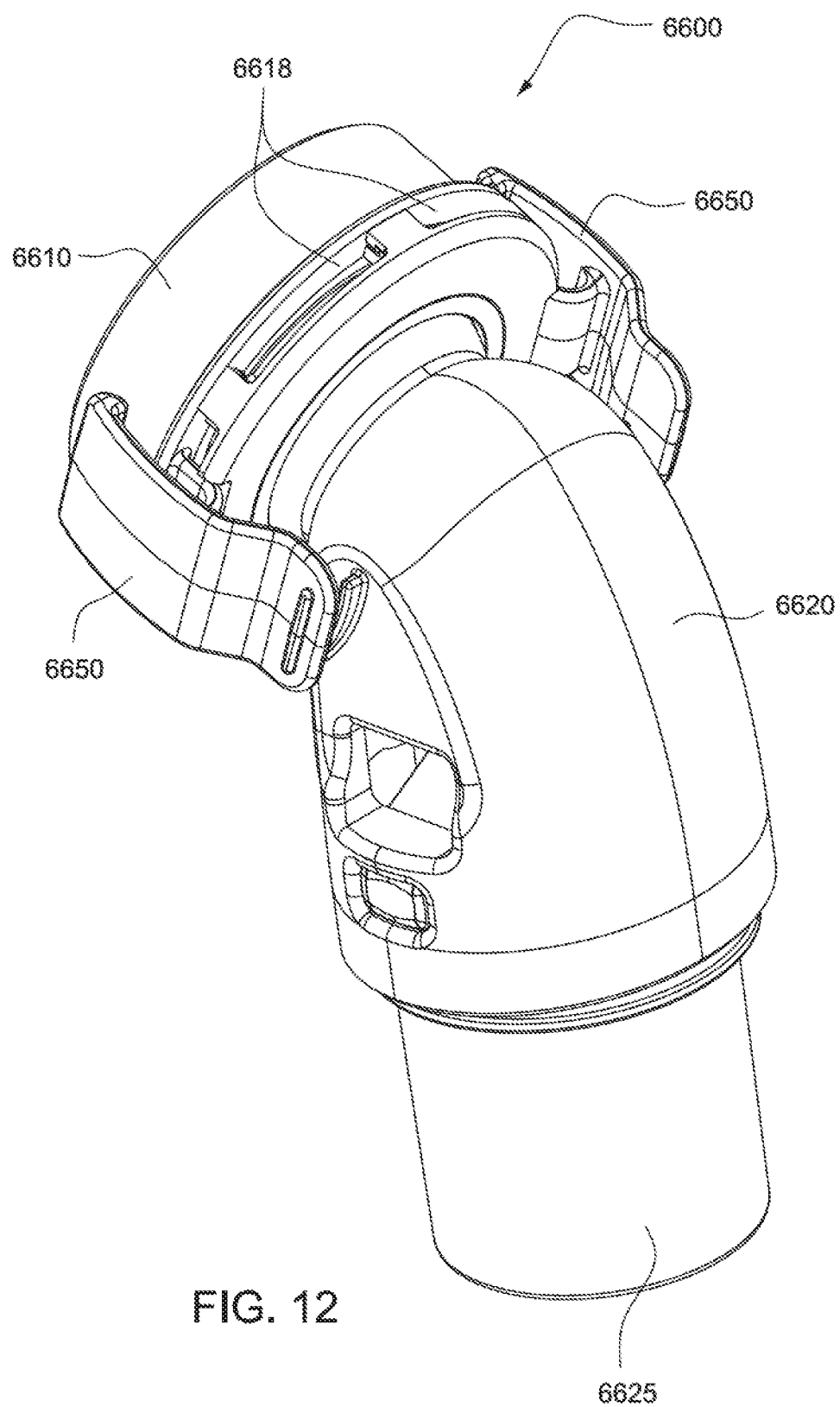

FIG. 12 is a front perspective view of an elbow assembly according to an example of the present technology.

Figure 13:
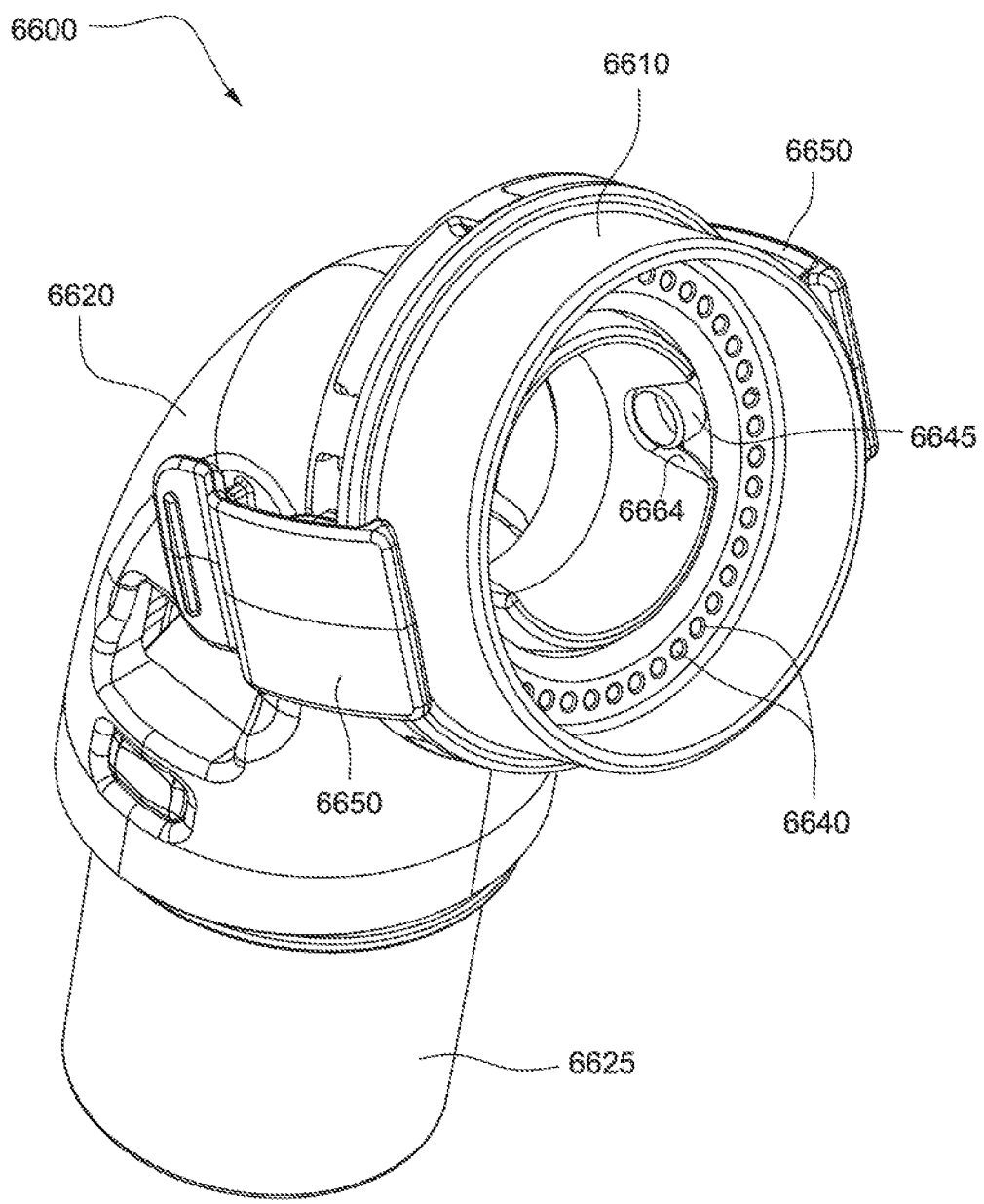

FIG. 13 is a rear perspective view of the elbow assembly shown in FIG. 12.

Figure 14:
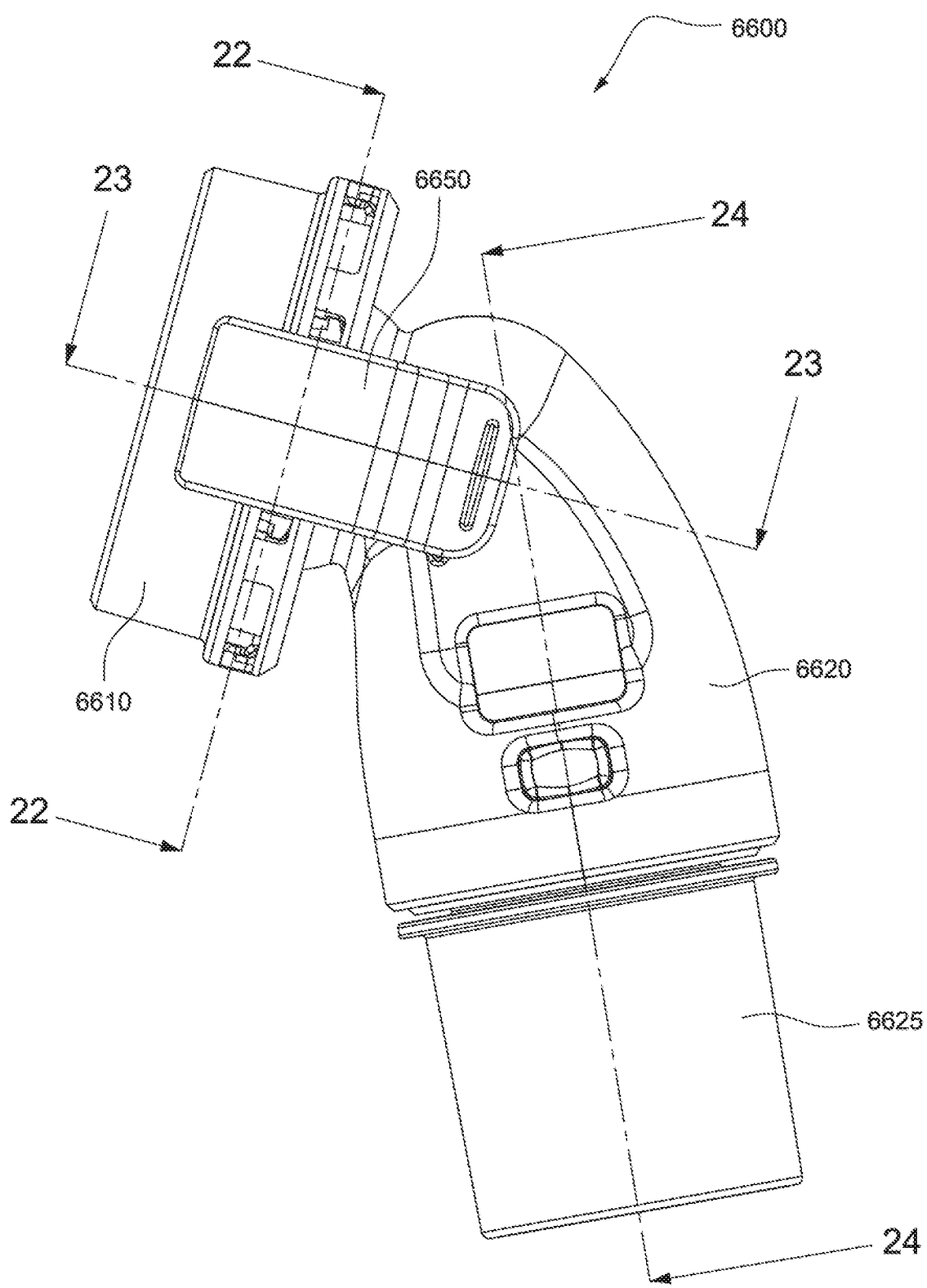

FIG. 14 is a side view of the elbow assembly shown in FIG. 12.

Figure 15:
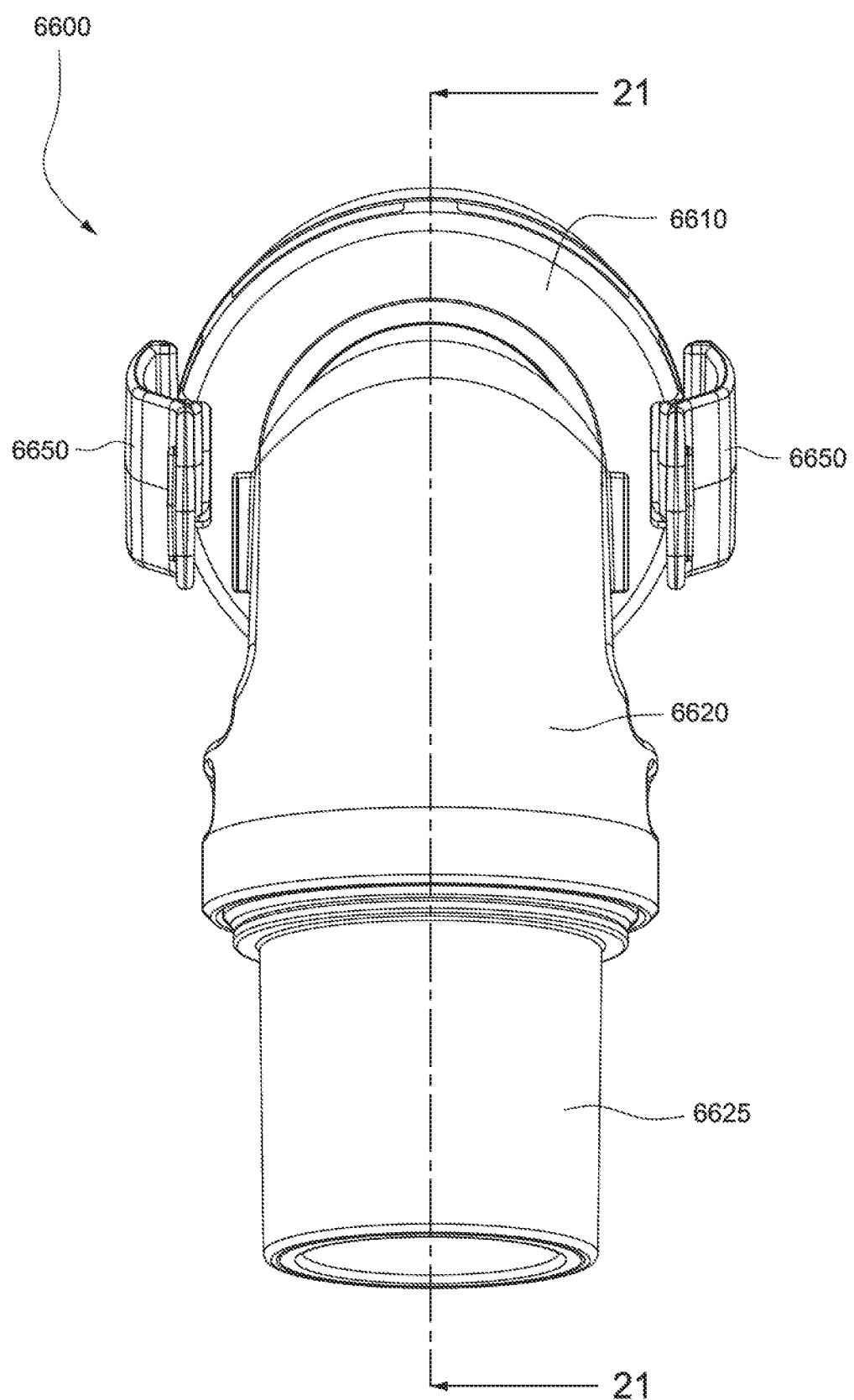

FIG. 15 is a front view of the elbow assembly shown in FIG. 12.

Figure 16:
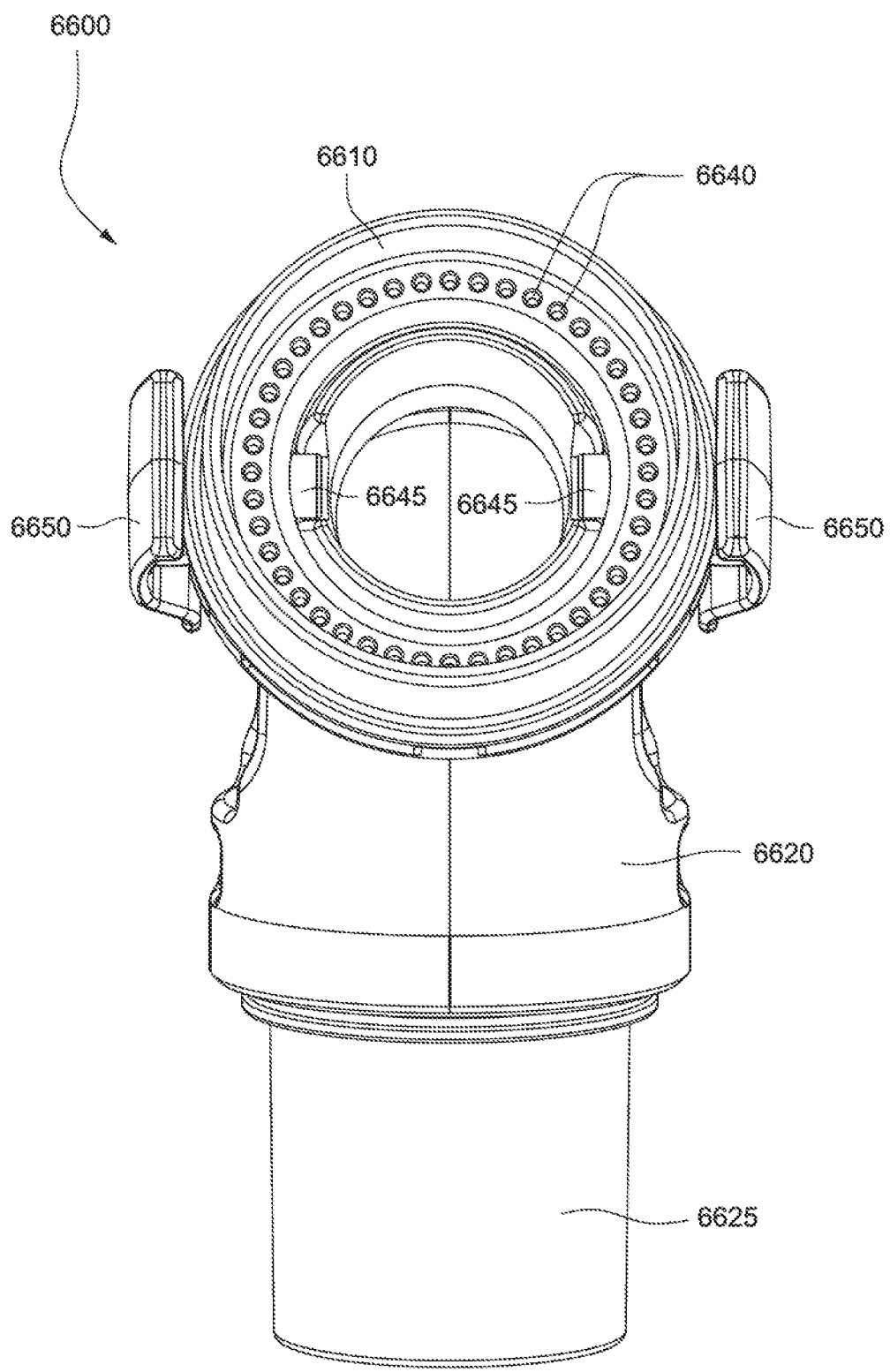

FIG. 16 is a rear view of the elbow assembly shown in FIG. 12.

Figure 17:
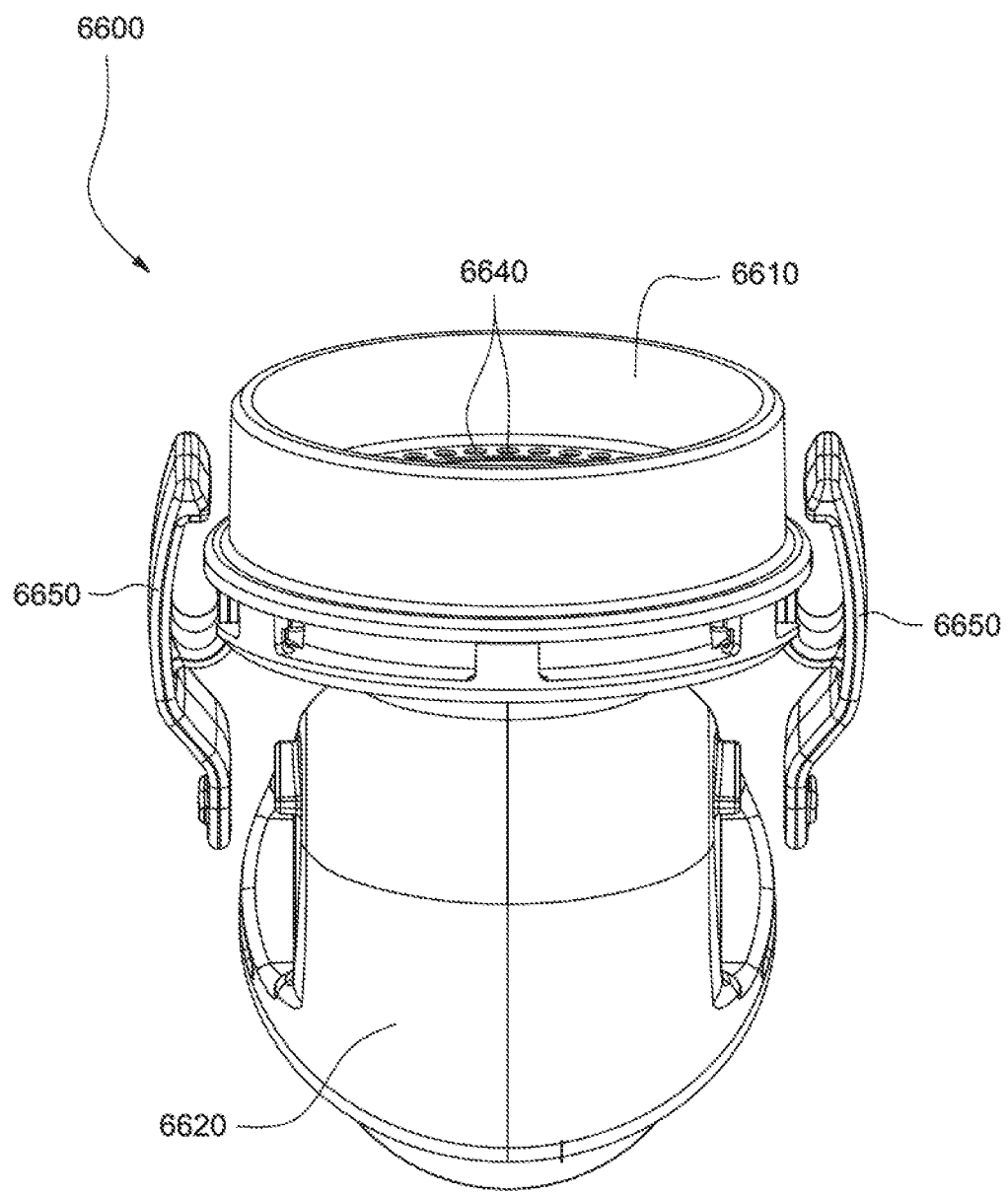

FIG. 17 is a top view of the elbow assembly shown in FIG. 12.

Figure 18:
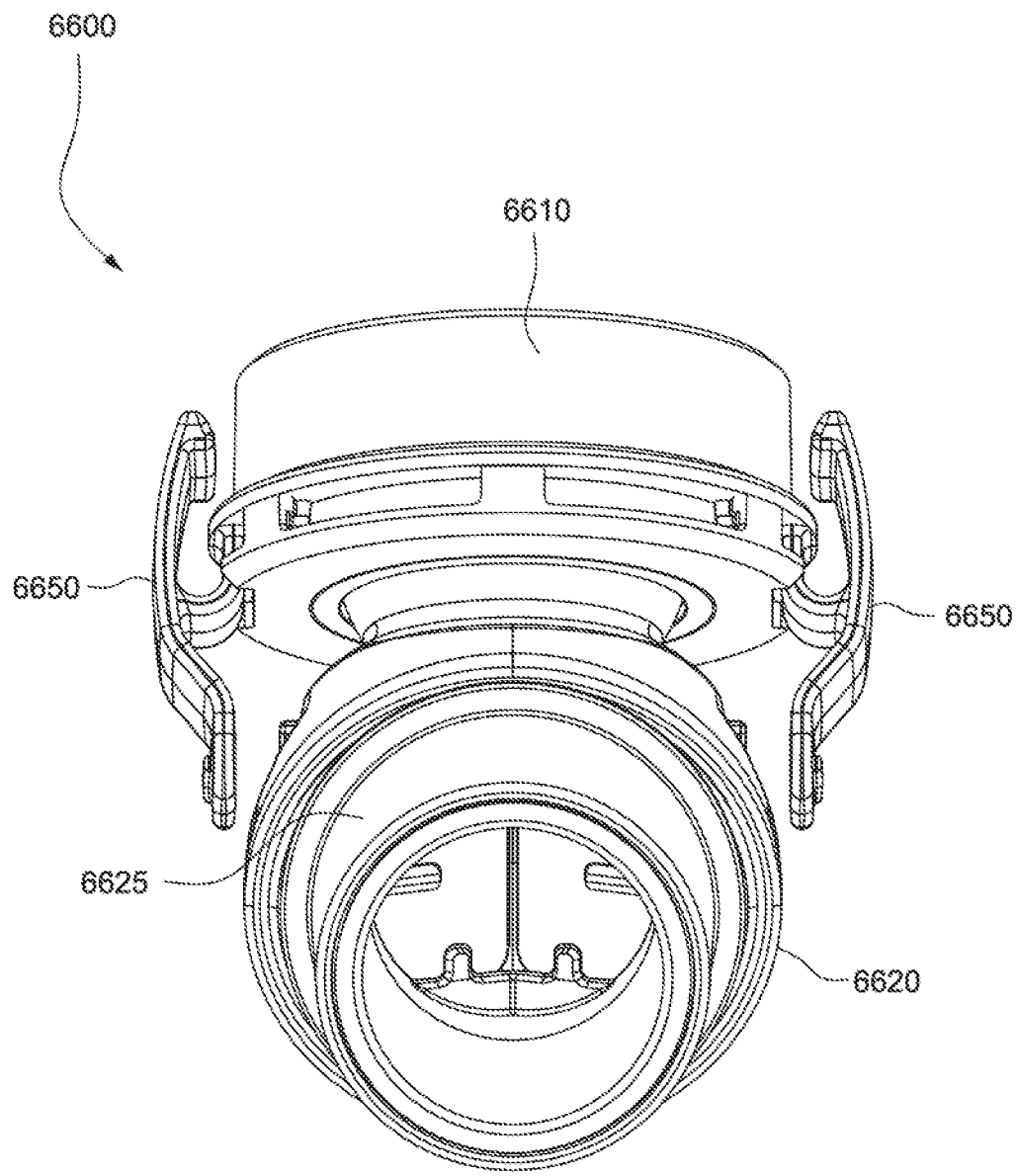

FIG. 18 is a bottom view of the elbow assembly shown in FIG. 12.

Figure 19:
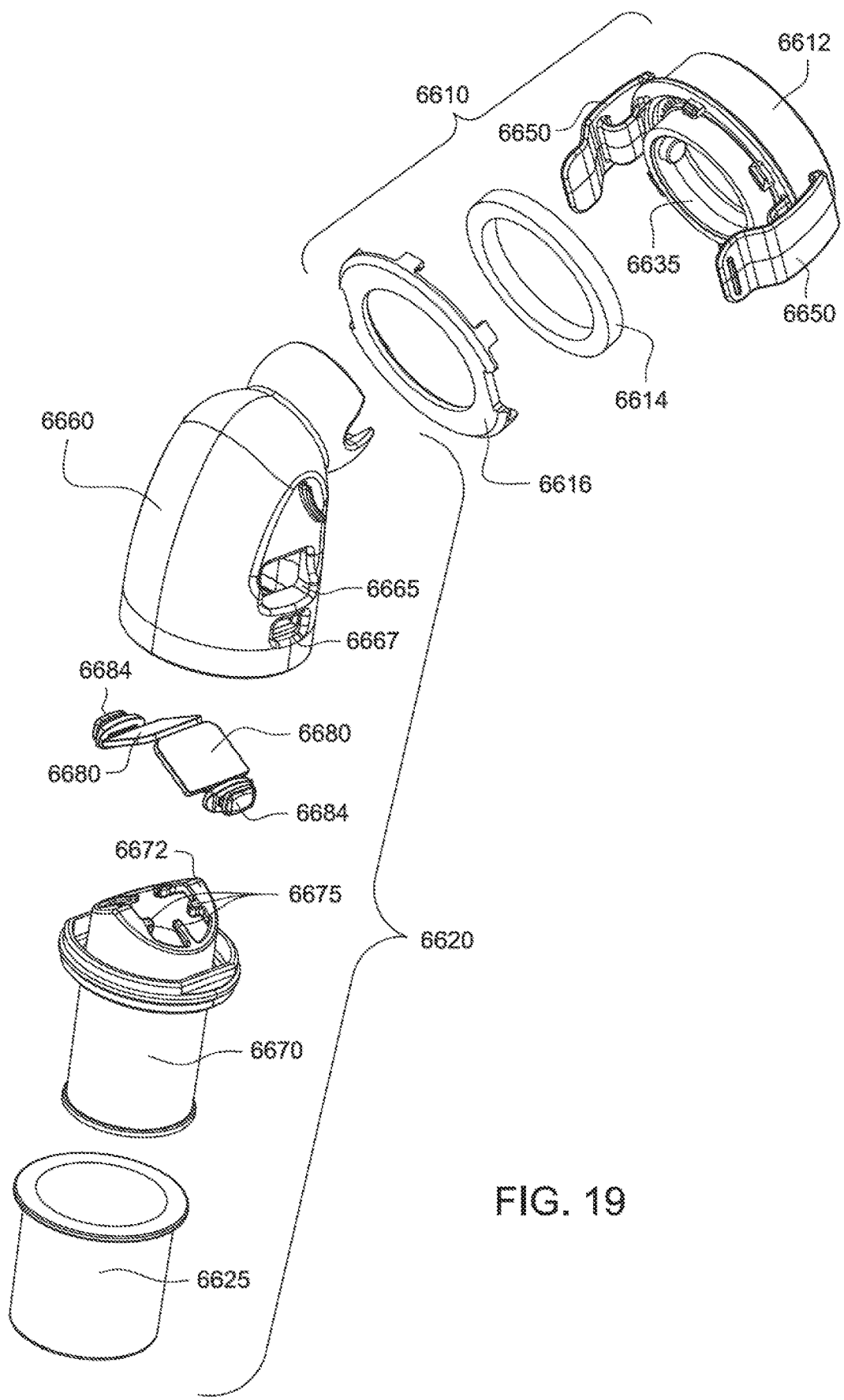

FIG. 19 is a front exploded view of the elbow assembly shown in FIG. 12.

Figure 20:
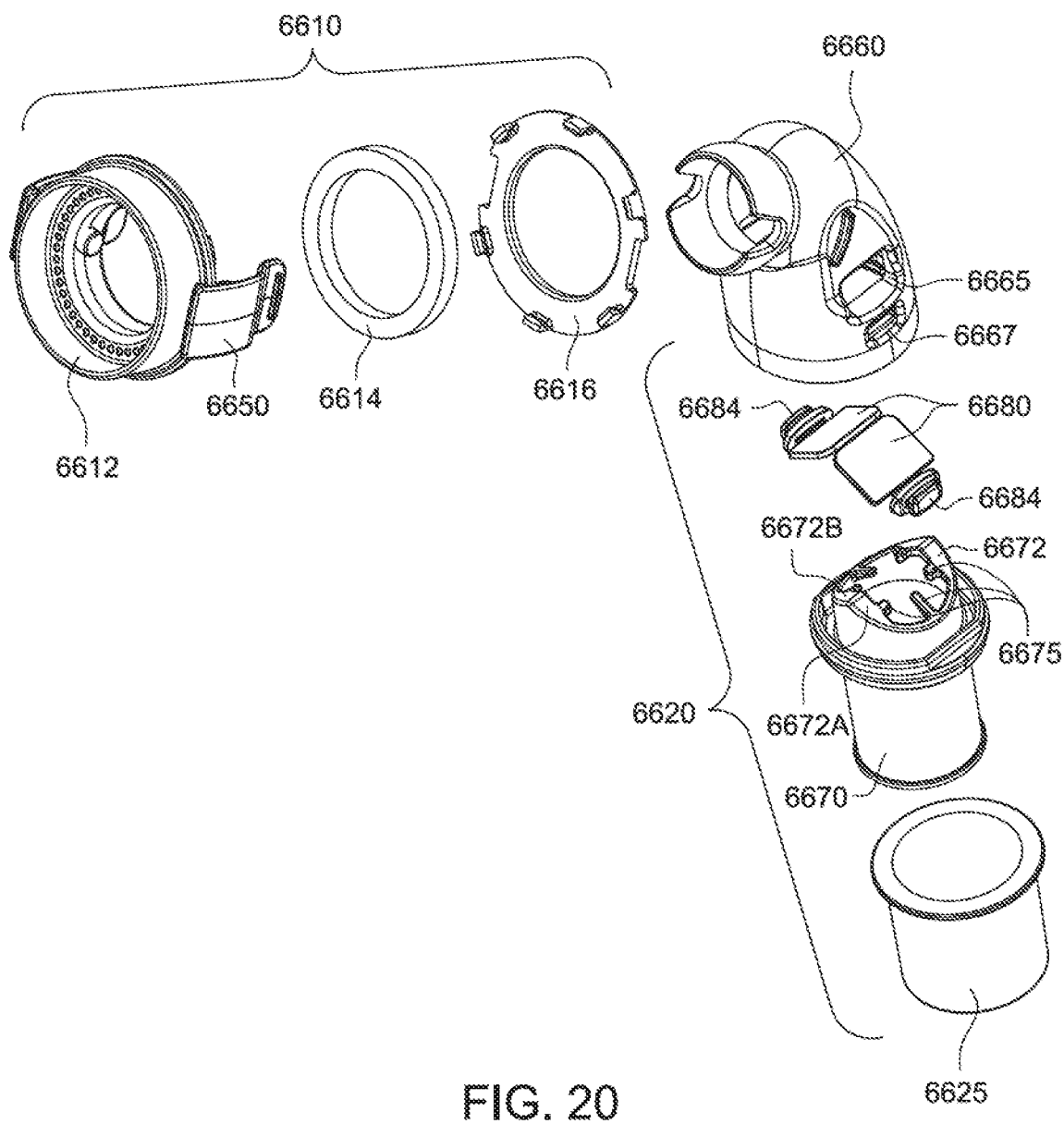

FIG. 20 is a rear exploded view of the elbow assembly shown in FIG. 12.

Figure 21:
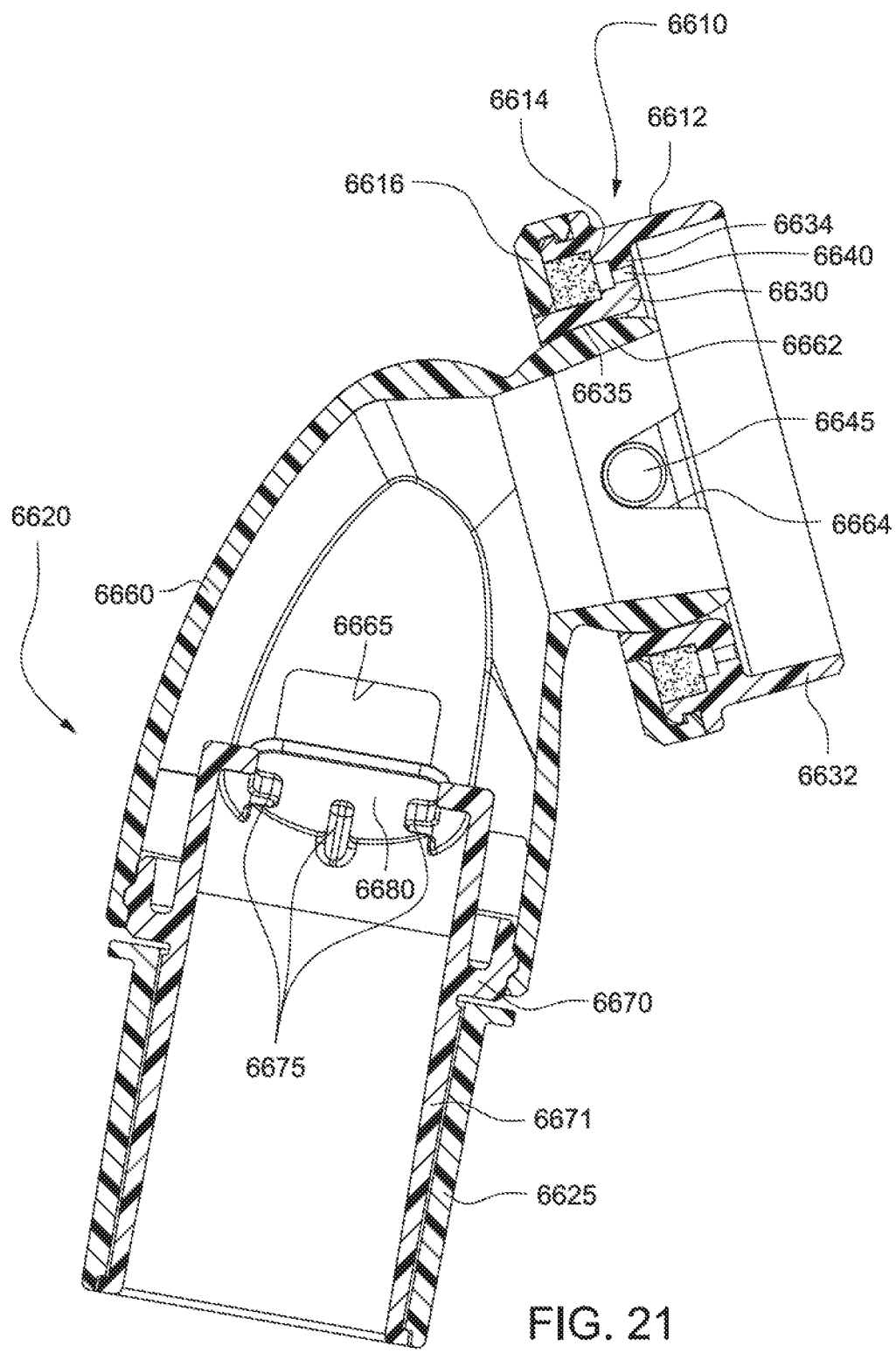

FIG. 21 is a cross-sectional view of the elbow assembly shown in FIG. 15.

Figure 22:
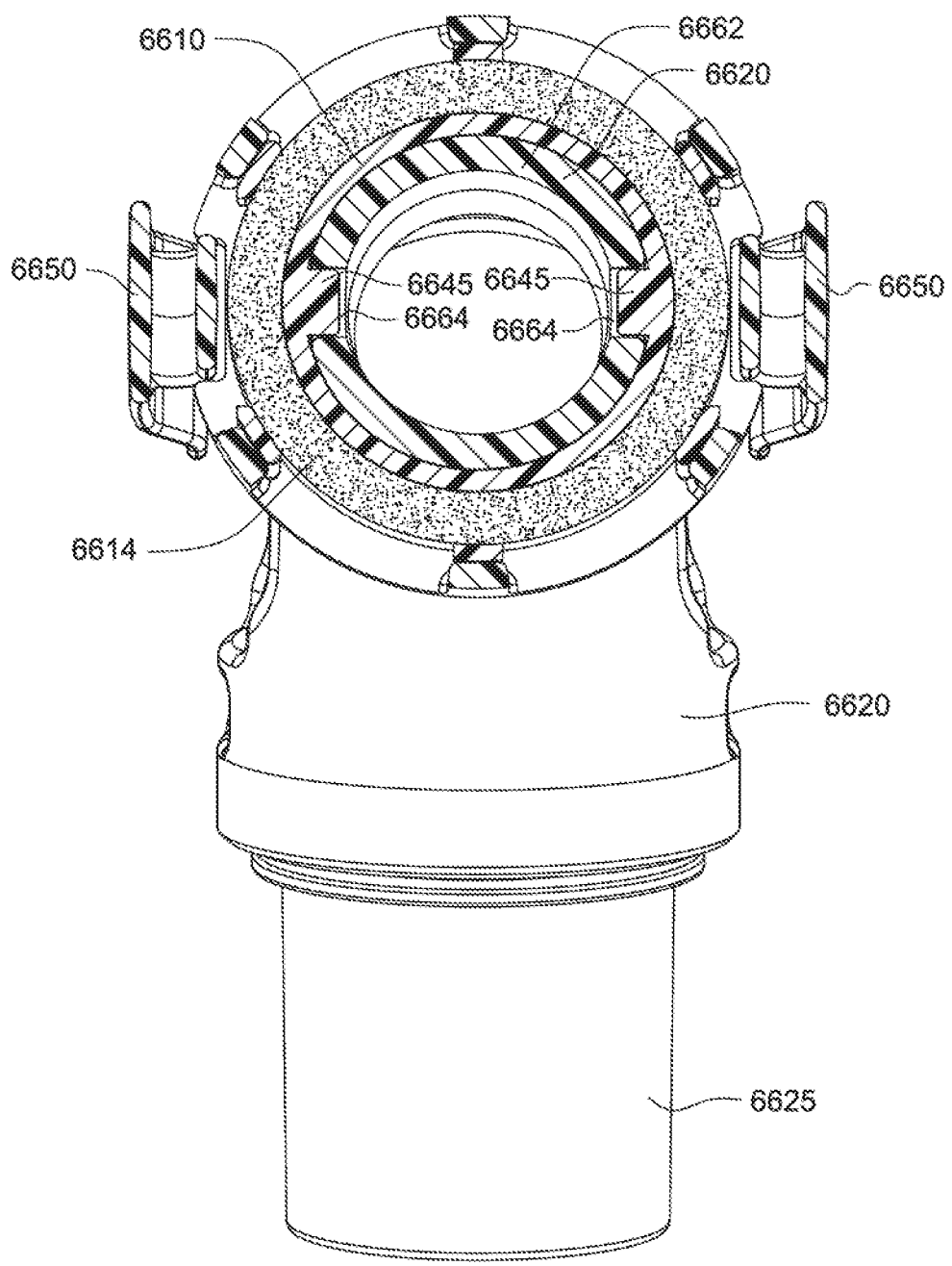

FIG. 22 is a cross-sectional view of the elbow assembly shown in FIG. 14.

Figure 23:
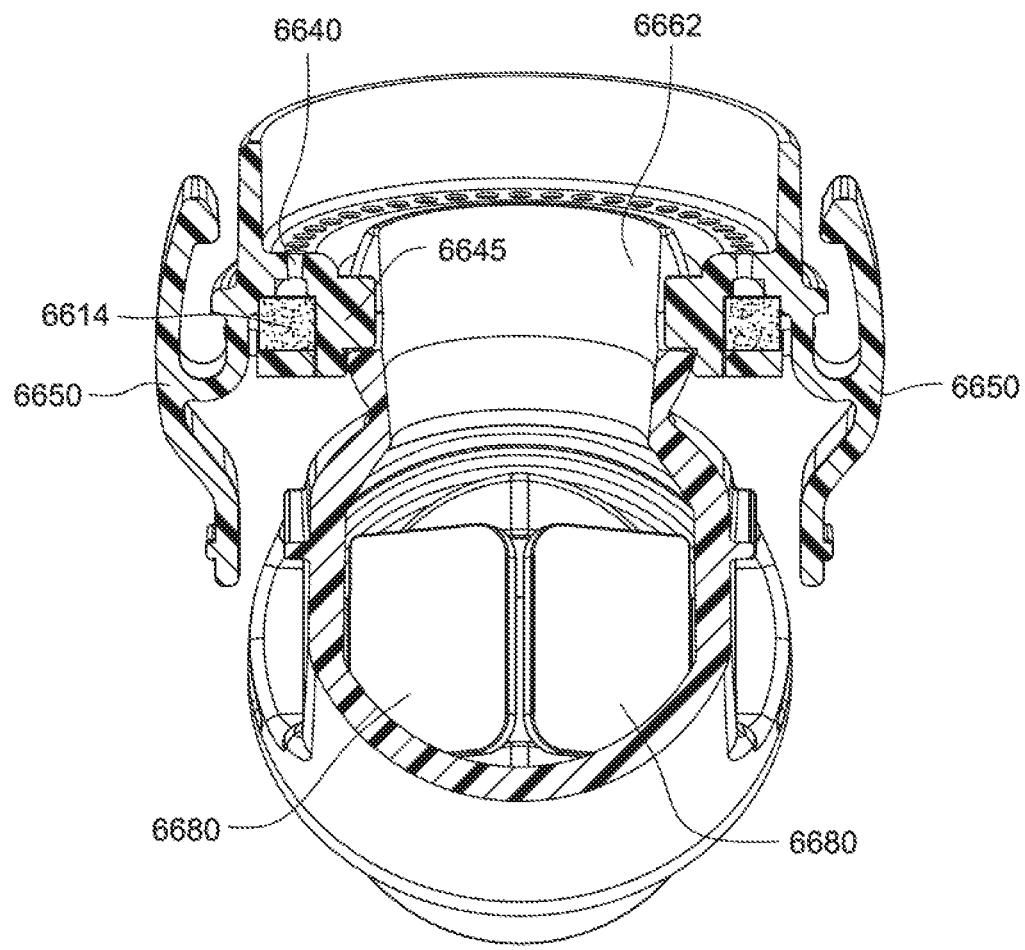

FIG. 23 is a cross-sectional view of the elbow assembly shown in FIG. 14.

Figure 24:
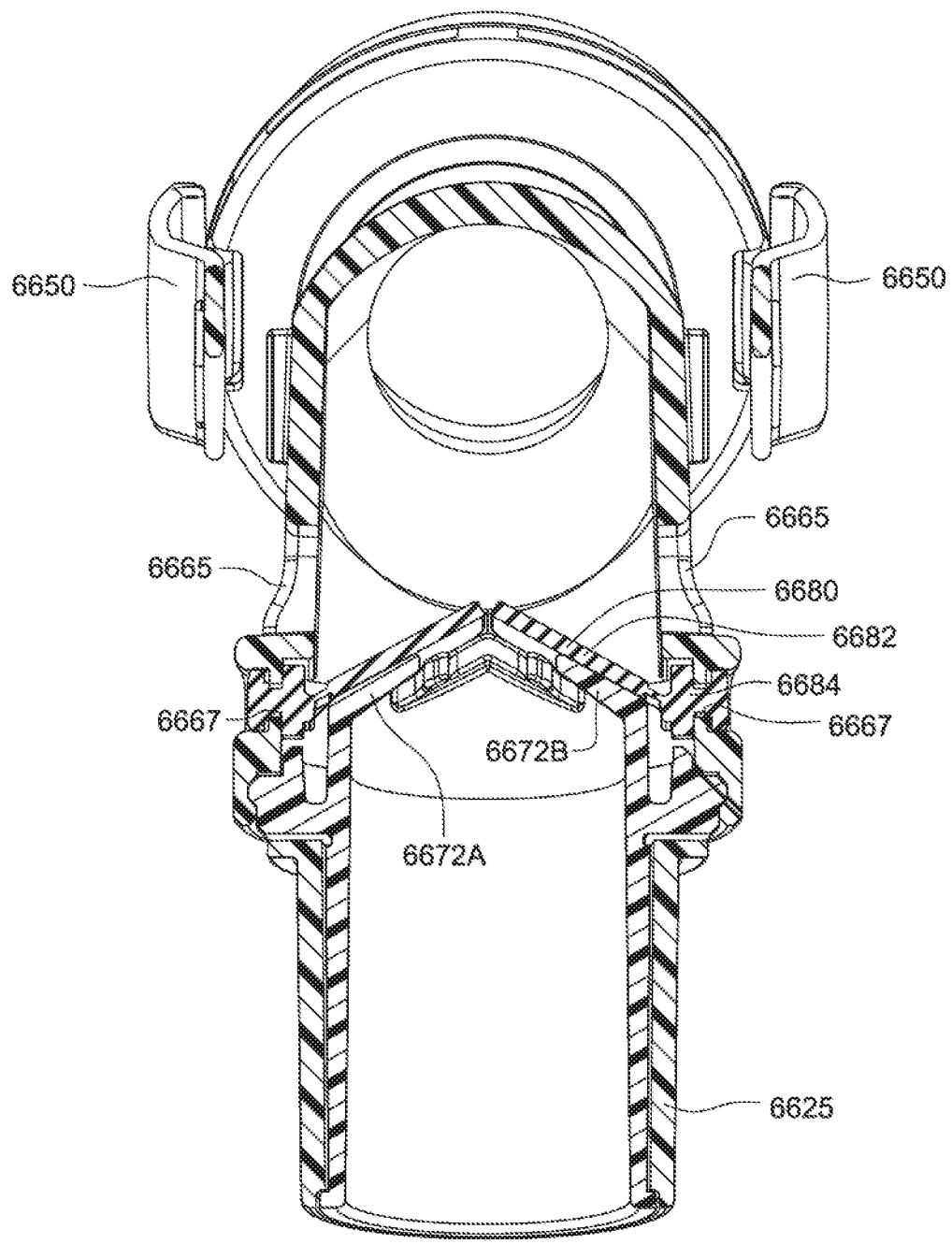

FIG. 24 is a cross-sectional view of the elbow assembly shown in FIG. 14.

Figure 25:
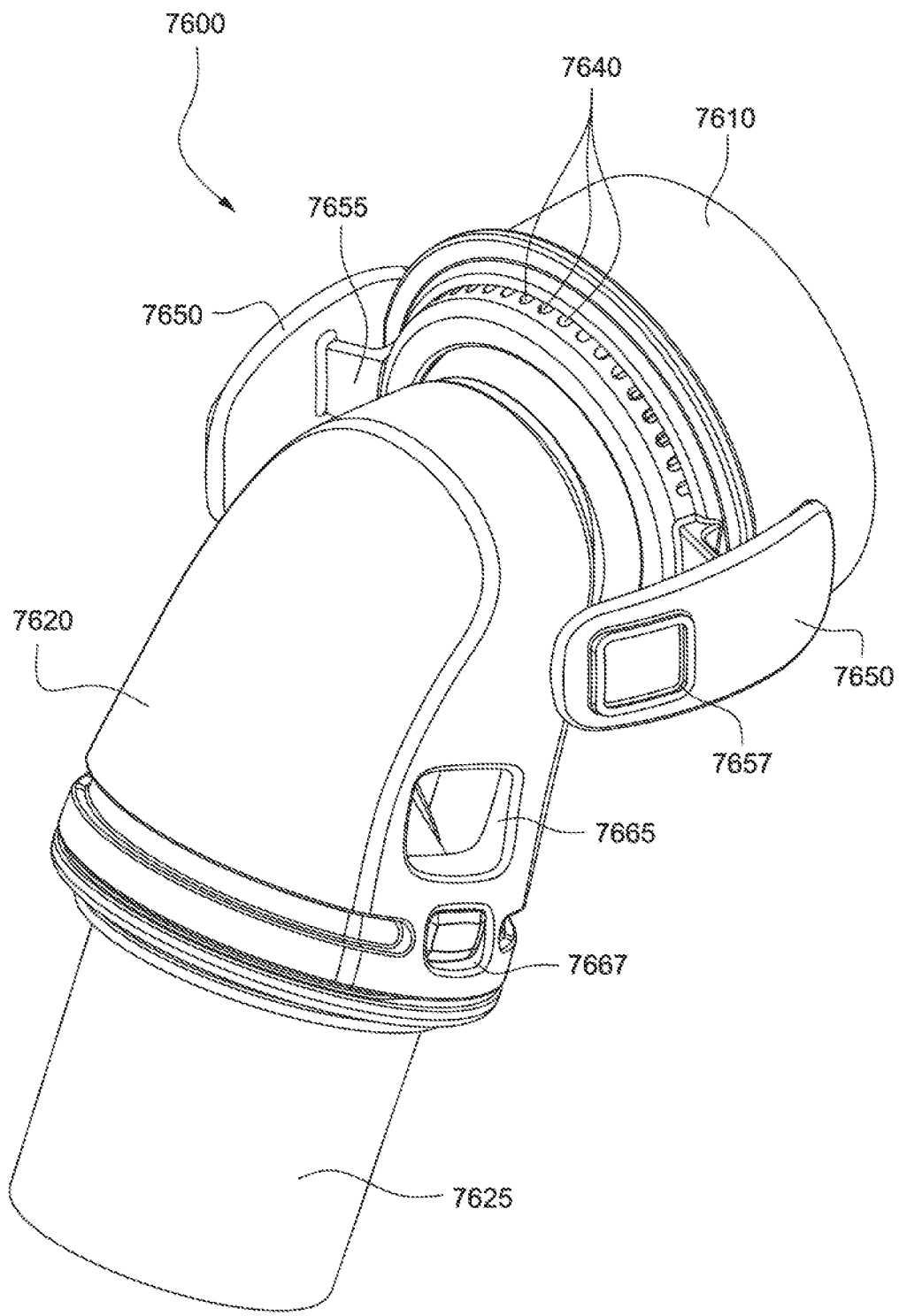

FIG. 25 is a front perspective view of an elbow assembly according to an example of the present technology.

Figure 26:
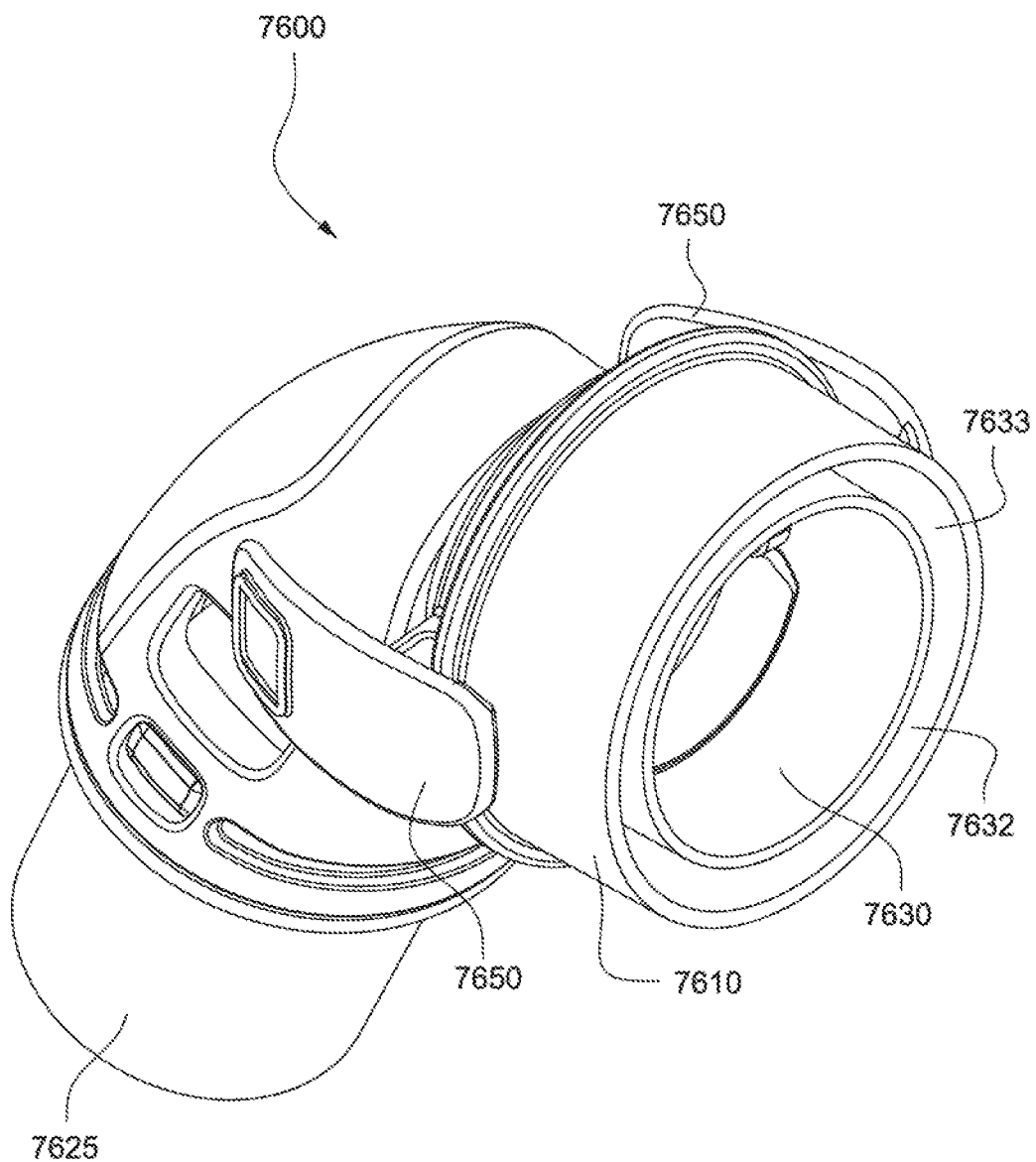

FIG. 26 is a rear perspective view of the elbow assembly shown in FIG. 25.

Figure 27:
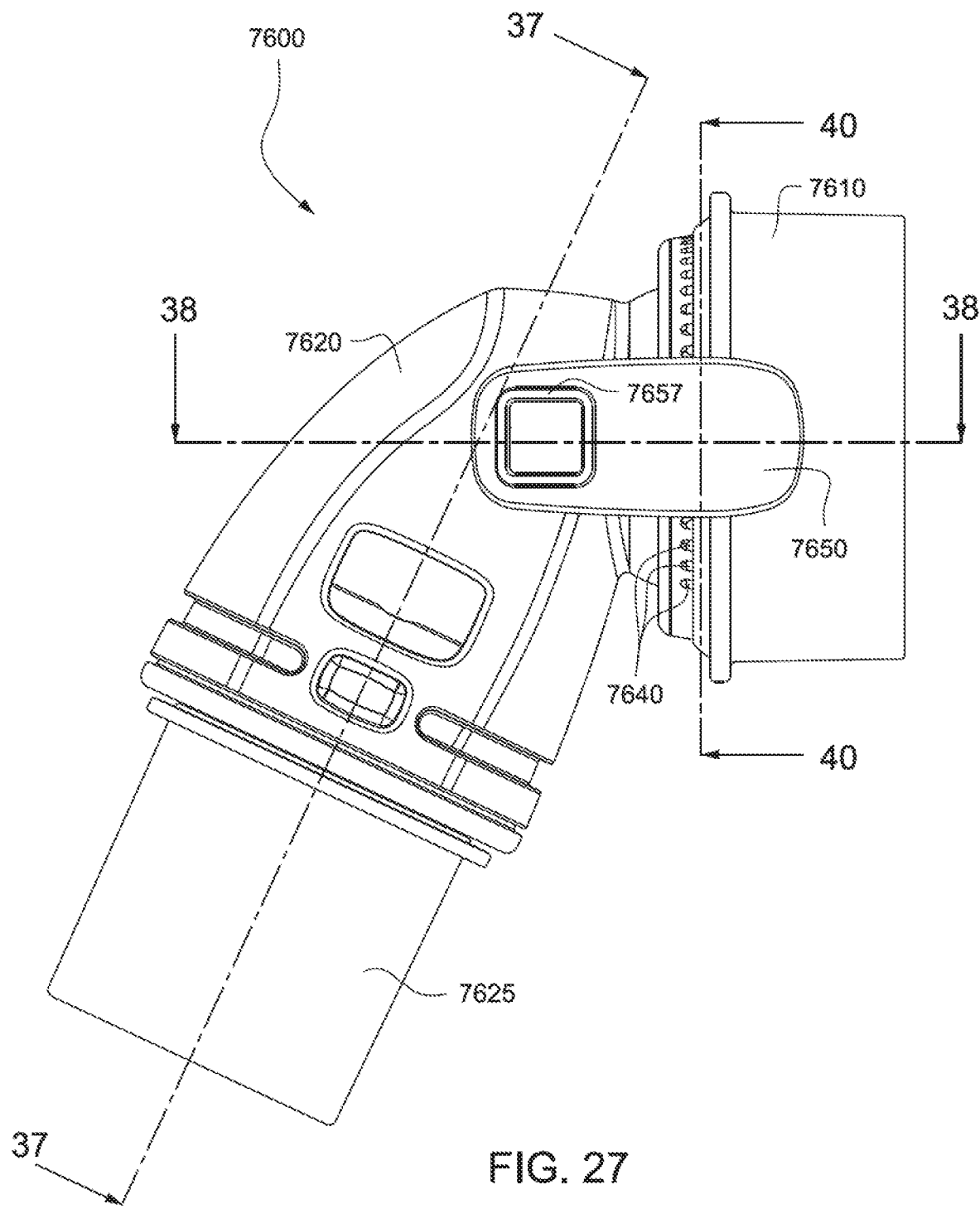

FIG. 27 is a side view of the elbow assembly shown in FIG. 25.

Figure 28:
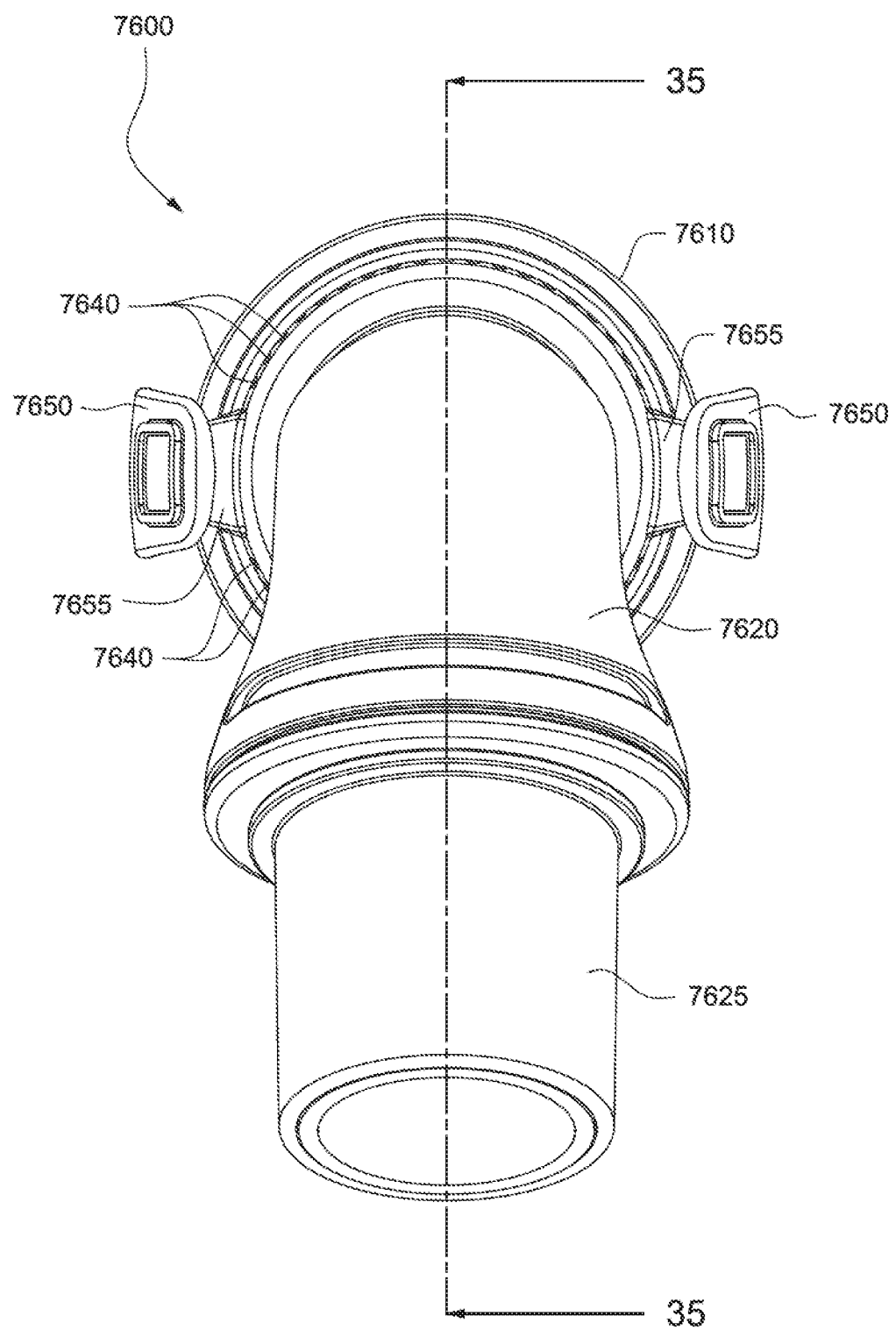

FIG. 28 is a front view of the elbow assembly shown in FIG. 25.

Figure 29:
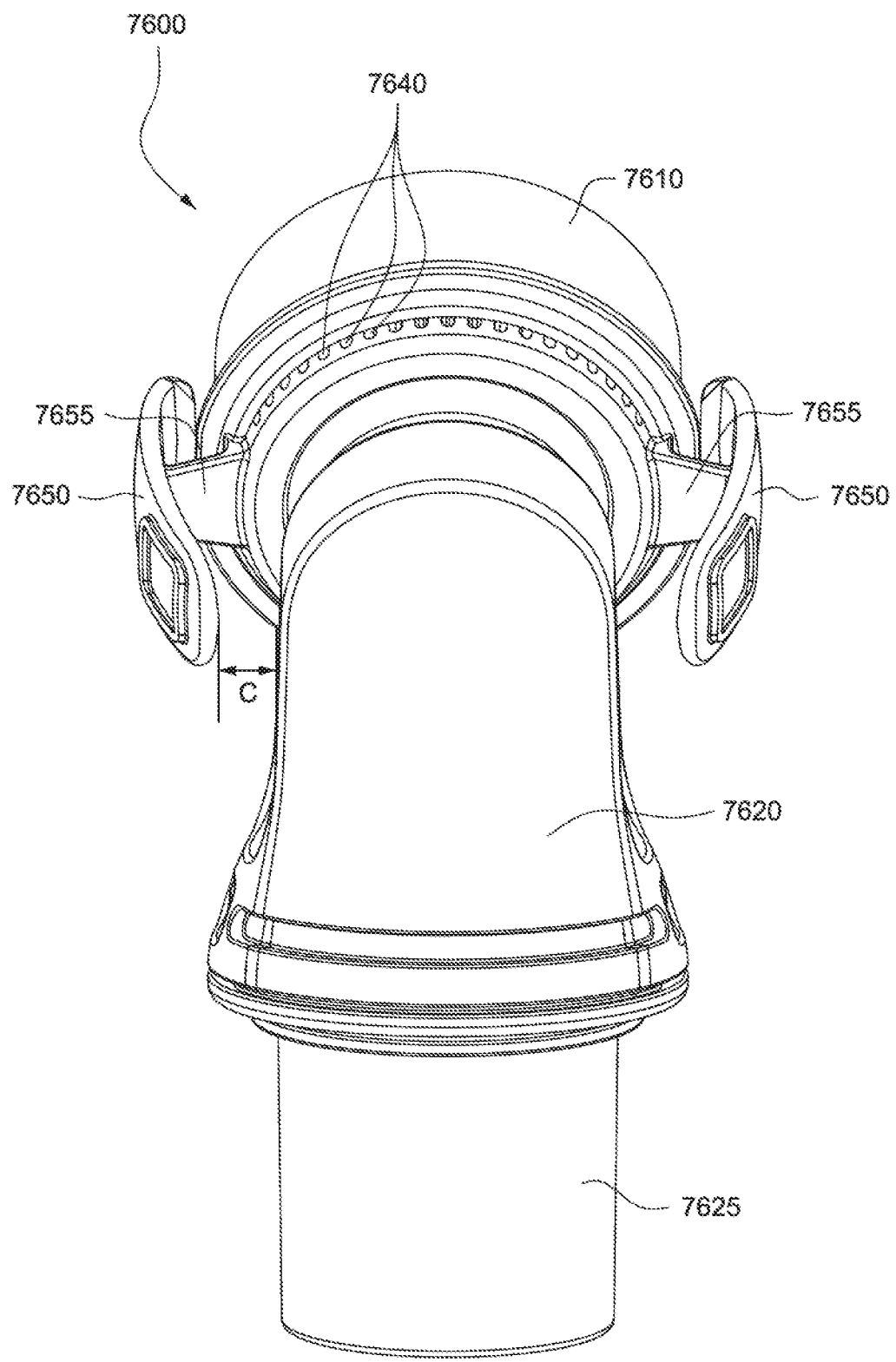

FIG. 29 is another front view of the elbow assembly shown in FIG. 25.

Figure 30:
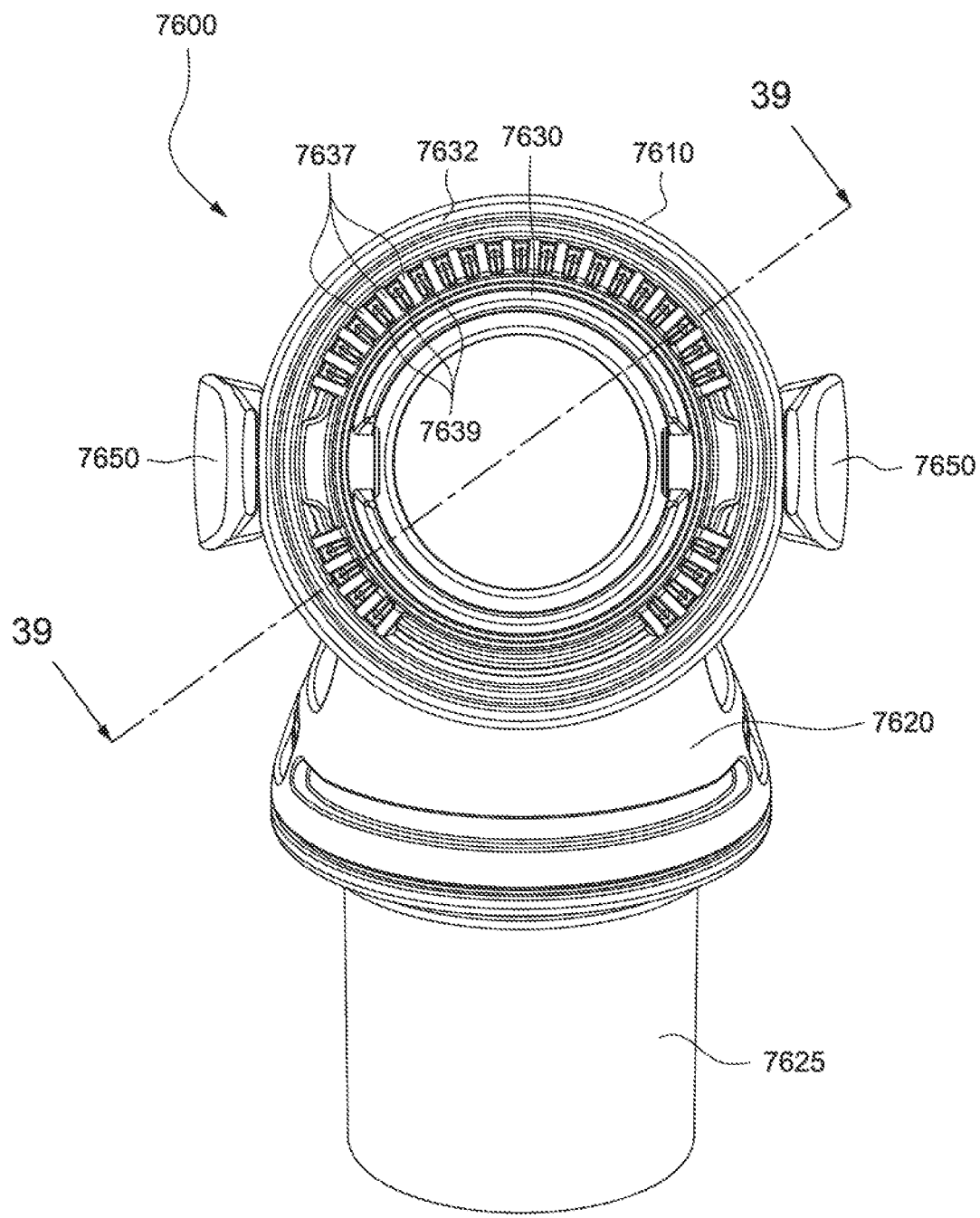

FIG. 30 is a rear view of the elbow assembly shown in FIG. 25.

Figure 31:
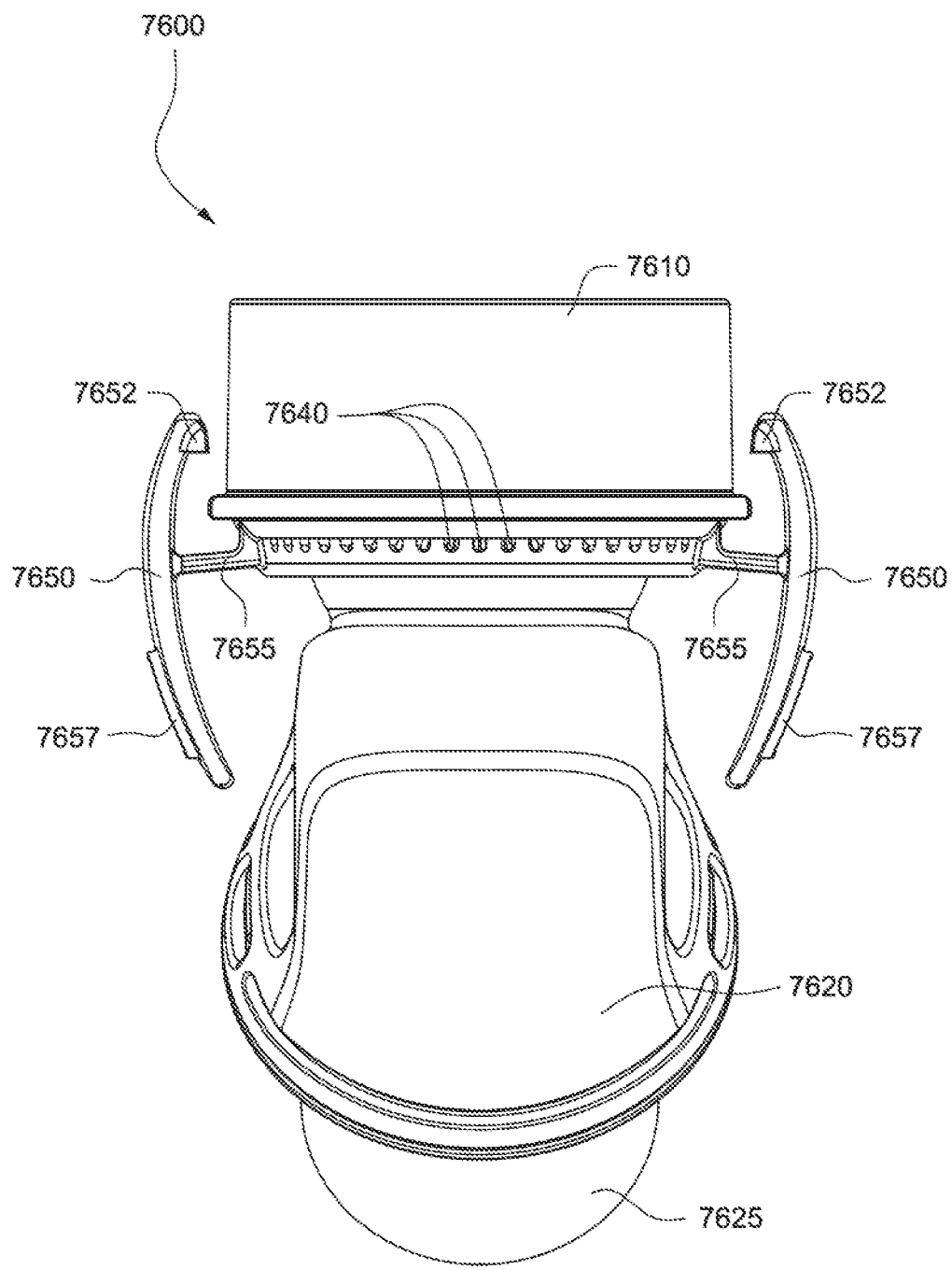

FIG. 31 is a top view of the elbow assembly shown in FIG. 25.

Figure 32:
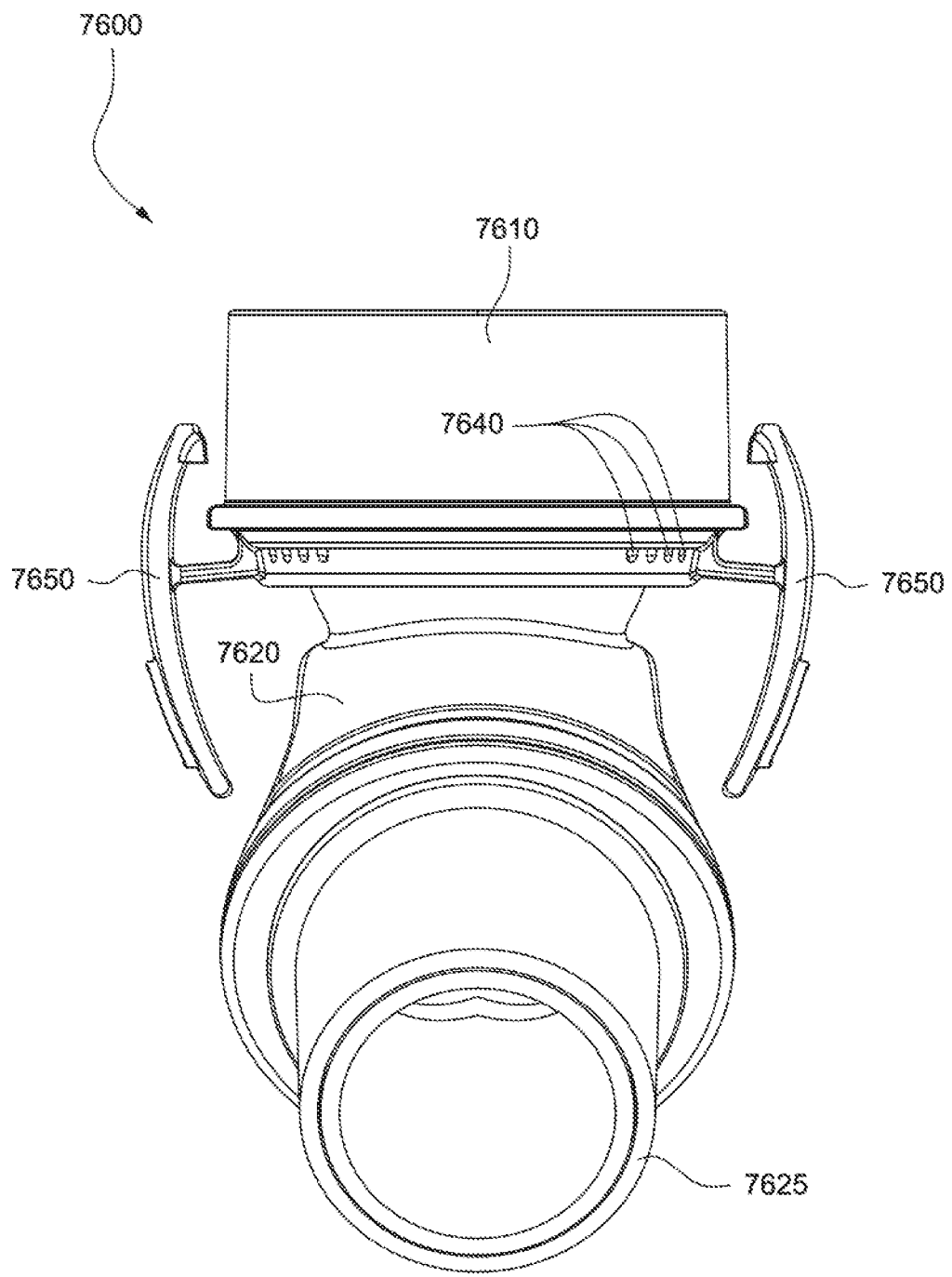

FIG. 32 is a bottom view of the elbow assembly shown in FIG. 25.

Figure 33:
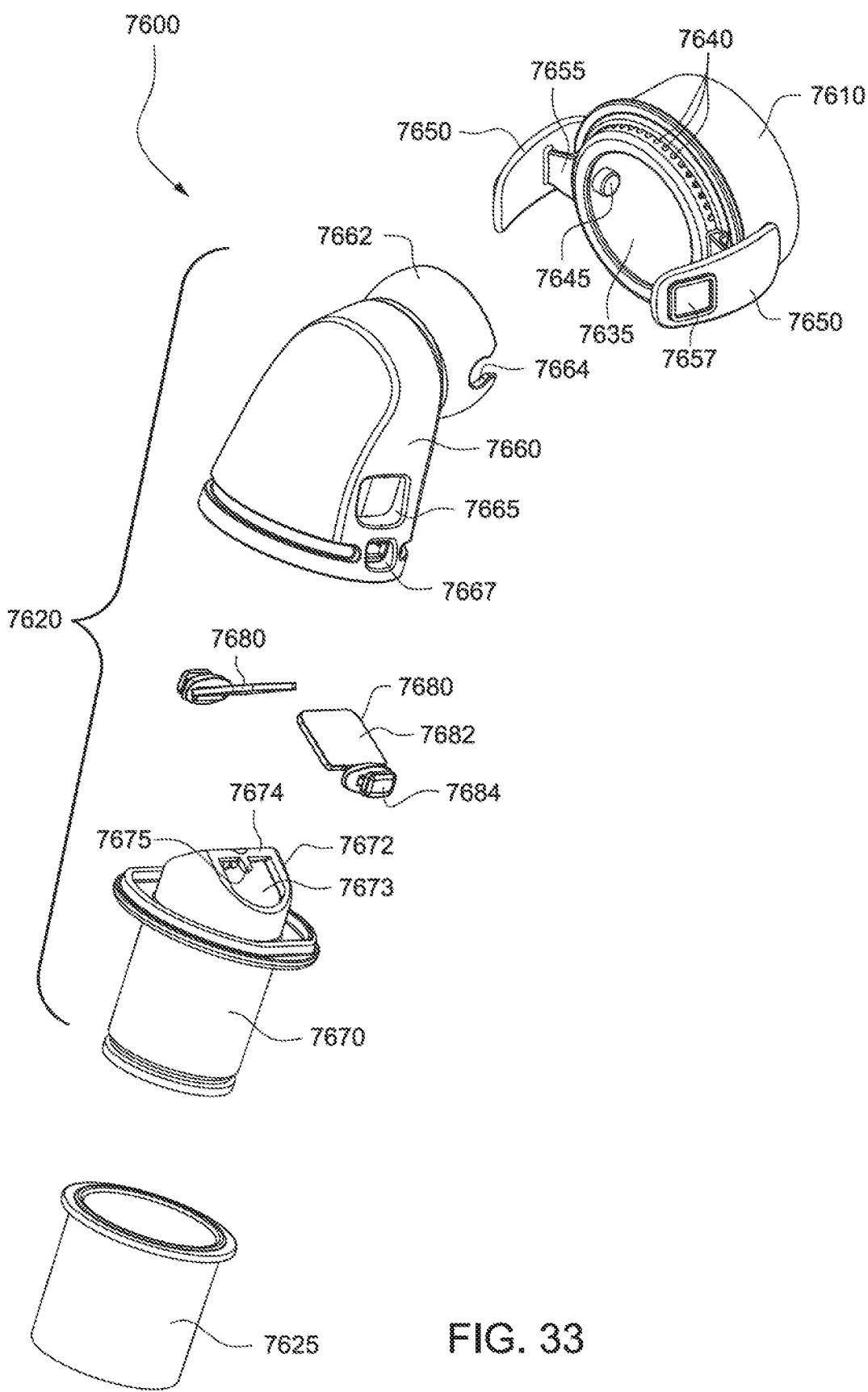

FIG. 33 is a front exploded view of the elbow assembly shown in FIG. 25.

Figure 34:
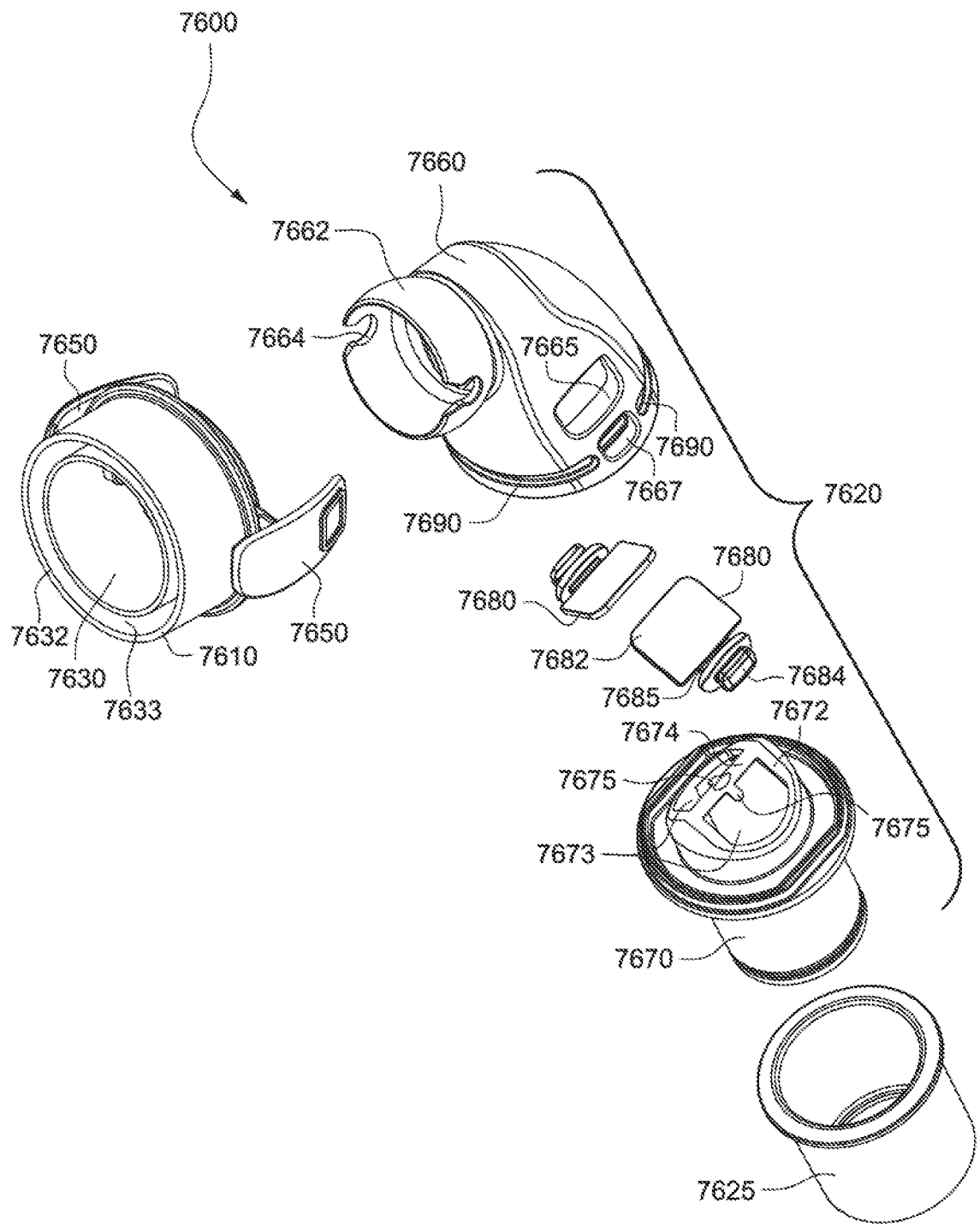

FIG. 34 is a rear exploded view of the elbow assembly shown in FIG. 25.

Figure 35:
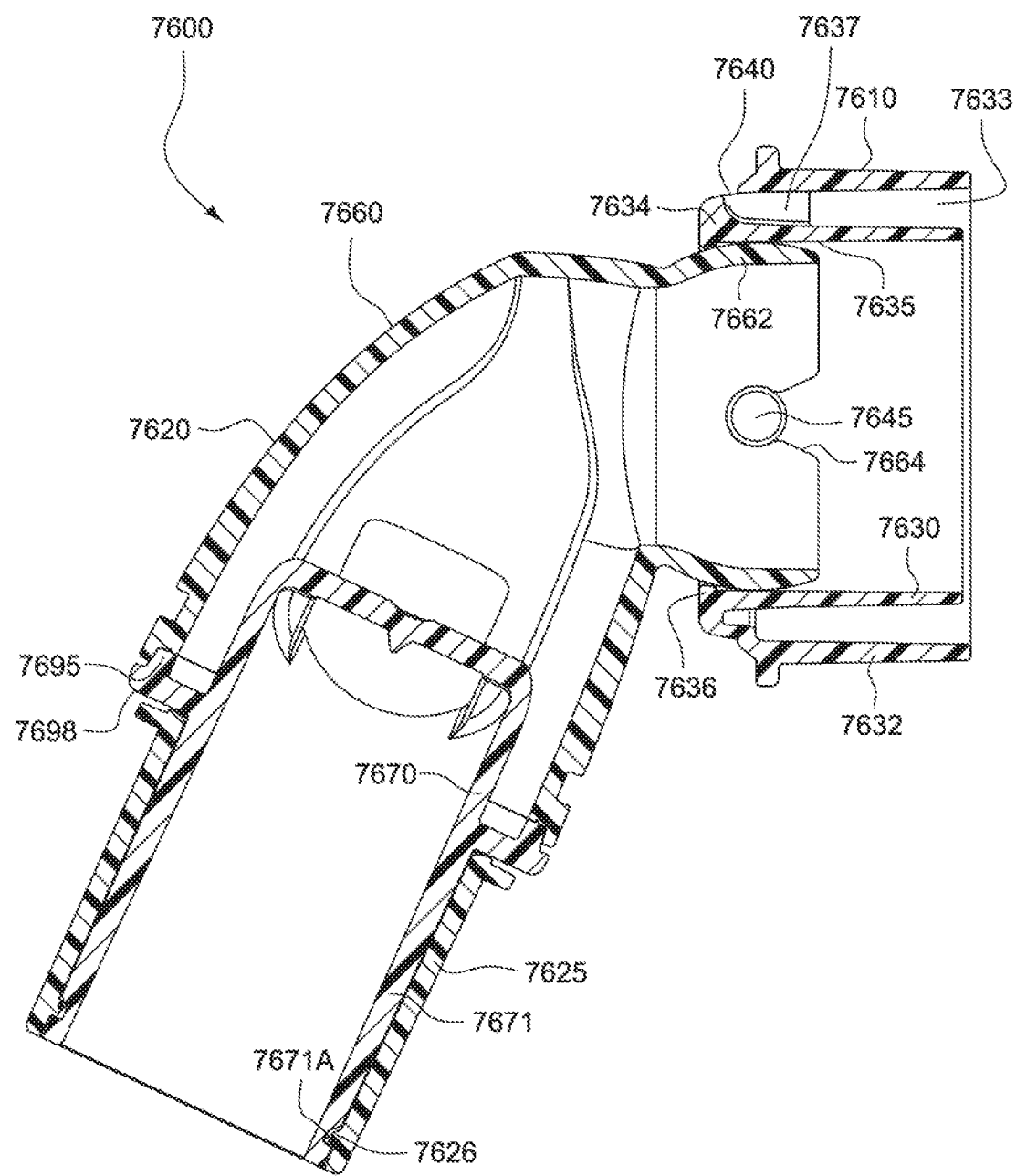

FIG. 35 is a cross-sectional view of the elbow assembly shown in FIG. 28.

Figure 36:
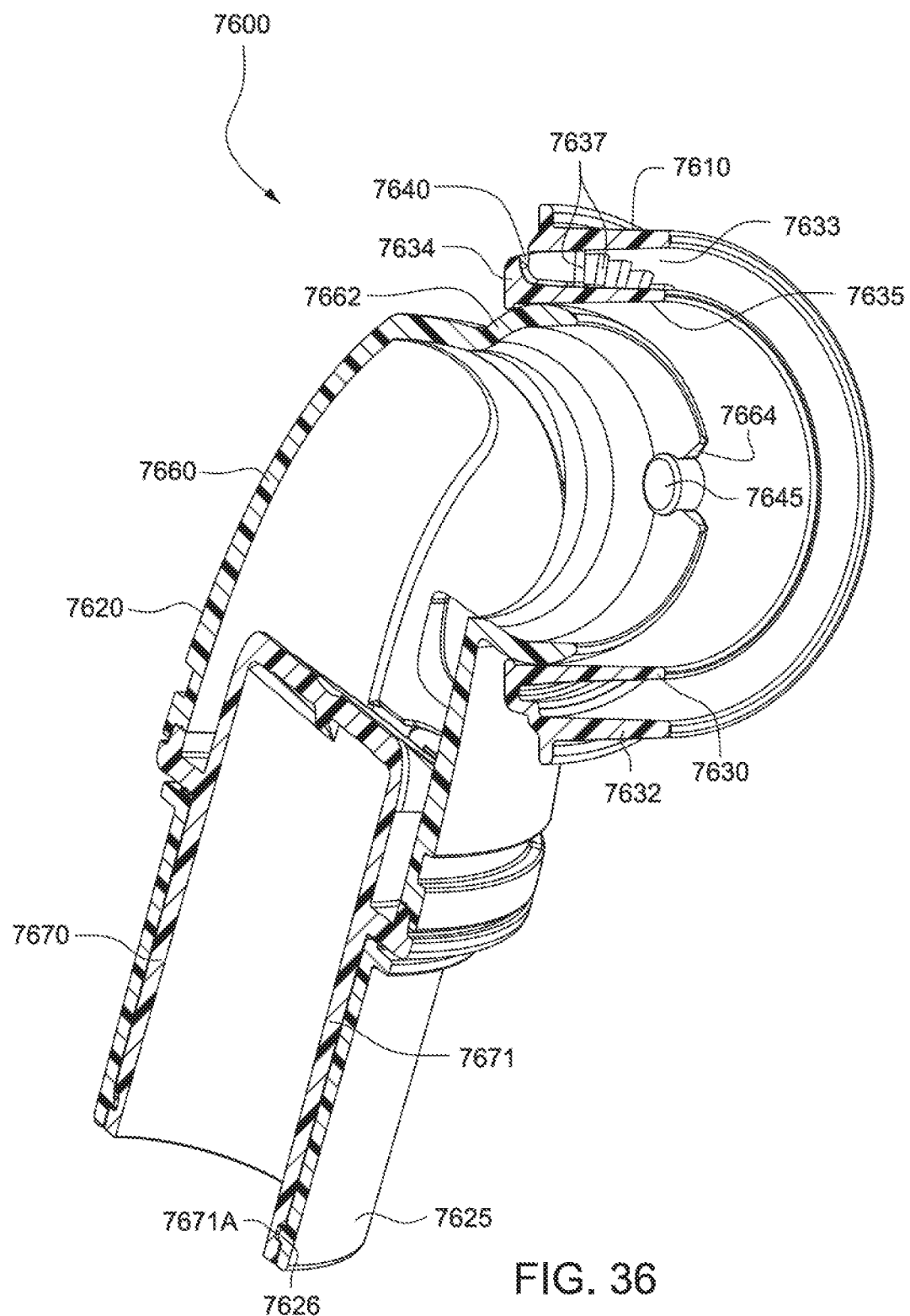

FIG. 36 is a perspective view of the cross-section of FIG. 35.

Figure 37:
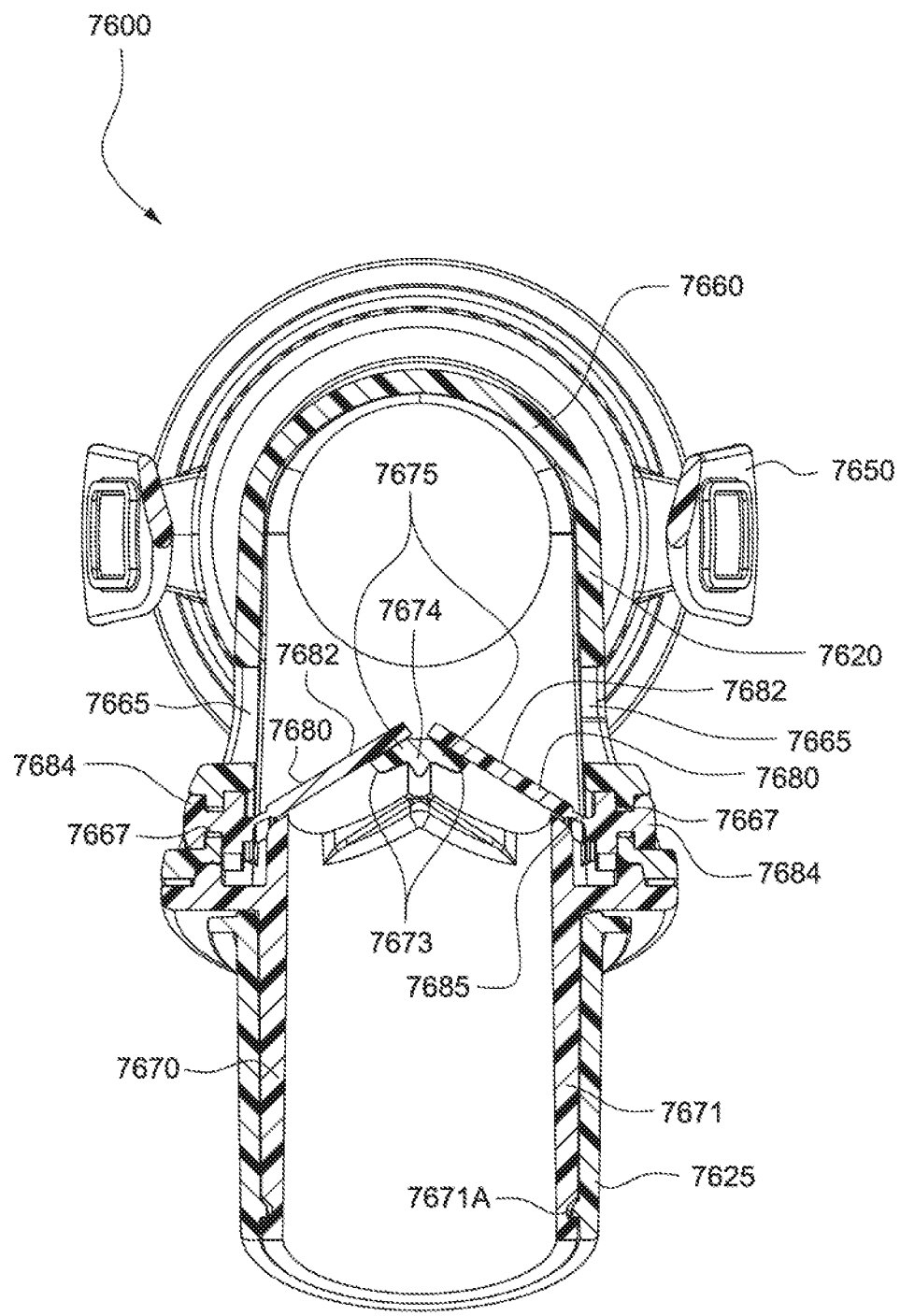

FIG. 37 is a cross-sectional view of the elbow assembly shown in FIG. 27.

Figure 38:
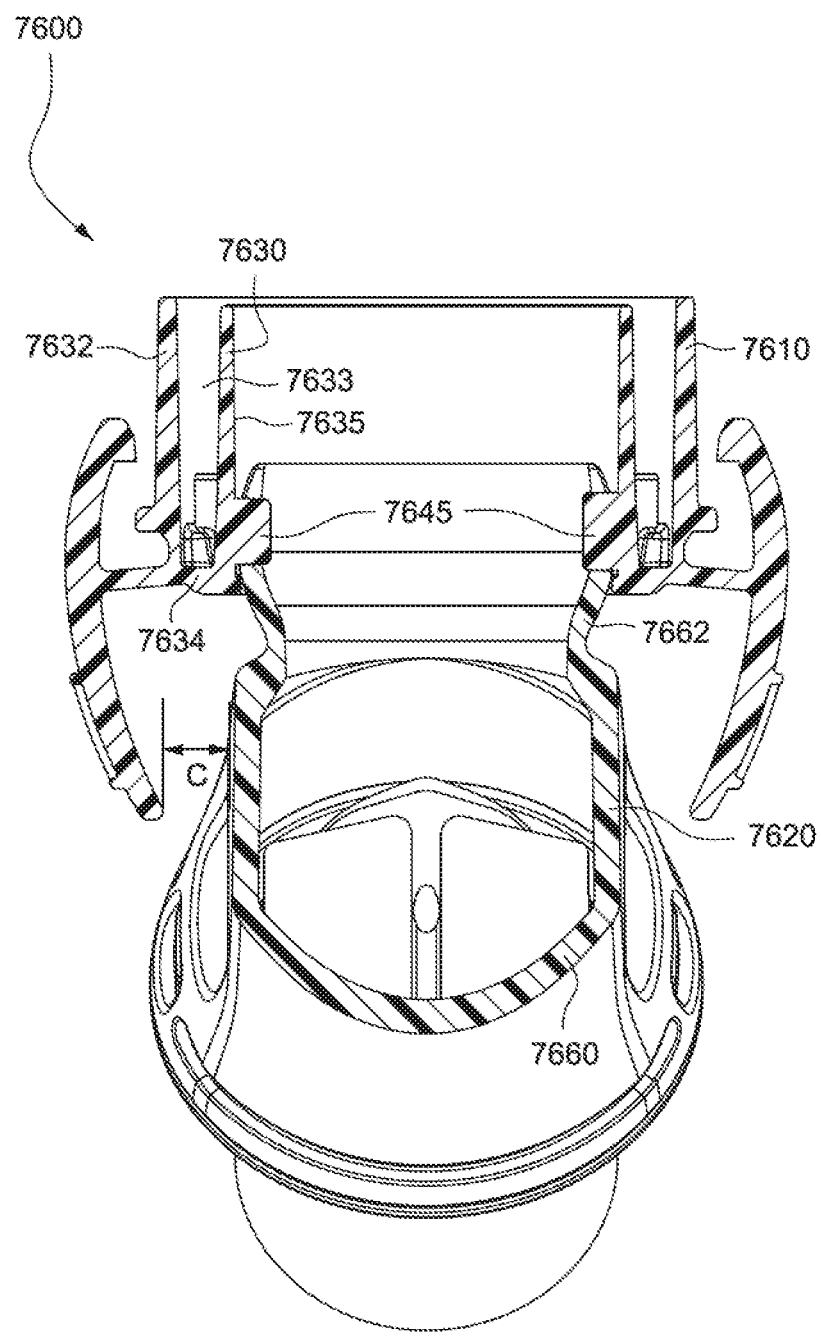

FIG. 38 is a cross-sectional view of the elbow assembly shown in FIG. 27.

Figure 39:
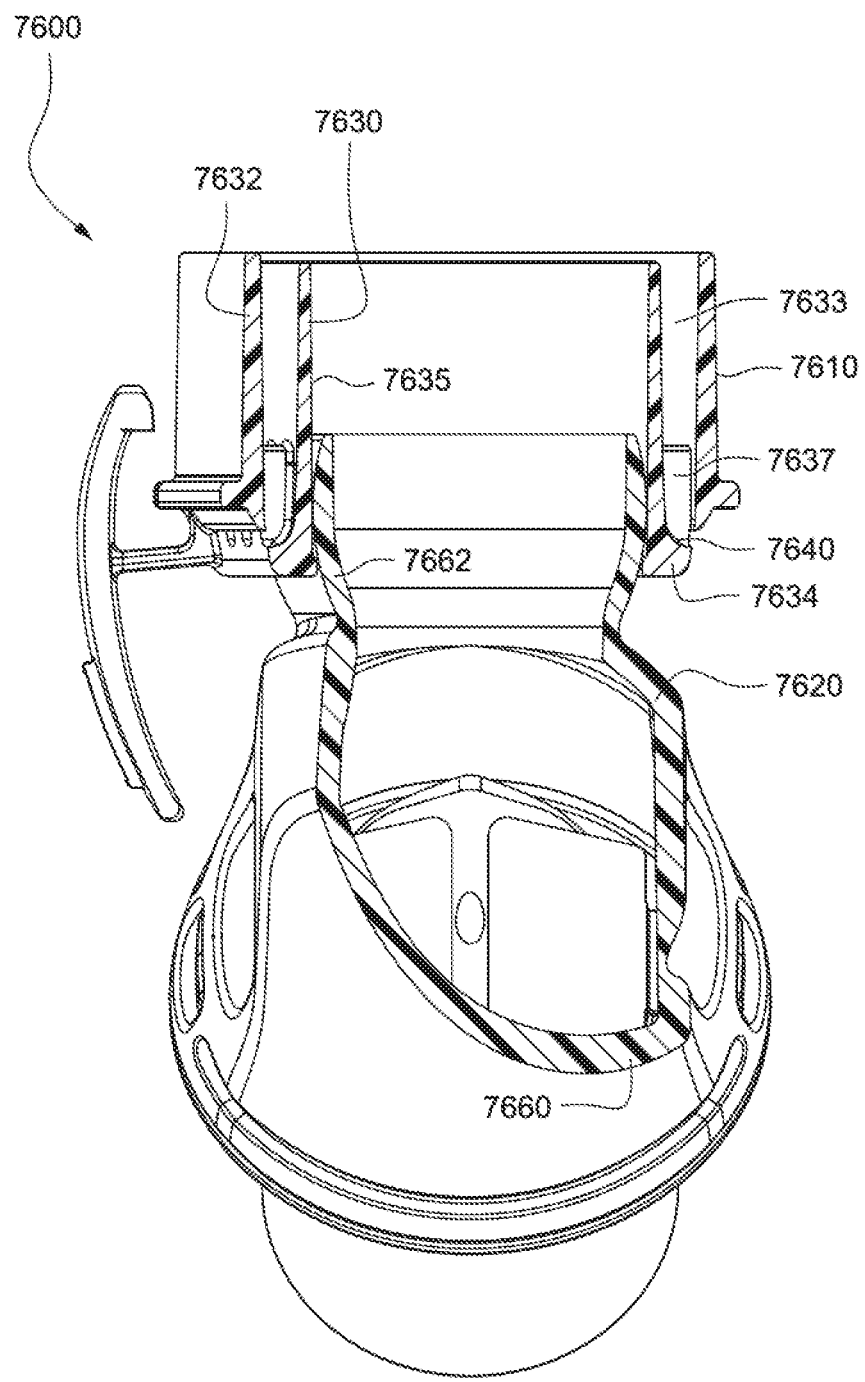

FIG. 39 is a cross-sectional view of the elbow assembly shown in FIG. 30.

Figure 40:
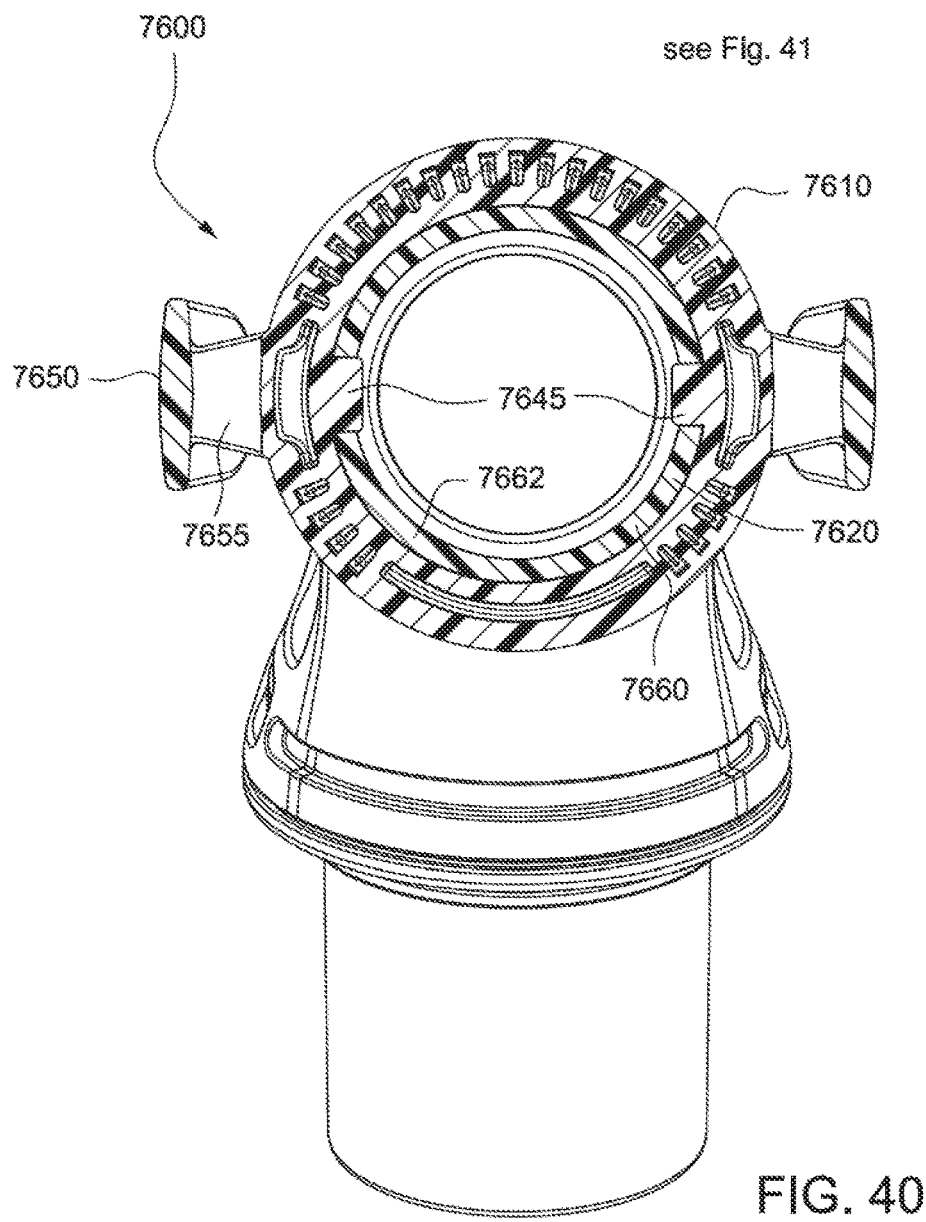

FIG. 40 is a cross-sectional view of the elbow assembly shown in FIG. 27.

Figure 41:
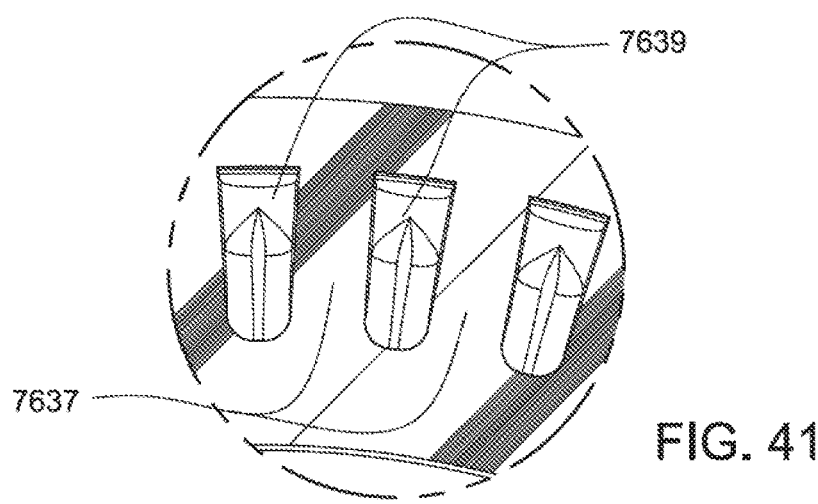

FIG. 41 is an enlarged portion of the cross-section of FIG. 40.

Figure 42:
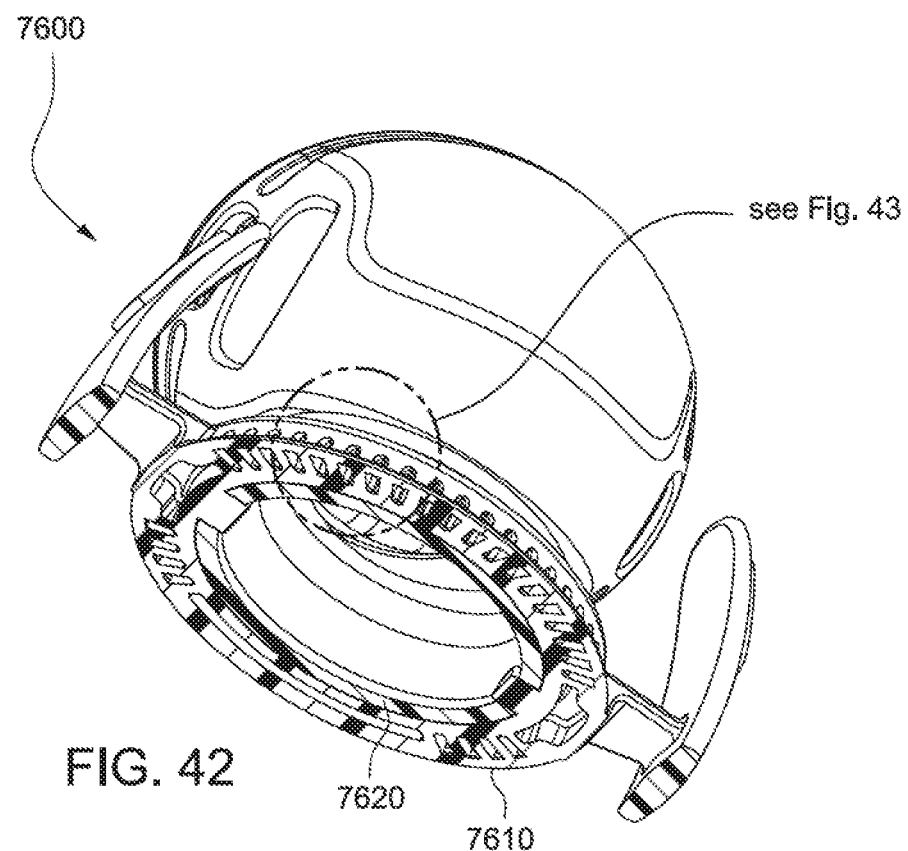

FIG. 42 is a perspective view of the cross-section of FIG. 40.

Figure 43:
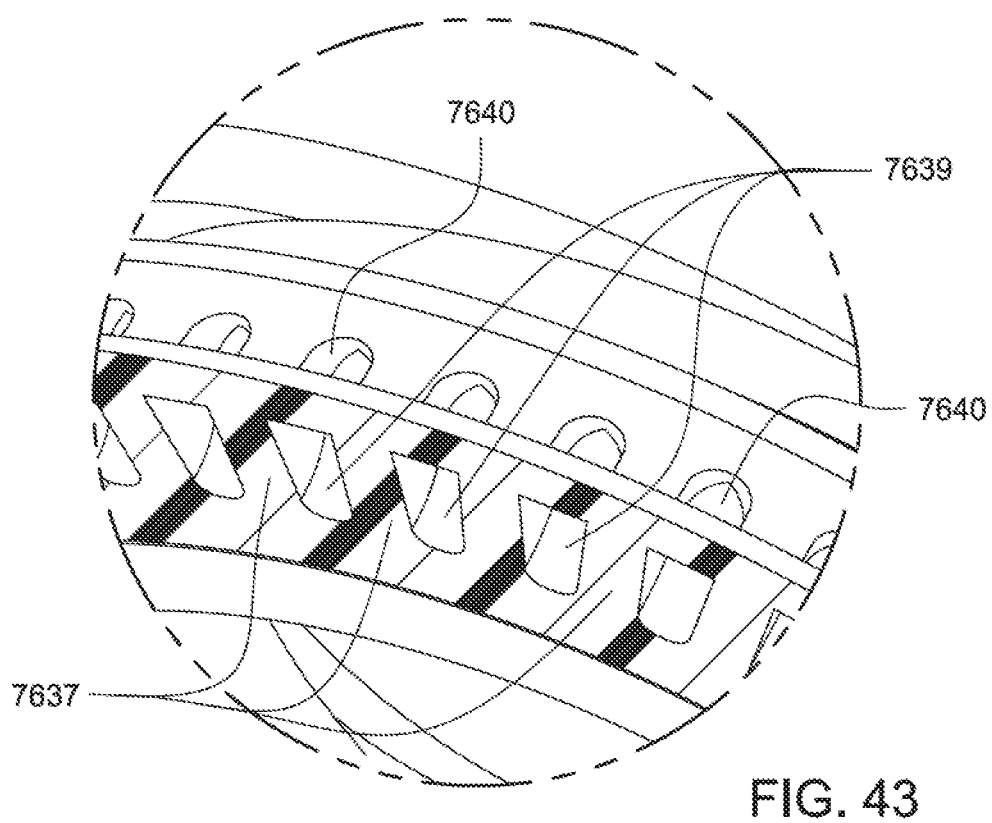

FIG. 43 is an enlarged portion of the cross-section of FIG. 42.

Figure 44:
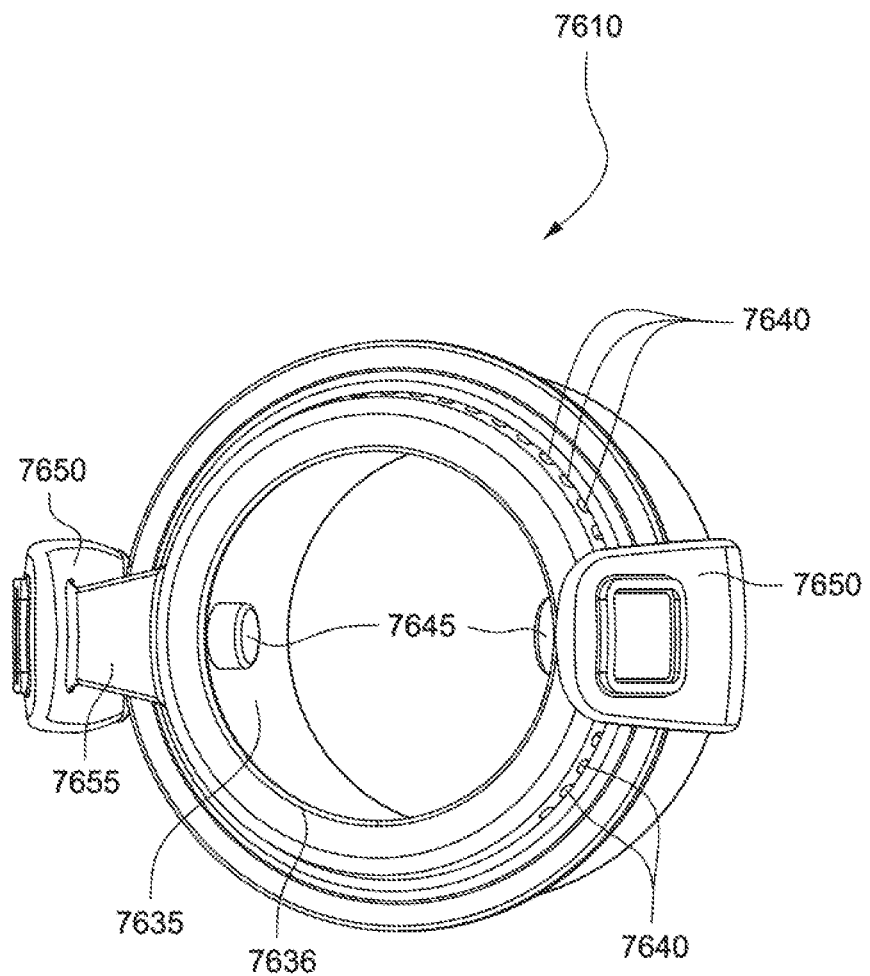

FIG. 44 is a perspective view of a swivel component of the elbow assembly shown in FIG. 25.

Figure 45:
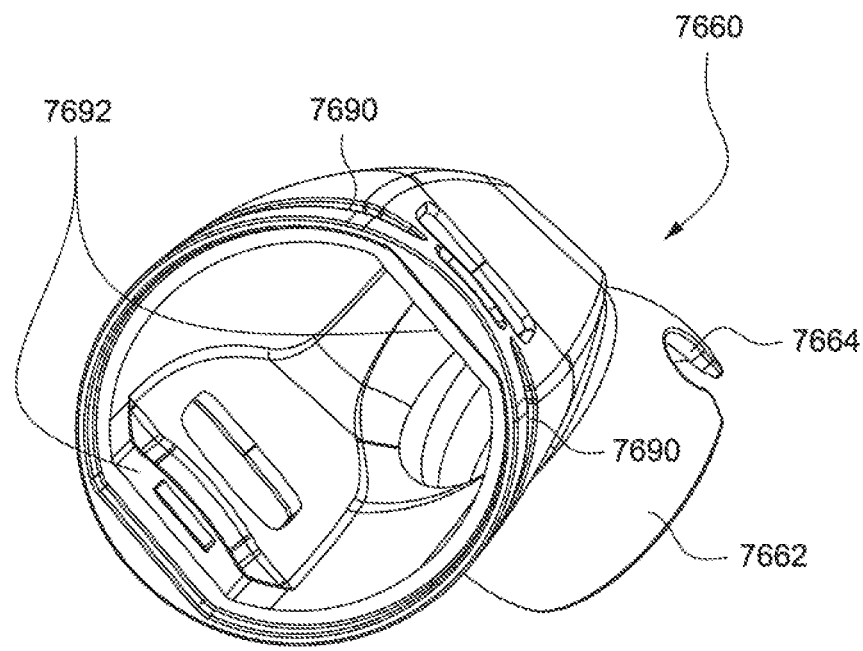

FIG. 45 is a perspective view of a first end of an elbow component of the elbow assembly shown in FIG. 25.

Figure 46:
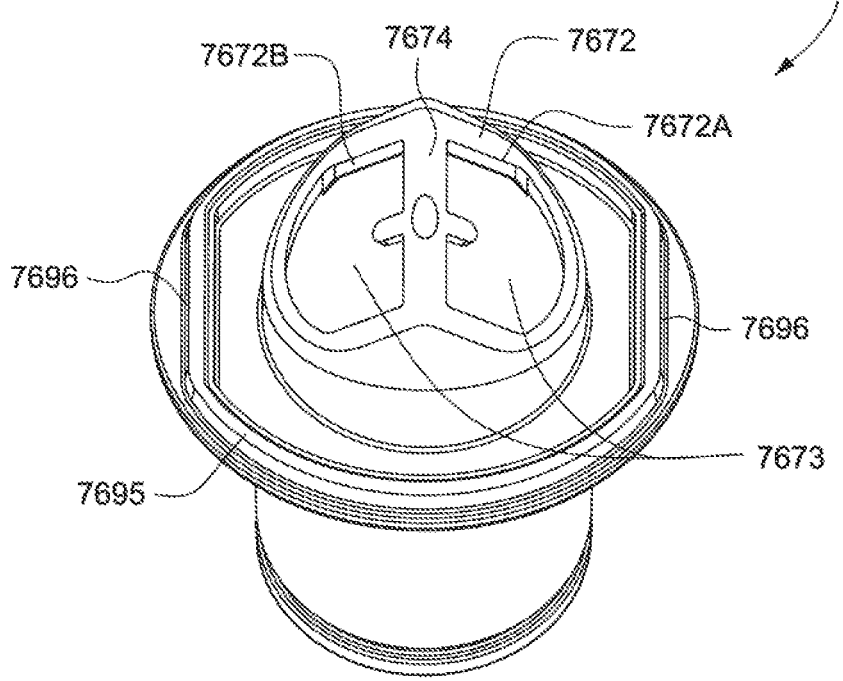

FIG. 46 is a perspective view of a second end of an elbow component of the elbow assembly shown in FIG. 25.

Figure 47:
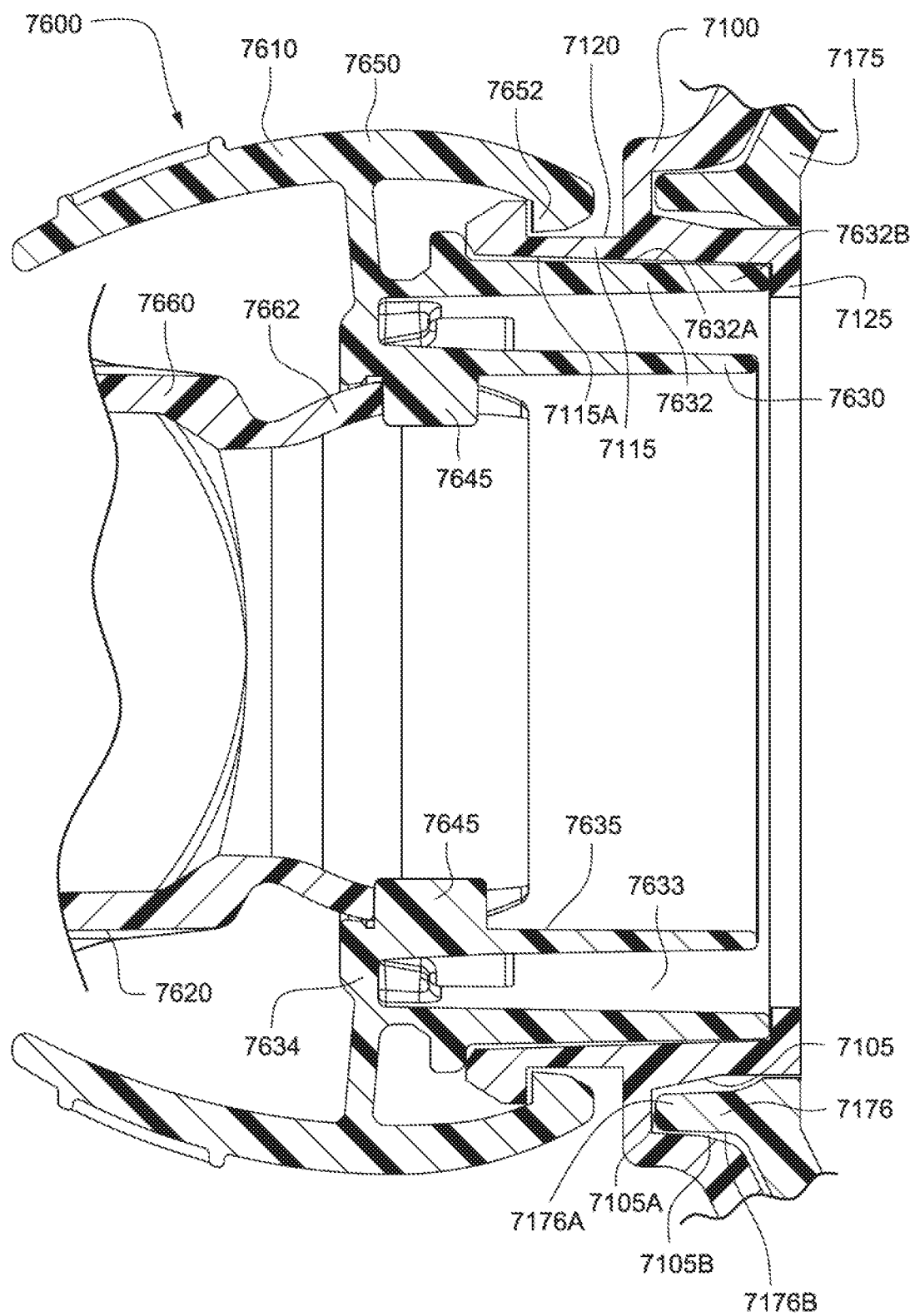

FIG. 47 is a cross-sectional view showing a cushion assembly and frame assembly removably connected with the elbow assembly shown in FIG. 25 assembly according to an example of the present technology.

Figure 48A:
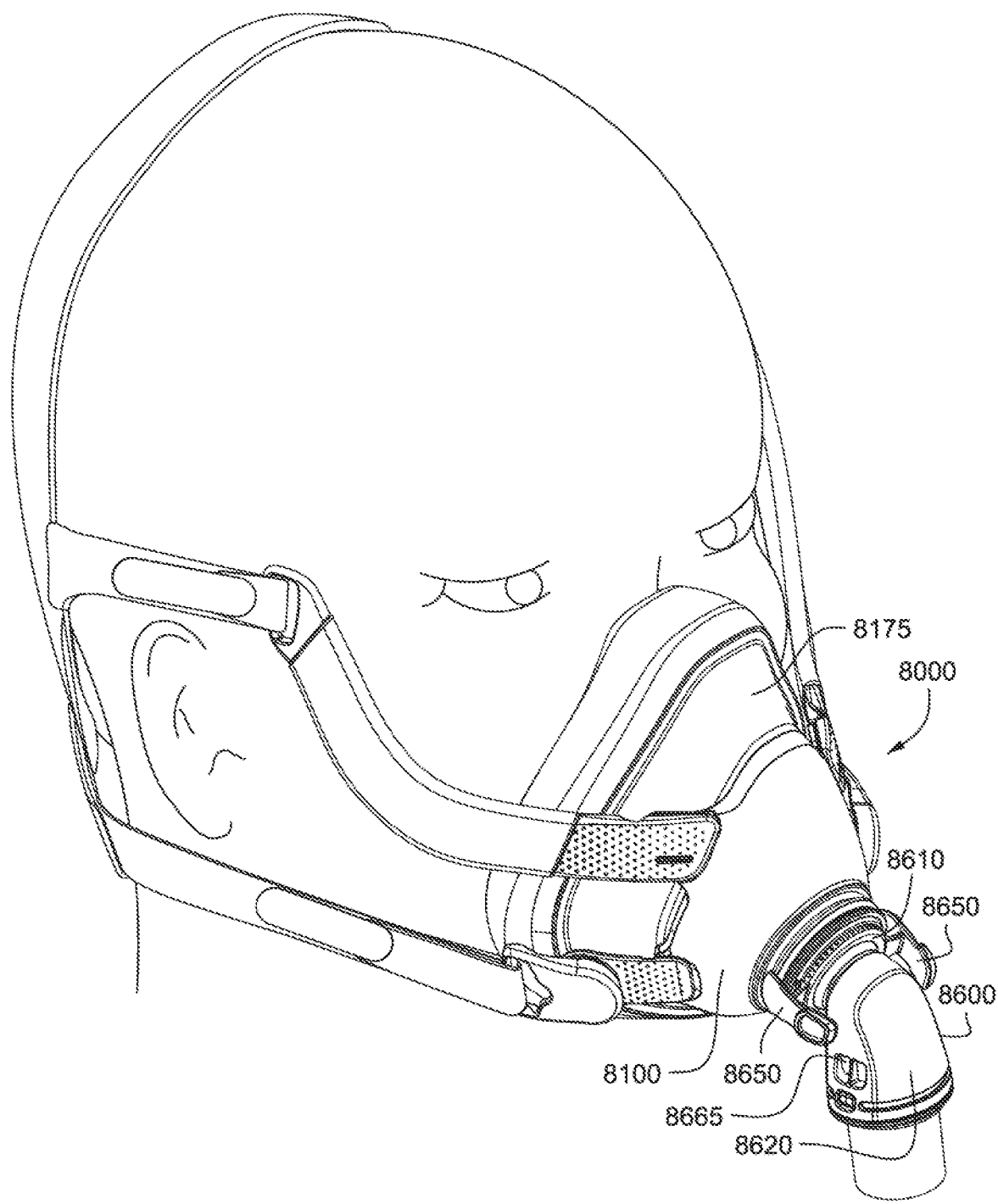

FIG. 48A is a perspective view of a patient interface shown on a patient's head including an elbow assembly according to an example of the present technology.

Figure 48B:
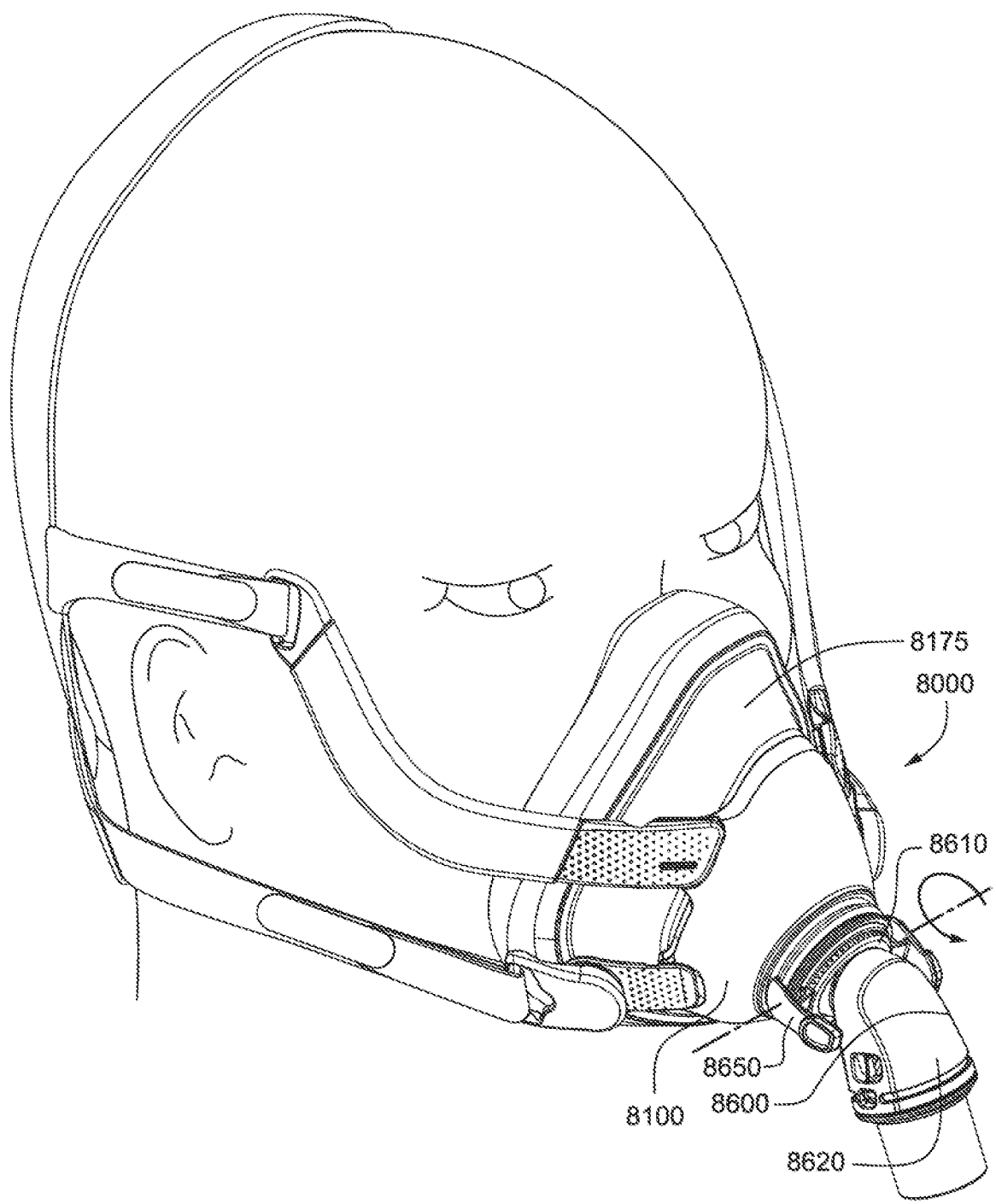

FIG. 48B is a perspective view of the patient interface shown in FIG. 48A with the elbow component of the elbow assembly pivoted upwards relative to the elbow component of the elbow assembly shown in FIG. 48A.

Figure 48C:
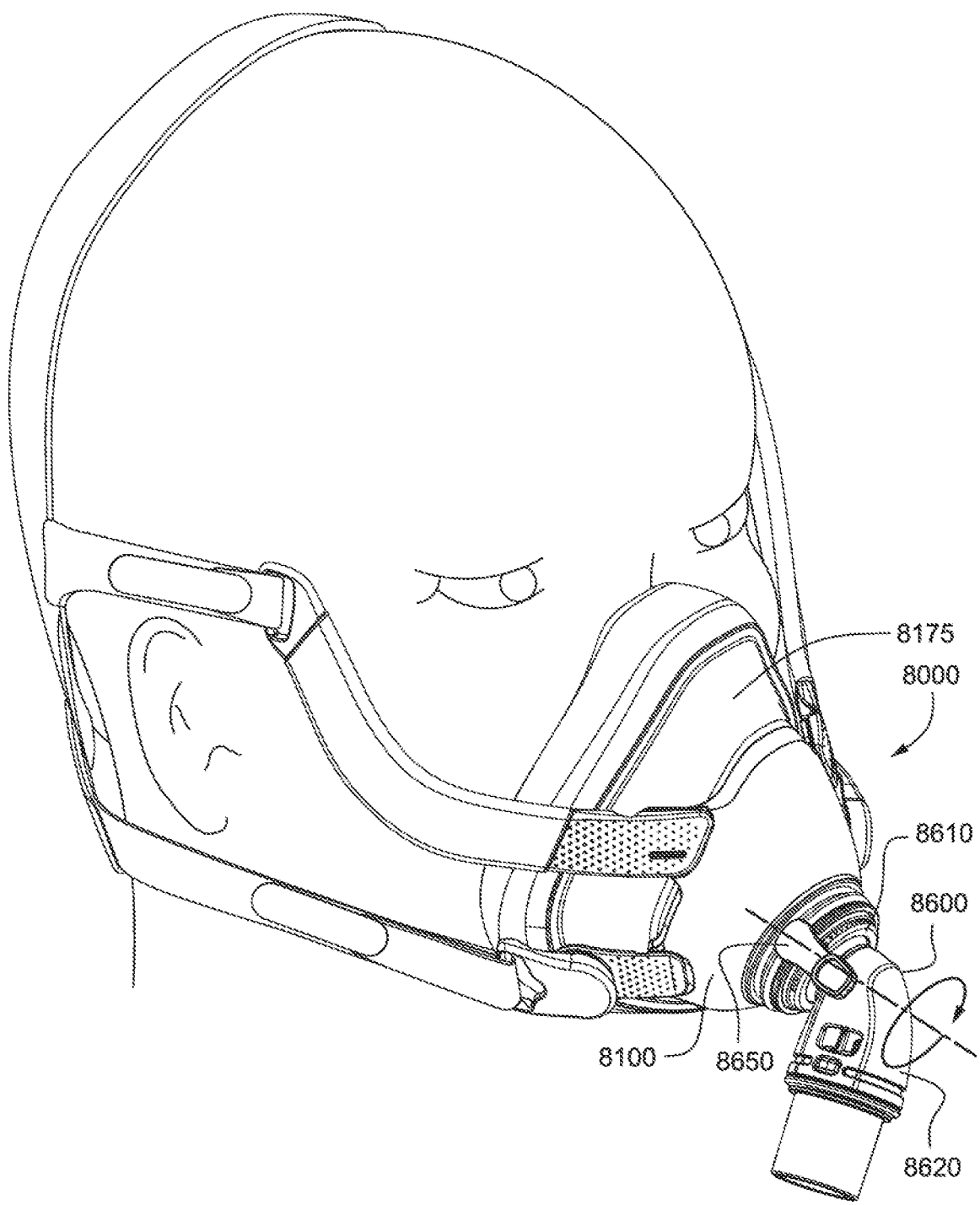

FIG. 48C is a perspective view of the patient interface shown in FIG. 48A with the elbow assembly rotated relative to the elbow assembly shown in FIG. 48A.

Figure 48D:
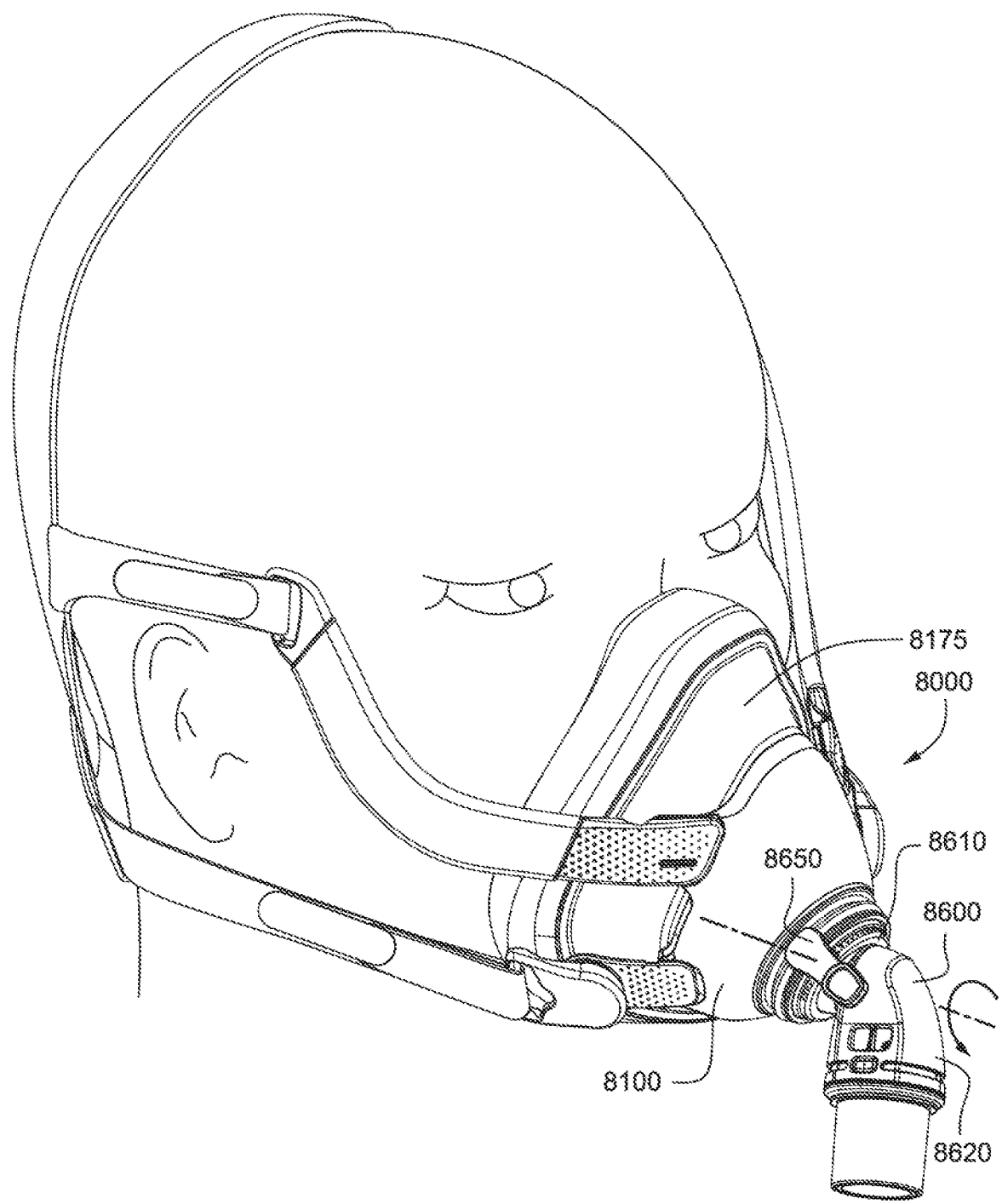

FIG. 48D is a perspective view of the patient interface shown in FIG. 48C with the elbow component of the elbow assembly pivoted upwards relative to the elbow component of the elbow assembly shown in FIG. 48C.

Figure 49:
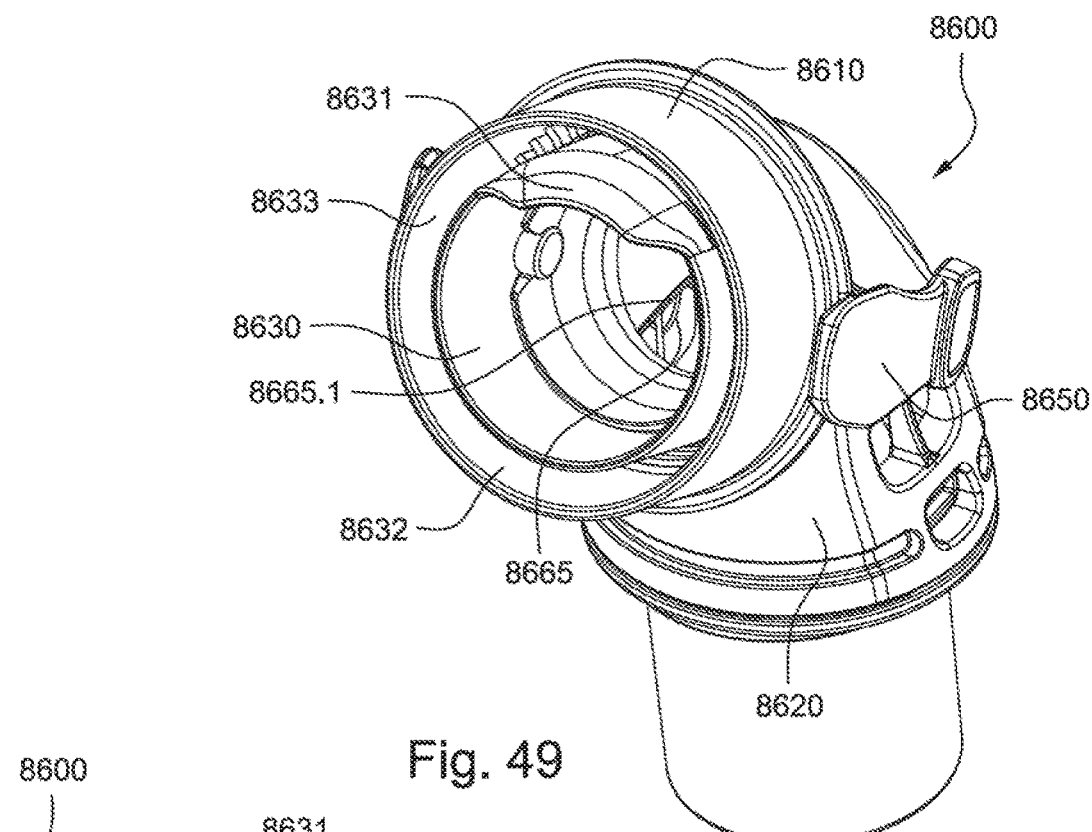

FIG. 49 is a rear perspective view of an elbow assembly according to an example of the present technology.

Figure 50:
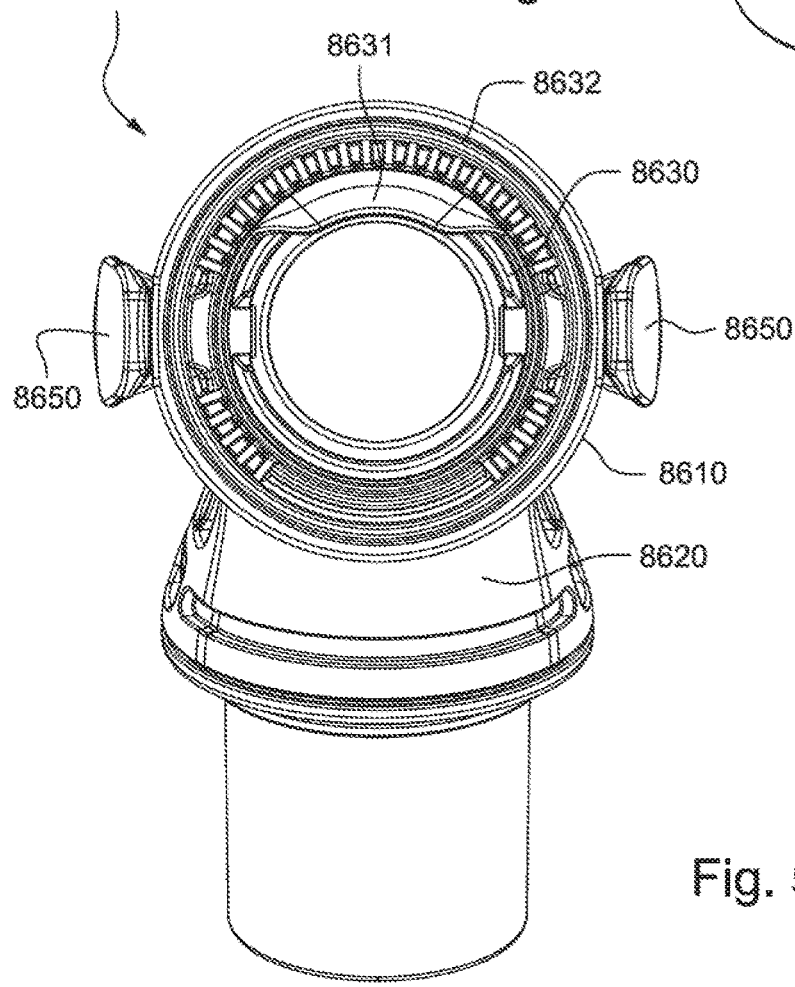

FIG. 50 is a rear view of the elbow assembly shown in FIG. 49.

Figure 51:
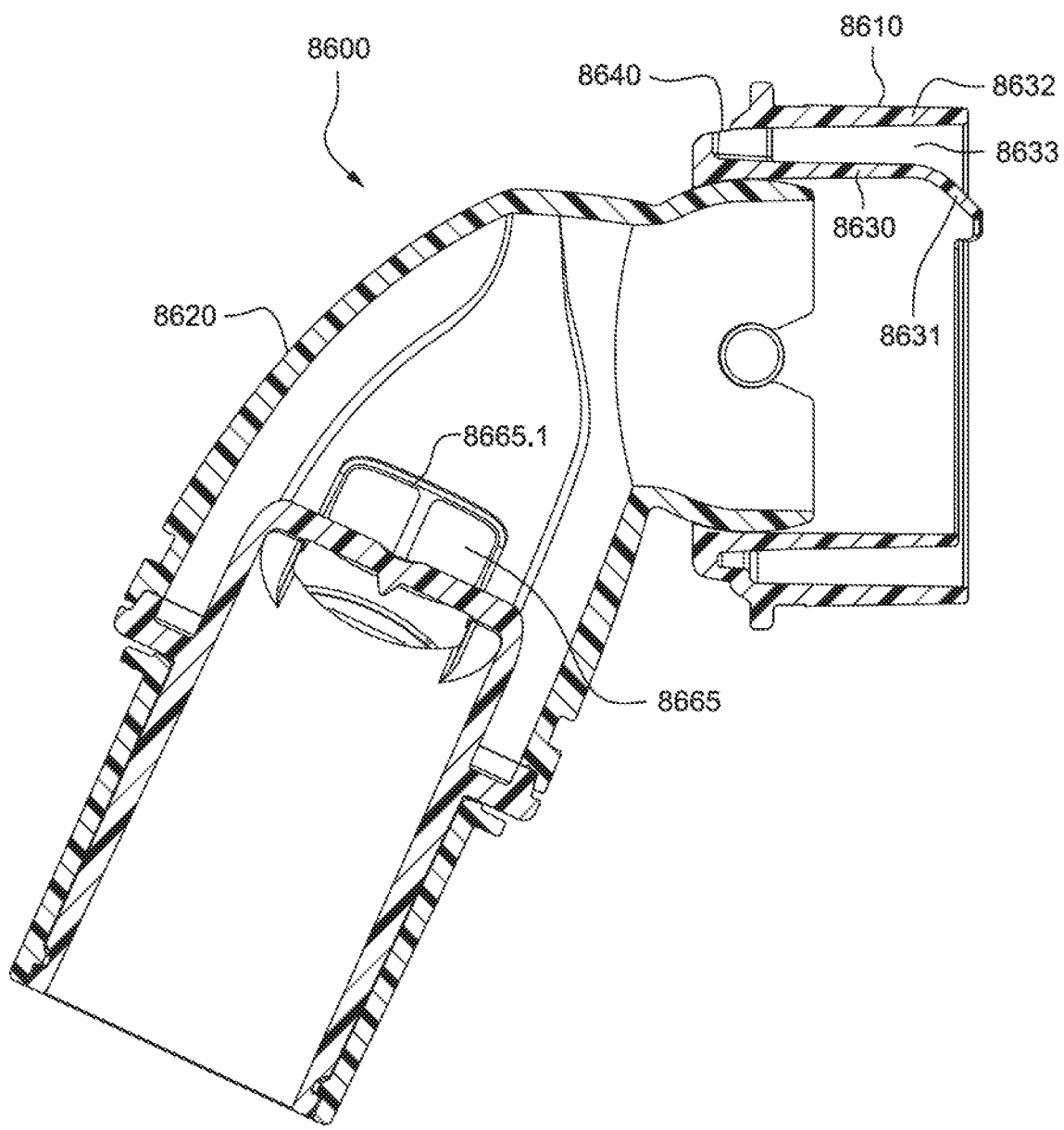

FIG. 51 is a cross-sectional view of the elbow assembly shown in FIG. 49.

Figure 52:
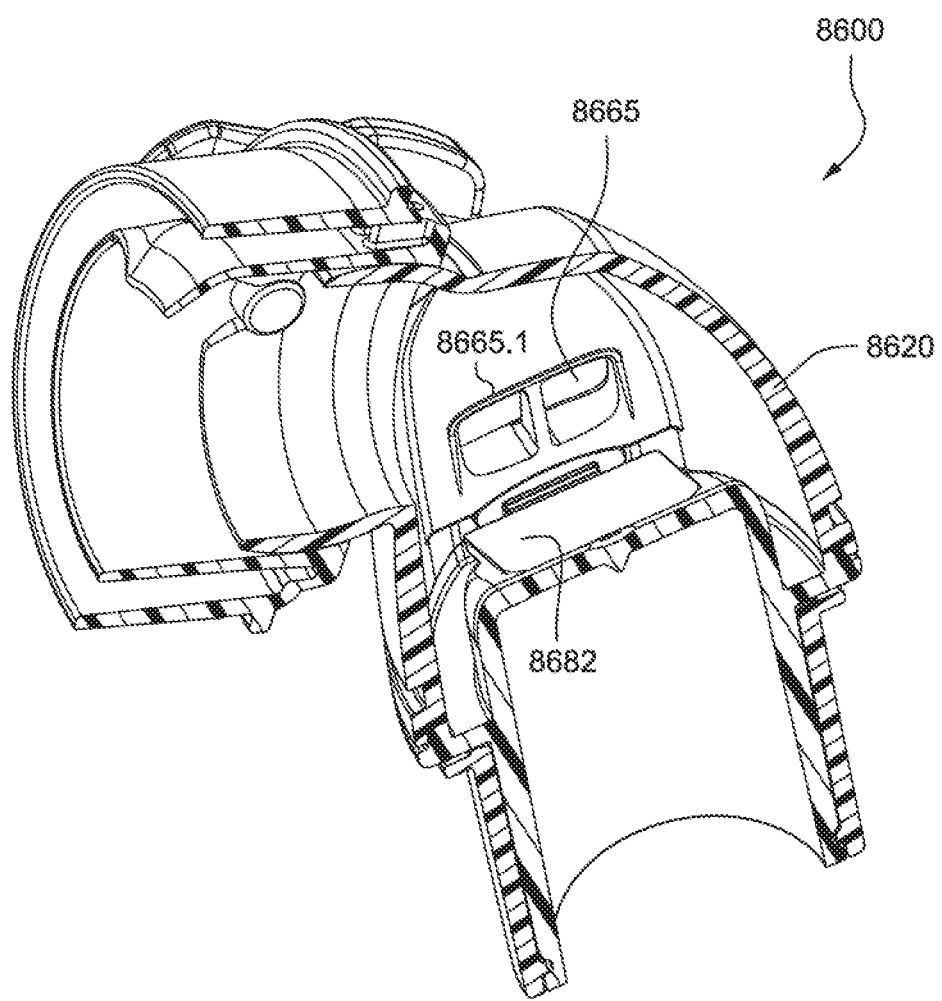

FIG. 52 is a cross-sectional view of the elbow assembly shown in FIG. 49, from a slight perspective angle.

Figure 53:
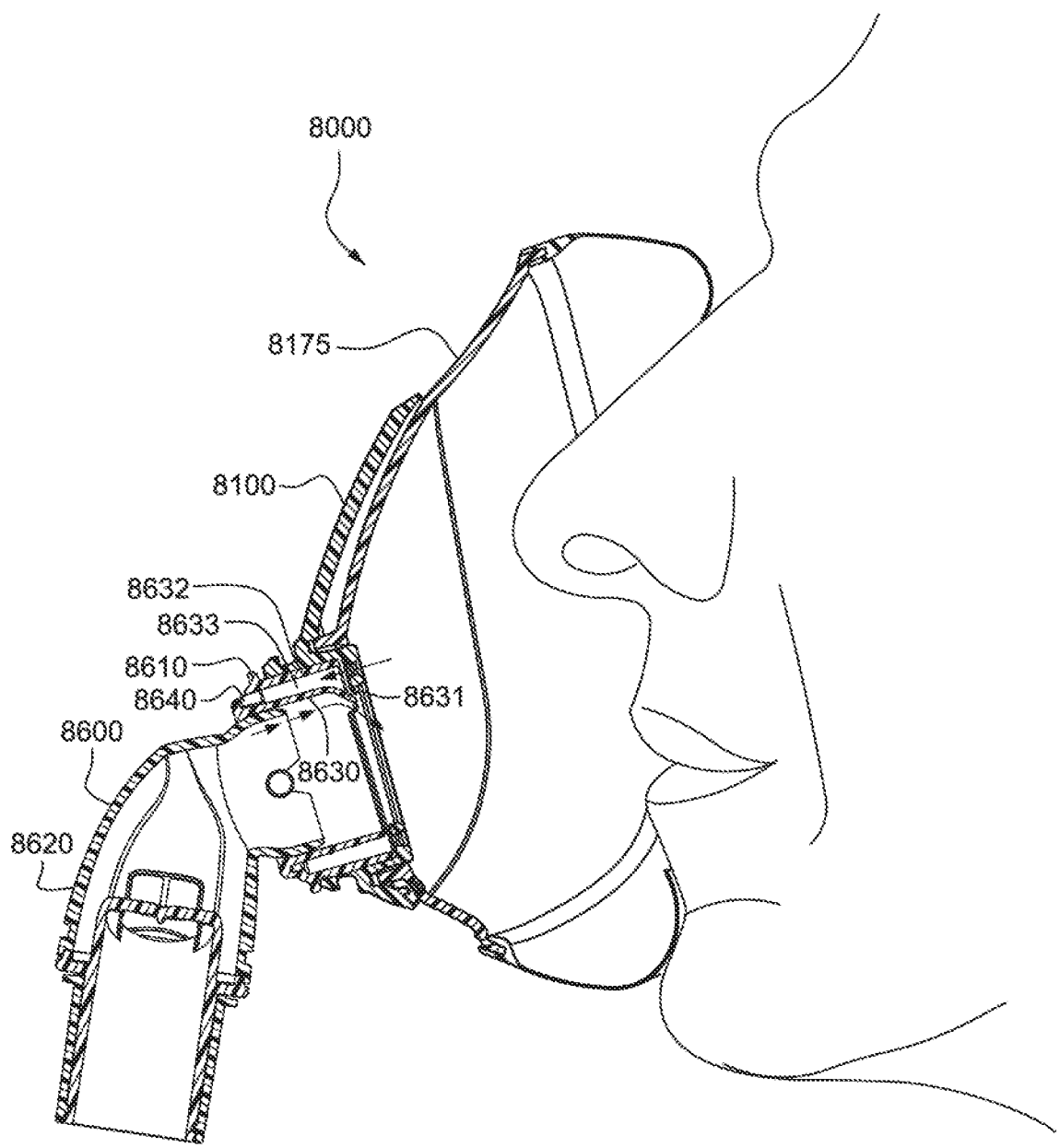

FIG. 53 is a cross-sectional view of a patient interface shown on a patient's head including the elbow assembly of FIG. 49 according to an example of the present technology.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 Treatment Systems

Figure 1A:
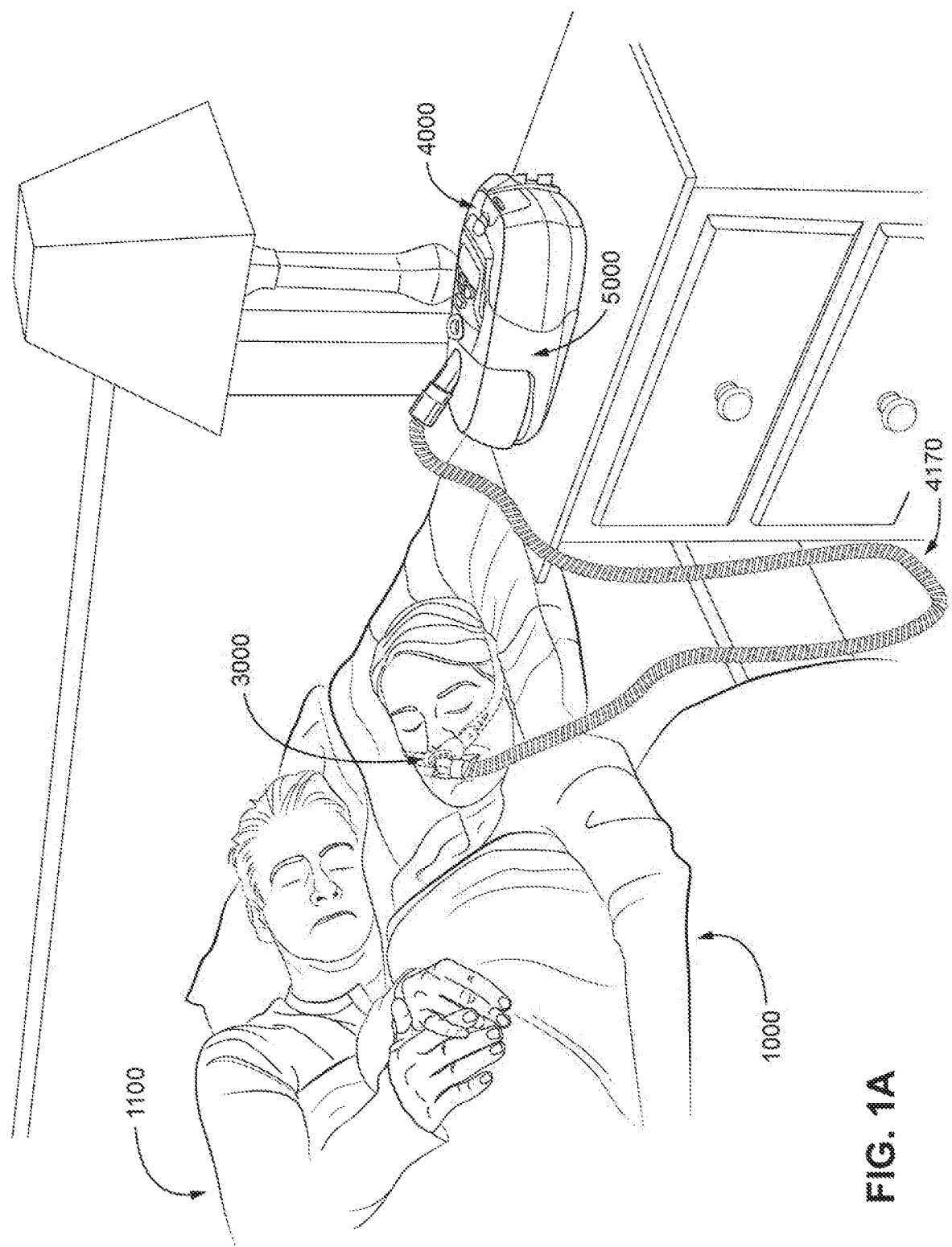
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receiving a supply of air at positive pressure from an RPT device 4000. Air from the RPT device 4000 is humidified in a humidifier 5000, and passes along an air circuit 4170 to the patient 1000.
Figure 1B:
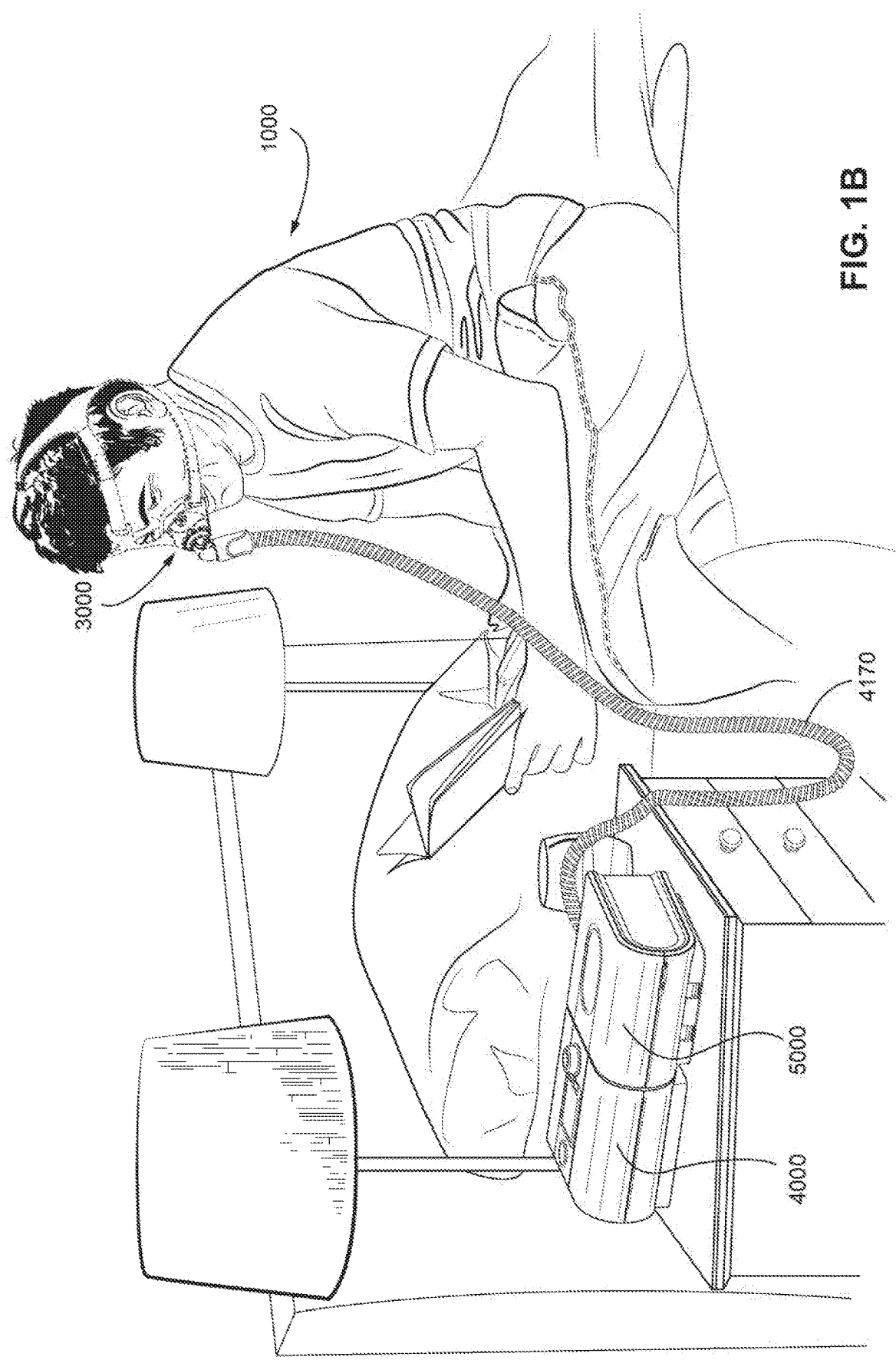
Figure 1C:

In one form, the present technology comprises an apparatus or device for treating a respiratory disorder. The apparatus or device may comprise an RPT device 4000 for supplying pressurised air to the patient 1000 via an air circuit 4170 to a patient interface 3000, e.g. see FIGS. 1A to 1C.

4.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

FIGS. 4 to 11 show a non-invasive patient interface 6000 in accordance with one aspect of the present technology comprising a frame assembly 6100, a cushion assembly 6175 including a seal-forming structure 6200, an elbow assembly 6600, and a positioning and stabilising structure (e.g., headgear 6800). FIG. 4 is an exemplary view of the patient interface 6000 on a patient's head, FIGS. 5 to 11 are exemplary views of the patient interface 6000 without headgear 6800, and FIGS. 12 to 24 are exemplary views of the elbow assembly 6600 according to an example of the present technology. In use, one form of the seal-forming structure 6200 is arranged to surround an entrance to the airways of the patient 1000 so as to facilitate the supply of air at positive pressure to the airways. The seal-forming structure 6200 (e.g., constructed of silicone) may also be commonly referred to as a cushion. In some forms, a functional aspect may be provided by one or more physical components. In some forms, one physical component may provide one or more functional aspects.

In one form of the present technology, the frame assembly 6100 connects as an intermediate component to the cushion assembly 6175 and the elbow assembly 6600. For example, the elbow assembly 6600 connects to the frame assembly 6100 (via a retention feature on the frame assembly) independently of the cushion assembly 6175 (e.g., see FIG. 8). However, the seal for the air flow path is formed between the elbow assembly 6600 and the cushion assembly 6175, i.e., the frame assembly 6100 is not in the air flow path (e.g., see FIGS. 9, 10, and 11).

In the example shown, the patient interface is a full-face/oro-nasal interface type including a seal-forming structure 6200 structured to form a seal around the patient's nose and mouth. However, aspects of the present technology may be adapted for use with other suitable interface types, e.g., nasal interface, nasal prongs.

Elbow Assembly

As shown in FIGS. 4 to 24, the elbow assembly 6600 includes a swivel component 6610 that is repeatedly engageable with and removably disengageable from the frame assembly 6100 of the patient interface 6000 and an elbow component 6620 adapted to connect to the air circuit 4170, e.g., via a swivel connector 6625.

The swivel component 6610 is coupled to the elbow component 6620 by a ball and socket joint and a hinge joint which allows the elbow component 6620 to pivot relative to the swivel component 6610 about a single axis, i.e., the elbow component 6620 is prevented from rotating relative to the swivel component 6610 in a plurality of axes by the hinge joint.

FIGS. 25 to 47 illustrate an elbow assembly 7600 according to another example of the present technology. The elbow assembly 7600 includes swivel component 7610, elbow component 7620, and swivel connector 7625, with the swivel component 7610 coupled to the elbow component 7620 as described above by a ball and socket joint and a hinge joint which allows the elbow component 7620 to pivot relative to the swivel component 7610 about a single axis.

FIGS. 48A to 53 show a patient interface 8000 and an elbow assembly 8600 according to another example of the present technology. The elbow assembly 8600 is substantially similar to the elbow assembly 7600, i.e., elbow assembly 8600 includes swivel component 8610 coupled to elbow component 7620 by a ball and socket joint and a hinge joint. In contrast, the swivel component 8610 of the elbow assembly 8600 comprises structure to redirect flow in a manner that reduces noise and/or minimizes flow directly onto sensitive parts of the patient's face as described in greater detail below.

Vent Arrangement

In the illustrated example of FIGS. 4 to 24, the swivel component 6610 includes a swivel member 6612, a diffuser material 6614, and a diffuser cover 6616. The swivel member 6612 includes an inner wall 6630, an outer wall 6632, and a base wall 6634 between the inner and outer walls 6630, 6632. A plurality of vent holes 6640 are provided along the base wall 6634 (e.g., at least 30 vent holes, e.g., 30 to 60 vent holes) to permit the exit of exhausted gases from the patient interface. As illustrated, the vent holes 6640 are arranged to define a substantially circular shape that rings around the opening 6635 defined by the inner wall 6630. In an example, each hole 6640 may include a contour or taper along its length, e.g., each hole converges in the direction of exhausted gas.

The inner and outer walls 6630, 6632 define a channel (annular depression) adapted to receive or house the diffuser material 6614 such that the diffuser material 6614 is positioned adjacent an outlet end of the each of the vent holes 6640. The diffuser cover 6616 is connected to the swivel member 6612 to retain the diffuser material 6614 within the channel. The diffuser cover 6616 includes a top wall and spaced apart side walls each including a retaining structure structured to secure the diffuser cover 6616 to the swivel member 6612 (e.g., diffuser cover permanently attached to the swivel member). The spaced apart side walls define openings or outlets 6618 therebetween that allow exhausted gases to vent to atmosphere. Specifically, the swivel component 6610 provides a vent flow path that passes through the vent holes 6640, through the diffuser material 6614 within the channel, and exits to atmosphere via the outlets 6618 of the diffuser cover 6616. Such arrangement allows exhaust gas to be directed radially outwardly from the elbow assembly, i.e., diffuser cover 6616 redirects flow passing through the diffuser material 6614.

In an alternative example, the elbow assembly may be provided without diffuser material. For example, as shown in the example of FIGS. 25 to 47, the swivel component 7610 includes an inner radial wall 7630, an outer radial wall 7632, and a base wall 7634 between the inner and outer radial walls 7630, 7632. The inner and outer radial walls 7630, 7632 define a radial channel 7633 leading to a plurality of vent holes 7640 (e.g., at least 20 vent holes, e.g., 20 to 60 vent holes) provided along the outer radial wall 7632 to permit the exit of exhausted gases from the patient interface to atmosphere. As illustrated, the vent holes 7640 are arranged along the outer radial wall 7632 to allow exhaust gas to be directed radially outwardly from the elbow assembly 7600.

As best shown in FIGS. 30, 35, 36, 39, 42, and 43, tracks or guide walls 7637 are provided within the channel 7633 proximate each vent hole 7640 to provide discrete flow paths that direct exhaust gases to the vent holes 7640. In the illustrated example, each track or guide wall 7637 extends radially between the inner and outer walls 7630, 7632 and cooperate to define flow paths or passageways 7639 leading to each vent hole 7640, i.e., each vent hole 7640 includes an associated passageway 7639 provided by the tracks or guide walls 7637.

In the illustrated embodiment, the vent holes 7640 and associated passageways 7639 are only provided along a portion of a perimeter of the elbow assembly, e.g., to accommodate pinch arms 7650 and/or avoid gas washout being directed into the pinch arms 7650. As illustrated, the swivel component 7610 includes vent holes 7640 along an upper or superior portion of its perimeter and along sides of a lower or inferior portion of its perimeter. However, it should be appreciated that vent holes may be provided along the entire perimeter of the swivel component 7610 or one or more selected portions of its perimeter.

In the illustrated example, as best shown in FIGS. 40 to 43, each vent hole 7640 and associated passageway 7639 includes a generally U-shaped cross-sectional shape, e.g., arched opening including generally rectangular shape with one of the shorter walls having a contour. However, each vent hole 7640 and associated passageway 7639 may have other suitable shapes to direct exhaust or washout gas.

In use, the inner radial wall 7630 projects posteriorly to function as a baffle and segregate the flow path of incoming pressurized air from the RPT device from the flow path of exhaust via the vent, e.g., to reduce cyclic noise. Exhaust gas flows into the channel 7633 and then into the passageways 7639 associated with respective vent holes 7640. As best shown in FIGS. 35, 36, and 39, the base wall 7634 at the end of each passageway 7639 is curved so as to more smoothly guide exhaust flow from a generally axial direction as its travels down the passageway 7639 to a generally radial direction as it exits the vent hole 7640 to atmosphere.

Similar to elbow assembly 7600 described above, the swivel component 8610 of elbow assembly 8600 includes an inner radial wall 8630 and an outer radial wall 8632 that define a radial channel 8633 leading to a plurality of vent holes 8640 (e.g., at least 20 vent holes, e.g., 20 to 60 vent holes) provided along the outer radial wall 8632 to permit the exit of exhausted gases from the patient interface to atmosphere (e.g., as best shown in FIGS. 49 to 53).

However, in the example of FIGS. 49 to 53, at least a portion of the inner radial wall 8630 includes an inwardly extending lip or chevron 8631 structured and arranged to redirect flow in a manner that reduces noise and/or minimizes flow directly onto sensitive parts of the patient's face.

In the illustrated example, the lip or chevron 8631 curves and extends inwardly from the inner radial wall 8630 towards the flow path of incoming pressurized air. As illustrated, the lip or chevron 8631 is provided along an upper or superior portion of the perimeter of the inner wall 8630 (e.g., see FIGS. 49 and 50). However, it should be appreciated that the lip or chevron 8631 may be provided along the entire perimeter of the inner wall 8630 or one or more selected portions of the inner wall's perimeter.

In use, as best shown in FIG. 53, the inner radial wall 7630 and the lip or chevron 8631 segregate the inlet flow of incoming pressurized air from the outlet flow of exhaust via the vent. Moreover, the lip or chevron 8631 is structured and arranged to redirect the inlet flow away from the outlet flow such that wind shearing and turbulence associated noise is reduced, e.g., vent noise is reduced by deflecting the air which generally hugs the top quadrant of the elbow assembly (avoids air/wind shear). In an example, the lip or chevron 8631 is structured and arranged to minimize frizzling, e.g., sizzling or sputtering noise from air flow.

In addition, as best shown in FIG. 53, the lip or chevron 8631 is structured and arranged to redirect the inlet flow away from sensitive parts of the patient's face such as the nose tip or pronasal, e.g., which is known to cause a tickling sensation.

Pinch Arms

In the example of FIGS. 4 to 24, the swivel member 6612 includes a pair of resilient, quick release pinch arms 6650, i.e., cantilevered spring arms or pinch buttons. Each of the spring or pinch arms 6650 includes a barbed end or tab 6652 structured to provide a mechanical interlock, e.g., snap-fit connection, with the frame assembly 6100.

In the example of FIGS. 25 to 47, the hinging portion 7655 of each pinch arm 7650 includes a generally trapezoidal or tapered shape along its length (e.g., see FIGS. 29, 40, and 44, i.e., the width of the hinging portion 7655 at its connection to the main body of the swivel component 7610 is larger than the width of the hinging portion at its connection to the pinch arm 7650. Such shape of the hinging portion 7655 allows ease of use, e.g., facilitates flexing of the pinch arm 7650 while maintaining sufficient bias for retention and allowing rotational movement on the frame assembly.

Also, the clearance or spacing C (e.g., see FIGS. 29 and 38) between each pinch arm 7650 and the elbow component 7620 is tuned such that the elbow component 7620 acts as a stop to prevent each pinch arm 7650 from being pressed too far inwards towards the elbow component 7620, which ensures that each pinch arm 7650 returns to its original position for retaining the elbow assembly onto the frame assembly.

Each spring arm 7650 includes the barbed end or peg-catch 7652 structured to provide the snap-fit connection with the frame assembly. Also, each spring arm 7650 includes a finger grip portion 7657, e.g., square-shaped protrusion, adjacent a free end.

In the illustrated example, the swivel component 7610 may be comprised of a material (e.g., Polybutylene terephthalate (PBT) such as Pocan) that is more flexible and resilient than a material of the elbow component 7620 (e.g., polycarbonate such as Makrolon), which material facilitates flexing of the spring arms 7650 in use.

Similar to elbow assembly 7600 described above, in the example of FIGS. 48A to 53, the swivel component 8610 of the elbow assembly 8600 includes a pair of resilient, quick release pinch arms 8650 structured to provide a mechanical interlock, e.g., snap-fit connection, with the frame assembly 8100 of the patient interface 8000.

Inner and Outer Walls of Swivel Member

In the example of FIGS. 4 to 24, the inner wall 6630 of the swivel member 6612 defines opening 6635 which provides the socket for the ball and socket joint. In addition, a pair of opposed, protruding, and cylindrical pivot pins or pegs 6645 extend from the inner wall 6630 into the opening 6635 for forming a hinge connection for the hinge joint.

Also, in the illustrated example of FIGS. 4 to 24, the outer wall 6632 is structured to extend through the frame assembly 6100 and form a seal with the cushion assembly 6175.

Similarly, the inner wall 7630 of swivel component 7610 defines opening 7635 which provides the socket for the ball and socket joint. Also, cylindrical pivot pins or pegs 7645 extend from the inner wall 7630 for forming a hinge connection for the hinge joint. However, as described below, in the example of FIGS. 25 to 47, the outer wall 7632 is structured to engage and form a hard-to-hard connection and seal with the frame assembly 7100 (see FIG. 47).

First and Second Ends of Elbow Component

In the illustrated example of FIGS. 4 to 24, the elbow component 6620 includes a first end 6660 provided to the swivel member 6612 and a second end 6670. The second end 6670 is provided with the swivel connector 6625 (e.g., swivel connector permanently connected to the second end) adapted to connect to the air circuit 4170. In this example, the swivel connector 6625 is overmolded to the tubular end portion 6671 of the second end 6670 (e.g., see FIG. 21). As illustrated, the tubular end portion 6671 defines a channel to receive and axially retain the swivel connector 6625 on the second end 6670.

The elbow component 7620 in FIGS. 25 to 47 includes a first end 7660 provided to the swivel component 7610 and a second end 7670 provided with the swivel connector 7625. In this example, the elbow component 7620 and the swivel connector 7625 comprise separately molded components that are subsequently mechanically connected to one another, e.g., snap-fit connection. For example, the swivel connector 7625 may be comprised of a material (e.g., Polybutylene terephthalate (PBT) such as Pocan) that is more flexible than a material of the elbow component 7620 (e.g., polycarbonate such as Makrolon), thereby allowing the swivel connector 7625 to flex over the tubular end portion 7671 of the second end 7670 of the elbow component 7620. The tubular end portion 7671 of the second end 7670 includes a groove 7671A along its outer surface adapted to receive a tongue 7626 provided along an interior surface of the swivel connector 7625 (e.g., see FIG. 35), i.e., snap-fit tongue and groove for swivelling connection. The connection between the elbow component 7620 and the swivel connector 7625 also provides a tortuous path therebetween to control and minimize leak.

Ball and Socket Joint and Hinge Joint

The first end 6660 of the elbow component 6620 includes a ball portion 6662 which provides the ball for the ball and socket joint. In addition, the ball portion 6662 includes a pair of opposed recesses 6664 for forming a hinge connection for the hinge joint.

The ball portion 6662 is engaged within the opening 6635 of the swivel member 6612 to form the ball and socket joint and the recesses 6664 are engaged with respective pivot pins 6645, e.g., with a snap-fit, to form the hinge joint.

Similarly, the ball portion 7662 of the elbow component 7620 is engaged within the opening 7635 of the swivel component 7610 to form the ball and socket joint, and the opposed recesses 7664 are engaged with respective pivot pins 7645, e.g., with a snap-fit, to form the hinge joint. As illustrated, the opening 7635 includes a rim 7636 (e.g., see FIGS. 35 and 44) which further retains the ball portion 7662 within the opening 7635.

In the example of FIGS. 25 to 47, each recess 7664 (also referred to as a peg engaging portion structured to engage with a respective pivot pin or peg 7645) includes tapered sides leading to a generally circular opening which configuration is structured to resiliently expand to engulf or more substantially enclose the pivot pin 7645 during engagement. This type of engagement is structured to limit relative movement between the ball portion 7662 and the opening 7635 of the ball and socket joint, thereby providing a controlled clearance between the exterior surface provided by the ball portion 7662 and the interior surface provided by the opening 7635. The controlled clearance allows any leak between the ball portion 7662 and the opening 7635 to be relatively the same in any relative configuration between the swivel component 7610 and the elbow component 7620, thereby allowing predictable leak which facilitates tuning of the vent arrangement.

AAV Assembly

The first and second ends 6660, 6670 (e.g., constructed of polycarbonate such as Makrolon) of the elbow component 6620 are coupled to one another (e.g., permanently connected) and structured to house a dual flap, anti-asphyxia valve (AAV) assembly including a pair of AAVs 6680 (e.g., constructed of liquid silicone rubber (LSR)). The first end 6660 includes a pair of ports 6665 that may be selectively closed by respective flap portions 6682 of the AAVs 6680. If pressurized gas provided to the elbow assembly is of sufficient magnitude, the flap portions 6682 of the AAVs 6680 will raise to block off the ports 6665. In this case, pressurized gas will be guided through the elbow assembly for delivery to the patient interface and the patient's airways. If pressurized gas is not of sufficient magnitude or not delivered, the flap portions 6682 will remain in the "rest" position (e.g., see FIGS. 21 and 24) so that the patient can breathe in ambient air and exhale through the ports 6665.

The first end 6660 includes a pair of openings 6667, just below respective ports 6665, that are structured to secure the AAVs 6680 within the elbow component. Each AAV 6680 includes a connecting portion 6684 structured to lockingly engage within a corresponding opening 6667, e.g., mechanical interlock. Each flap portion 6682 is movably provided, e.g., hingedly connected by a hinge portion, to the connecting portion 6684 which allows the flap portion 6682 to pivot to selectively close the port 6665.

The second end 6670 includes a base wall 6672 that defines an interior opening selectively closed by respective flap portions 6682 of the AAVs 6680. One or more ribs 6675 extend from the base wall 6672 into the opening to define stops for the flap portions 6682. In the illustrated example, the base wall 6672 includes wall portions 6672A, 6672B (e.g., see FIGS. 20 and 24) oriented at an angle with respect to one another, which orients the flap portions 6682 at an angle with respect to one another when in the "rest" position (e.g., see FIG. 24).

Similarly, the first and second ends 7660, 7670 (e.g., constructed of polycarbonate such as Makrolon) of the elbow component 7620 are coupled to one another and structured to house a pair of AAVs 7680. The first end 7660 includes a pair of ports 7665 that may be selectively closed by respective flap portions 7682 of the AAVs 7680 as described above. FIG. 37 shows the flap portions 7682 in the "rest" position. Each AAV 7680 includes a connecting portion 7684 structured to lockingly engage within a corresponding opening 7667 in the first end 7660, e.g., mechanical interlock.

As best shown in FIGS. 33, 34, and 46, the second end 7670 includes a base wall 7672 that defines a pair of openings or therapy ports 7673 selectively closed by respective flap portions 7682 of the AAVs 7680. The openings 7673 are separated by a bridge 7674 which prevents the flap portions 7682 from contacting each other, thereby preventing friction from interference between the flap portions 7682. Moreover, the bridge 7674 prevents any gaps being formed between the flap portions 7682 to prevent exhausted gas escaping through the openings 7673 when the flap portions 7682 are in the "rest" position.

A rib 7675 extends from each side of the bridge 7674 into respective openings 7673 to define stops for the flap portions 7682, e.g., prevent flap portions 7682 from traveling below the bridge 7674 and sticking.

In the illustrated example, the base wall 7672 includes wall portions 7672A, 7672B (e.g., see FIG. 46) oriented at an angle with respect to one another, which orients the flap portions 7682 at an angle with respect to one another when in the "rest" position. Such arrangement pre-loads or pre-bends the flap portions 7682 such that the flap portions 7682 maintain a minimum force against the rim or edge (i.e., sealing surfaces) of the openings 7673 to block the openings 7673 when pressurized gas is not being delivered. The flap portions 7682 are structured such that they completely block the openings 7673 in the instance that therapy pressure ceases. This complete blockage prevents any exhaust gases from flowing through the openings 7673 and then subsequently rebreathed by the patient (i.e., all exhausted gas exits via the AAV ports 7665). Also, the pre-loaded configuration maintains the flap portions 7682 in the rest or closed position during movement of the entire elbow assembly (i.e., resists opening during movement or under gravity).

The hinge portion 7685 that pivotally or hingedly connects the flap portion 7682 to the connecting portion 7684 (e.g., see FIGS. 34 and 37) may be tuned to easily open under therapy pressure and completely block the AAV ports 7665.

FIGS. 49, 51 and 52 show an additional feature of the elbow connection, showing a rim 8665.1 that at least partially surrounds the port 8665. The rim surrounds three sides of the port in this example, and has a tapering thickness along its two depending legs. The rim 8665.1 is positioned and dimensioned to come into contact with a flap 8682 of a corresponding AAV if the elbow is pressurised. The rim minimizes surface area contact of the AAV with the inner wall of the elbow to minimise the risk of said AAV sticking to the inner wall. Sticking of the AAV to the inner wall of the elbow may cause the ports to remain blocked even when therapy pressure ceases.

Connection of First and Second Ends of Elbow Component

In an example, the first and second ends of the elbow component 6620, 7620 may be coupled to one another by ultrasonic welding to permanently connect the first and second ends. In such arrangement, the first and second ends may include structure to facilitate orientation and welding of the first and second ends.

In an example, as best shown in FIGS. 34 and 45, the first end 7660 of elbow component 7620 includes elongated support grooves 7690 along its outer perimeter which are adapted to be engaged with a welding nest that positions and supports the first end 7660 during the ultrasonic welding process. Also, the first end 7660 of elbow component 7620 includes orientation features (e.g., opposing flat surfaces 7692 as shown in FIG. 45) along its inner perimeter to locate and align the second end 7670.

As best shown in FIG. 46, the second end 7670 of elbow component 7620 includes a welding bead 7695 structured to be ultrasonically welded to the inner perimeter of the first end 7660. As illustrated, the welding bead 7695 includes orientation features (e.g., opposing flat surfaces 7696) corresponding to orientation features (e.g., opposing flat surfaces 7692) of the first end 7660 to locate and align the welding bead 7695 within the inner perimeter of the first end 7660. Also, the second end 7670 provides a flat surface 7698 opposite the bead 7695 (e.g., see FIG. 35), which is adapted to be engaged with a welding horn that applies acoustic vibration to the second end 7670 during the ultrasonic welding process.

Assembly

In an example, assembly of the elbow assembly 7600 may comprise assembling the AAVs 7680 to the second end 7670 of the elbow component 7620, connecting the first and second ends 7660, 7670 of the elbow component 7620 (e.g., via ultrasonic welding), assembling the swivel connector 7625 to the second end 7670 of the elbow component 7620 (e.g., snap-fit connection), and then assembling the swivel component 7610 to the elbow component 7620 (e.g., snap-fit connection). However, it should be appreciated that assembly of the elbow assembly may comprise alternative steps and/or sequences.

Connection Between Elbow Assembly and Frame Assembly

The elbow assembly 6600 releasably connects to the frame assembly 6100 via the pinch arms 6650, e.g., quick release snap-fit. The frame assembly 6100 includes a circular channel 6120 which is structured to receive the barbed end 6652 of the pinch arms 6650 to releasably retain the elbow assembly 6600 to the frame assembly 6100 and form a swivel connection (e.g., see FIGS. 7 and 9), i.e., allow 360° free rotation of the elbow assembly 6600 relative to the frame assembly 6100 about the axis of the circular channel (e.g., see arrow in FIG. 6).

As best shown in FIG. 47, the pinch arms 7650 of the elbow assembly 7600 releasably connect to frame assembly 7100 in a similar manner, i.e., barbed end 7652 of the pinch arms 7650 engage within circular channel 7120 of frame assembly 7100, e.g., quick release snap-fit, to releasably retain the elbow assembly 7600 to the frame assembly 7100 and form the swivel connection.

In the illustrated example, the swivel component 7610 of the elbow assembly 7600 and the corresponding bore in the frame assembly 7100 communicating with the swivel component 7610 include a diameter (e.g., about 25-35 mm) that is larger than a diameter (e.g., about 22 mm) provided by the swivel connector 7625 adapted to connect to the air circuit or gas delivery tube.

Seal Between Elbow Assembly and Cushion Assembly

In the illustrated example of FIGS. 4 to 24, the cushion assembly 6175 comprises a flexible flange or lip seal 6250 to provide a seal with the elbow assembly 6600. As shown in FIGS. 10 and 11, the elbow assembly 6600 is structured to mechanically interlock with the frame assembly 6100, but is structured and arranged to sealingly engage with sealing membrane 6250 of the cushion assembly 6175 to form a seal for the air flow path, i.e., sealing mechanism is separate from the retention features.

As illustrated, the leading edge of the outer wall 6632 of the elbow assembly 6600 forms a face seal with the lip seal 6250. This form of engagement minimises surface area contact to reduce friction, thereby allowing a seal to form between the components while allowing the elbow assembly 6600 to swivel freely relative to the frame and cushion assemblies 6100, 6175.

In an alternative arrangement, the elbow assembly 6600 may form a substantially sealed engagement with the frame assembly 6100. The substantially sealed engagement between the frame assembly 6100 and the elbow assembly 6600 may allow the elbow assembly 6600 to swivel freely while maintaining a controlled level of leak through said substantially sealed engagement. In this arrangement, the frame assembly 6100 may form a separate sealed engagement with the cushion assembly 6175. Said arrangement allows the cushion assembly 6175 to be disengaged from the frame assembly 6100 independently of the elbow assembly 6600, which may be disengaged separately from the frame assembly 6100.

For example, as shown in FIG. 47, the elbow assembly 7600 is structured to establish a hard-to-hard connection and seal with the frame assembly 7100. As illustrated, a dynamic diametric seal is formed between the cylindrical outer surface 7632A of the outer wall 7632 of the elbow assembly 7600 and the inner surface 7115A of the annular flange 7115 of the frame assembly 7100. Also, the annular flange 7115 of the frame assembly 7100 comprises a radially inwardly extending ridge 7125 that acts as a stop to prevent over-insertion of the elbow assembly 7600 into the frame assembly 7100. The surface of the ridge 7125 also provides a dynamic face seal with the leading edge or surface 7632B of the outer wall 7632 of the elbow assembly 7600. The diametric seal and the face seal provided between surfaces 7632A, 7632B of the outer wall 7632 and surfaces of the annular flange 7115/ridge 7125 provide two mating surfaces of contact between the elbow assembly 7600 and the frame assembly 7100, which increases the surface area of contact between the elbow assembly 7600 and the frame assembly 7100. The two mating surfaces are configured and arranged to minimize and control leak by providing a tortuous leak path, i.e., leak path between the two mating surfaces extends radially to axially from interior the patient interface to atmosphere.

Also, as shown in FIG. 47, the frame assembly 7100 is structured to form a static diametric seal and a static face seal with the cushion assembly 7175 to minimize and control leak. As illustrated, the frame assembly 7100 includes a channel 7105 adapted to receive a connecting portion 7176 provided to the cushion assembly 7175. The leading edge 7176A of the connecting portion 7176 and the end wall 7105A of the channel 7105 are configured and arranged to provide a static face seal, and the outer side 7176B of the connecting portion 7176 and the side wall 7105B of the channel 7105 are configured and arranged to provide a static diametric seal.

Decoupling Arrangement

In the illustrated examples, the elbow assembly 6600, 7600, 8600 provides two distinct forms of decoupling to allow free rotation of the elbow assembly 6600, 7600, 8600 relative to the frame assembly 6100, 7100, 8100 and the cushion assembly 6175, 7175, 8175, e.g., to enhance the decoupling of tube drag on the patient interface to prevent seal instability.

The first form of decoupling is provided by the pinch arms 6650, 7650, 8650 which form the swivel connection allowing 360° free rotation of the elbow assembly 6600, 7600, 8600 relative to the frame assembly 6100, 7100, 8100 (e.g., see arrow in FIG. 6). Also, FIG. 48A shows an example of the elbow assembly 8600 in a first position and FIG. 48C shows an example of the elbow assembly 8600 rotated to a second position relative to the first position via the swivel connection.

The second form of decoupling is provided by the ball and socket joint and the hinge joint which allows the elbow component 6620, 7620, 8620 to pivot relative to the swivel component 6610, 7610, 8610 about a single axis, e.g., about the axis of the pivot pins 6645, 7645 (e.g., see arrow in FIG. 7). Also, FIG. 48A shows an example of the elbow assembly 8600 in a first position and FIG. 48B shows an example of the elbow assembly 8600 pivoted upwards to a second position relative to the first position via the ball and socket joint and the hinge joint. FIG. 48D also shows the elbow assembly rotated and pivoted upwards relative to the elbow assembly position shown in FIG. 48A. In an example, the ball and socket joint and the hinge joint provide a range of movement of about 10-30 degrees, e.g., range of movement of about 15 degrees, range of movement of about 25-30 degrees (e.g., 26 degrees). Such hinge connection between the elbow component 6620, 7620, 8620 and the swivel component 6610, 7610, 8610 prevents free swivelling or full 360 degree motion so as to prevent the elbow component 6620, 7620, 8620 from rotating into or contacting the pinch arms 6650, 7650, 8650 (e.g., which may inadvertently release the elbow assembly from the frame assembly). The hinge connection between the elbow component 6620, 7620, 8620 and the swivel component 6610, 7610, 8610 also allows the pivot pins 6645, 7645 to act as a stop for preventing complete insertion of the ball portion 6662, 7652 into the opening or socket 6635, 7635.

Thus, the elbow assembly 6600, 7600, 8600 as a whole is allowed to swivel relative to the frame and cushion assemblies 6100, 6175, 7100, 7175, 8100, 8175 while the elbow component 6620, 7620, 8620 is able to pivot relative to the swivel component 6610, 7610, 8610 in any swivel position of the elbow assembly 6600, 7600, 8600, i.e., the elbow component 6620, 7620, 8620 is able to pivot relative to the swivel component 6610, 7610, 8610 regardless of the orientation of the rotational position of the elbow assembly 6600, 7600, 8600 relative to the frame and cushion assemblies 6100, 6175, 7100, 7175, 8100, 8175.

4.3.1 Seal-Forming Structure

In one form of the present technology, a seal-forming structure provides a seal-forming surface, and may additionally provide a cushioning function.

A seal-forming structure in accordance with the present technology may be constructed from a soft, flexible, resilient material such as silicone.

In one form, the seal-forming structure comprises a sealing flange and a support flange. The sealing flange comprises a relatively thin member with a thickness of less than about 1 mm, for example about 0.25 mm to about 0.45 mm, that extends around the perimeter of the plenum chamber. Support flange may be relatively thicker than the sealing flange. The support flange is disposed between the sealing flange and the marginal edge of the plenum chamber, and extends at least part of the way around the perimeter. The support flange is or includes a spring-like element and functions to support the sealing flange from buckling in use. In use the sealing flange can readily respond to system pressure in the plenum chamber acting on its underside to urge it into tight sealing engagement with the face.

In one form the seal-forming portion of the non-invasive patient interface comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the non-invasive patient interface comprises a seal-forming portion that forms a seal in use on an upper lip region (that is, the lip superior) of the patient's face.

In one form the non-invasive patient interface comprises a seal-forming portion that forms a seal in use on a chin-region of the patient's face.

In certain forms of the present technology, a seal-forming structure is configured to correspond to a particular size of head and/or shape of face. For example one form of a seal-forming structure is suitable for a large sized head, but not a small sized head. In another example, a form of seal-forming structure is suitable for a small sized head, but not a large sized head.

4.3.2 Plenum Chamber

The plenum chamber has a perimeter that is shaped to be complementary to the surface contour of the face of an average person in the region where a seal will form in use. In use, a marginal edge of the plenum chamber is positioned in close proximity to an adjacent surface of the face. Actual contact with the face is provided by the seal-forming structure. The seal-forming structure may extend in use about the entire perimeter of the plenum chamber.

4.3.3 Positioning and Stabilising Structure

The seal-forming structure of the patient interface of the present technology may be held in sealing position in use by the positioning and stabilising structure.

In one form of the present technology, a positioning and stabilising structure is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure comprises at least one strap having a rectangular cross-section. In one example the positioning and stabilising structure comprises at least one flat strap.

In one form of the present technology, a positioning and stabilising structure comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilising structure comprises a strap that is bendable and e.g. non-rigid. An advantage of this aspect is that the strap is more comfortable for a patient to lie upon while the patient is sleeping.

In certain forms of the present technology, a positioning and stabilizing structure provides a retaining force configured to correspond to a particular size of head and/or shape of face. For example one form of positioning and stabilizing structure provides a retaining force suitable for a large sized head, but not a small sized head. In another example, a form of positioning and stabilizing structure provides a retaining force suitable for a small sized head, but not a large sized head.

4.3.4 Vent

In one form, the patient interface includes a vent constructed and arranged to allow for the washout of exhaled gases, e.g. carbon dioxide.

One form of vent in accordance with the present technology comprises a plurality of holes, for example, about 20 to about 80 holes, or about 40 to about 60 holes, or about 45 to about 55 holes.

The vent may be located in the plenum chamber. Alternatively, the vent is located in a decoupling structure, e.g., a swivel.

4.3.5 Decoupling Structure(s)

In one form the patient interface includes at least one decoupling structure, for example, a swivel or a ball and socket.

4.3.6 Connection Port

Connection port allows for connection to the air circuit 4170.

4.3.7 Forehead Support

In the illustrated example, the frame assembly 6100 is provided without a forehead support.

In another form, the patient interface may include a forehead support, e.g., the frame assembly may include a forehead support.

4.3.8 Anti-Asphyxia Valve

In one form, the patient interface includes an anti-asphyxia valve.

4.3.9 Ports

In one form of the present technology, a patient interface includes one or more ports that allow access to the volume within the plenum chamber. In one form this allows a clinician to supply supplemental oxygen. In one form, this allows for the direct measurement of a property of gases within the plenum chamber, such as the pressure.

4.4 Glossary

For the purposes of the present technology disclosure, in certain forms of the present technology, one or more of the following definitions may apply. In other forms of the present technology, alternative definitions may apply.

4.4.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory disease.

Pressure: Force per unit area. Pressure may be expressed in a range of units, including $cmH_2O$, $g-f/cm^2$ and hectopascal. 1 $cmH_2O$ is equal to 1 $g-f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

4.4.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a typically transparent thermoplastic polymer of Bisphenol-A Carbonate.

4.4.1.2 Mechanical Properties

Resilience: Ability of a material to absorb energy when deformed elastically and to release the energy upon unloading.

'Resilient': Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

'Floppy' structure or component: A structure or component that will change shape, e.g. bend, when caused to support its own weight, within a relatively short period of time such as 1 second.

'Rigid' structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

4.4.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory airflow rate, as opposed to "true respiratory flow rate" or "true respiratory airflow rate", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

4.4.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

4.4.4 Anatomy
4.4.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 4.4.4.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

4.4.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

4.4.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Functional Dead Space:

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

4.4.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a cushion structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

4.4.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

4.4.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

4.4.6.3 Space Curves

Space curves: Unlike a plane curve, a space curve does not necessarily lie in any particular plane. A space curve may be considered to be a one-dimensional piece of three-dimensional space. An imaginary person walking on a strand of the DNA helix walks along a space curve. A typical human left ear comprises a left-hand helix, see FIG. 3P. A typical human right ear comprises a right-hand helix, see FIG. 3Q. FIG. 3R shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3O), or alternatively by a left-hand rule (FIG. 3N).

Osculating plane: The plane containing the unit tangent vector and the unit principal normal vector. See FIGS. 3N and 3O.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3R, since T2>T1, the magnitude of the torsion near the top coils of the helix of FIG. 3R is greater than the magnitude of the torsion of the bottom coils of the helix of FIG. 3R With reference to the right-hand rule of FIG. 3O, a space curve turning towards the direction of the right-hand binormal may be considered as having a right-hand positive torsion (e.g. a right-hand helix as shown in FIG. 3R). A space curve turning away from the direction of the right-hand binormal may be considered as having a right-hand negative torsion (e.g. a left-hand helix).

Equivalently, and with reference to a left-hand rule (see FIG. 3N), a space curve turning towards the direction of the left-hand binormal may be considered as having a left-hand positive torsion (e.g. a left-hand helix). Hence left-hand positive is equivalent to right-hand negative. See FIG. 3S.

4.4.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by the plane curve 301D.

A structure may have a two-dimensional hole, e.g. a hole bounded by a surface. For example, an inflatable tyre has a two dimensional hole bounded by the inside surface of the tyre. In another example, a bladder with a cavity for air or gel could have a two-dimensional hole. See for example the cushion of FIG. 3L and the example cross-section there through in FIG. 3M. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by surface 302D.

4.5 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

For example, it should be appreciated that one or more features of any one elbow assembly example (e.g., elbow assemblies 6600, 7600, 8600) may be combinable with one or more features of another elbow assembly example (e.g., elbow assemblies 6600, 7600, 8600) or other examples related thereto. For example, one or more aspects of the elbow assembly 8600 (e.g., lip or chevron 8631) may be incorporated into the elbow assembly 6600, 7600.

Also, it should be appreciated that one or more aspects of the present technology may be combinable with one or more aspects of: PCT Application No. PCT/AU2016/050891, filed Sep. 23, 2016 and entitled "Patient Interface", which claims the benefit of U.S. Provisional Application No. 62/222,593, filed Sep. 23, 2015 and U.S. Provisional Application No. 62/376,961, filed Aug. 19, 2016; U.S. Provisional Application No. 62/377,217, filed Aug. 19, 2016 and entitled "Patient Interface with a Seal-Forming Structure having Varying Thickness"; U.S. Provisional Application No. 62/377,158, filed Aug. 19, 2016 and entitled "Patient Interface with a Seal-Forming Structure having Varying Thickness"; PCT Application No. PCT/AU2016/050893, filed Sep. 23, 2016 and entitled "Vent Adaptor for a Respiratory Therapy System", which claims the benefit of U.S. Provisional Application No. 62/222,604, filed Sep. 23, 2015; and/or PCT Application No. PCT/AU2016/050228 filed Mar. 24, 2016 and entitled "Patient Interface with Blowout Prevention for Seal-Forming Portion", which claims the benefit of U.S. Provisional Application No. 62/138,009, filed Mar. 25, 2015 and U.S. Provisional Application No. 62/222,503, filed Sep. 23, 2015; each of the above-noted applications of which is incorporated herein by reference in its entirety.

4.6 REFERENCE SIGNS LIST

| Number | Feature Item |
|---|---|
| 1000 | patient |
| 1100 | bed partner |
| 3000 | patient interface |
| 3100 | seal-forming structure |
| 3200 | plenum chamber |
| 3300 | positioning and stabilising structure |
| 3400 | vent |
| 3600 | connection port |
| 3700 | forehead support |
| 4000 | RPT device |
| 4170 | air circuit |
| 5000 | humidifier |
| 6000 | patient interface |
| 6100 | frame assembly |
| 6120 | channel |
| 6175 | cushion assembly |
| 6200 | seal-forming structure |
| 6250 | lip seal |
| 6600 | elbow assembly |
| 6610 | swivel component |
| 6612 | swivel member |
| 6614 | diffuser material |
| 6616 | diffuser cover |
| 6618 | outlet |
| 6620 | elbow component |
| 6625 | swivel connector |
| 6630 | inner wall |
| 6632 | outer wall |
| 6634 | base wall |
| 6635 | opening |
| 6640 | vent hole |
| 6645 | pivot pin |
| 6650 | pinch arm |
| 6652 | barbed end |
| 6660 | first end |
| 6662 | ball portion |
| 6664 | recess |
| 6665 | port |
| 6667 | opening |
| 6670 | second end |
| 6671 | tubular end portion |
| 6672 | base wall |
| 6672A | wall portion |
| 6672B | wall portion |
| 6675 | rib |
| 6680 | AAV |
| 6682 | flap portion |
| 6684 | connecting portion |
| 6800 | headgear |
| 7100 | frame assembly |
| 7105 | channel |
| 7105A | end wall |
| 7105B | side wall |
| 7115 | annular flange |
| 7115A | inner surface |
| 7120 | channel |
| 7125 | ridge |
| 7175 | cushion assembly |
| 7176 | connecting portion |
| 7176A | leading edge |
| 7176B | outer side |
| 7600 | elbow assembly |
| 7610 | swivel component |
| 7620 | elbow component |
| 7625 | swivel connector |
| 7626 | tongue |
| 7630 | inner wall |
| 7632 | outer wall |
| 7632A | outer surface |
| 7632B | leading edge |
| 7633 | channel |
| 7634 | base wall |
| 7635 | opening |
| 7636 | rim |
| 7637 | track |
| 7639 | passageway |
| 7640 | vent hole |
| 7645 | pivot pin |
| 7650 | pinch arm |
| 7652 | barbed end |
| 7655 | hinging portion |
| 7657 | finger grip |
| 7660 | first end |
| 7662 | ball portion |
| 7664 | recess |
| 7665 | port |
| 7667 | opening |
| 7670 | second end |
| 7671 | tubular end portion |
| 7671A | groove |
| 7672 | base wall |
| 7672A | wall portion |
| 7672B | wall portion |
| 7673 | opening |
| 7674 | bridge |
| 7675 | rib |
| 7680 | AAV |
| 7682 | flap portion |
| 7684 | connecting portion |
| 7685 | hinge portion |
| 7690 | groove |
| 7692 | flat surface |
| 7695 | welding bead |
| 7696 | flat surface |
| 7698 | flat surface |
| 8000 | patient interface |
| 8100 | frame assembly |
| 8175 | cushion assembly |
| 8600 | elbow assembly |
| 8610 | swivel component |
| 8620 | elbow component |
| 8630 | inner wall |
| 8631 | lip or chevron |
| 8632 | outer wall |
| 8633 | channel |
| 8640 | vent hole |
| 8650 | pinch arm |
| 8665 | port |
| 8665.1 | rim |
| 8682 | AAV flap |

The invention claimed is:

1. An elbow assembly for a patient interface, the elbow assembly comprising:
   a component adapted to connect to a patient interface,
   wherein the component includes a plurality of vent holes for gas washout,
   wherein the component includes an inner radial wall and an outer radial wall that define a radial channel leading to the plurality of vent holes,
   wherein the inner radial wall functions as a baffle configured to segregate an inlet flow of pressurized gas from an outlet flow of exhaust gas,
   wherein the plurality of vent holes are provided along the outer radial wall to allow exhaust gas to be directed in a generally radial outward direction from the elbow assembly,
   wherein the radial channel is configured to guide the outlet flow from a generally axial direction down the radial channel to the generally radial outward direction as the exhaust gas exits the plurality of vent holes to atmosphere, and
   wherein at least a portion of the inner radial wall includes an inwardly extending lip or chevron structured and arranged to redirect flow in a manner that reduces noise and/or minimizes flow directly onto sensitive parts of a patient's face.

2. The elbow assembly according to claim 1, wherein the component is a swivel component, the swivel component adapted to allow rotation of the elbow assembly relative to the patient interface.

3. The elbow assembly according to claim 2, wherein the swivel component is adapted to allow 360° free rotation of the elbow assembly relative to the patient interface about a swivel axis.

4. The elbow assembly according to claim 2, wherein the swivel component comprises a hard-to-hard connection with the patient interface.

5. The elbow assembly according to claim 2, wherein the swivel component is structured to form a dynamic diametric seal and a dynamic face seal with the patient interface to provide a tortuous leak path.

6. The elbow assembly according to claim 2, further comprising an elbow component adapted to connect to an air circuit, wherein the swivel component and the elbow component, when coupled, provide a flow path therethrough from the air circuit to the patient interface.

7. The elbow assembly according to claim 1, further comprising tracks or guide walls within the radial channel to provide discrete flow paths to the plurality of vent holes.

8. The elbow assembly according to claim 7, wherein each vent hole and associated flow path includes a generally U-shaped cross-sectional shape.

9. The elbow assembly according to claim 7, wherein the vent holes and associated flow paths are only provided along a portion of a perimeter of the elbow assembly.

10. The elbow assembly according to claim 1, wherein the lip or chevron is structured and arranged to redirect the inlet flow away from the outlet flow.

11. The elbow assembly according to claim 1, wherein the lip or chevron curves and extends inwardly from the inner radial wall towards the inlet flow of incoming pressurized air.

12. The elbow assembly according to claim 1, wherein the lip or chevron is provided along an upper or superior portion of a perimeter of the inner radial wall.

13. The elbow assembly according to claim 1, wherein the plurality of vent holes includes at least 20 vent holes.

14. A patient interface for providing positive pressure therapy to a patient to ameliorate sleep disordered breathing, the patient interface comprising:
    a frame assembly;
    a seal-forming structure provided to the frame assembly and adapted to form a seal with a patient's face; and
    the elbow assembly according to claim 1.

15. The elbow assembly according to claim 1, wherein the component comprises an integral, one-piece construction.

16. The elbow assembly according to claim 1, wherein the component further comprises a base wall between the inner radial wall and the outer radial wall, and the base wall includes a curved surface to smoothly guide the outlet flow from the generally axial direction to the generally radial outward direction.

17. The elbow assembly according to claim 1, further comprising an elbow component adapted to connect to an air circuit, wherein the inner radial wall forms an opening including an interior surface configured to engage the elbow component.

18. The elbow assembly according to claim 17, wherein the inner radial wall includes a rim configured to retain the elbow component within the opening.

19. The elbow assembly according to claim 17, wherein the elbow component includes a ball portion engaged within the opening to form a ball and socket joint.

20. The elbow assembly according to claim 1, wherein the outer radial wall is configured to engage a frame assembly of the patient interface.

* * * * *